(12) United States Patent
Arlinghaus et al.

(10) Patent No.: US 6,537,804 B1
(45) Date of Patent: Mar. 25, 2003

(54) BCR-ABL DIRECTED COMPOSITIONS AND USES FOR INHIBITING PHILADELPHIA CHROMESOME STIMULATED CELL GROWTH

(75) Inventors: Ralph B. Arlinghaus, Bellaire, TX (US); Jiaxin Liu, Bellaire, TX (US); Gabriel Lopez-Berestein, Bellaire, TX (US); Dai Lu, Pearland, TX (US); Yun Wu, Houston, TX (US)

(73) Assignee: Board of Regents, The University of Texas Systems, Austin, TX (US)

( * ) Notice: Subject to any disclaimer, the term of this patent is extended or adjusted under 35 U.S.C. 154(b) by 0 days.

(21) Appl. No.: 09/101,059

(22) PCT Filed: Feb. 16, 1996

(86) PCT No.: PCT/US96/02091

§ 371 (c)(1),
(2), (4) Date: Jun. 21, 1999

(87) PCT Pub. No.: WO96/25520

PCT Pub. Date: Aug. 22, 1996

Related U.S. Application Data

(63) Continuation-in-part of application No. 08/390,353, filed on Feb. 16, 1995, now Pat. No. 6,107,457.

(51) Int. Cl.$^7$ .................. C07H 21/04; C12N 15/63
(52) U.S. Cl. ................ 435/320.1; 536/23.1; 530/300; 530/350; 435/6
(58) Field of Search ............... 435/6, 320.1; 536/23.1; 530/300, 350

(56) References Cited

U.S. PATENT DOCUMENTS

| | | | |
|---|---|---|---|
| 4,599,305 A | 7/1986 | Witte et al. | |
| 5,334,761 A | 8/1994 | Gebeyehu et al. | |
| 5,763,571 A | 6/1998 | Avruch et al. | |
| 5,795,859 A | 8/1998 | Rathjen et al. | |

FOREIGN PATENT DOCUMENTS

| | | |
|---|---|---|
| EP | 0338713 | 10/1989 |
| WO | WO 92/21032 | 11/1992 |

OTHER PUBLICATIONS

Druker et al., "Tyrosine phosphorylation of rasGAP and associated proteins in chronic myelogenous leukemia cell lines," *Blood*, 79(9):2215–2220, 1992.

Hoeve et al., "Cellular interactions of CRKL, an SH2–SH3 adaptor protein," *Cancer Res.*, 4:2563–2567, 1994.

Hoeve et al., "Tyrosine phosphorylation of CRKL in Philadelphia$^+$leukemia," *Blood*, 84(6):1731–1736, 1994.

Hou et al., "An interleukin–4–induced transcription factor: IL–4 Stat," *Science*, 265:1701–1706, 1994.

Liu et al., "BCR–ABL tyrosine kinase is autophosphorylated or transphosphorylates P160 BCR on tyrosine predominantly within the first BCR exon," *Oncogene*, 8:101–109, 1993.

Lu et al., "Tyrosine phosphorylation of P160 BCR by P210 BCR–ABL," *Blood*, 82(4):1257–1263, 1993.

Maxwell et al., "Analysis of P210$^{bcr-abl}$ tyrosine protein kinase activity in various subtypes of Philadelphia chromosome–positive cells from chronic myelogenous leukemia patients," *Cancer Res.*, 47:1731–1739, 1987.

McWhirter and Wang, "An actin–binding function contributes to transformation by the Bcr–Abl oncoprotein of Philadelphia chromosome–positive human leukemias," *EMBO J.*, 12(4):1533–1546, 1993.

McWhirter et al., "A coiled–coil oligomerization domain of Bcr is essential for the transforming function of Bcr–Abl oncoproteins," *Mol. Cell. Biol.*, 13(12):7587–7595, 1993.

Okabe et al., "Effect of Herbimycin A, an antagonist of tyrosine kinase, on bcr/abl oncoprotein–associated cell proliferations: Abrogative effect on the transformation of murine hematopoietic cells by transfectin of a retroviral vector expressing oncoprotein P210$^{bcr/abl}$ and preferential inhibition on Ph$^1$–positive leukemia cell growth," *Blood*, 80(5):1330–1338, 1992.

Pawson and Gish, "SH2 and SH3 domains: from structure to function," *Cell*, 71:359–362, 1992.

Pendergast et al., "BCR–ABL–Induced oncogenesis is mediated by direct interaction with the SH2 domain of the GRB–2 adaptor protein," *Cell*, 75:175–185, 1993.

Puil et al., "Bcr–Abl oncoproteins bind directly to activators of the Ras signalling pathway," *EMBO J.*, 13(4):764–773, 1994.

Tauchi et al., "Coupling between p210bcr–abl and Shc and Grb2 adaptor proteins in hematopoietic cells permits growth factor receptor–independent link to Ras activation pathway," *J. Exp. Med.*, 179:16–175, 1994.

Tauchi et al., "SH2–containing phosphotyrosine phosphatase Syp is a target of p210bcr–abl tyrosine kinase," *J. Biol. Chem.*, 269(21):15381–15387, 1994.

*Primary Examiner*—Sean McGarry
(74) *Attorney, Agent, or Firm*—Fulbright & Jaworski

(57) ABSTRACT

The present invention provides methods for detecting and quantitating BCR-ABL gene products and other abnormal ABL gene products of Ph$^1$-positive leukemic cells. The invention further provides methods for determining the relative number of leukemic cells compared with normal ABL cells to assess the tumor burden of a patient. In another aspect, the methods of the present invention can be used to determine a specific phase of leukemia, particularly chronic-phase CML.

22 Claims, 29 Drawing Sheets

BCR-ABL DIRECTED COMPOSITIONS AND USES FOR INHIBITING PHILADELPHIA CHROMESOME STIMULATED CELL GROWTH

The present application is a continuation-in-part of co-pending U.S. patent application Ser. No. 08/390,353, filed Feb. 16, 1995, now U.S. Pat. No. 6,107,457.

The U.S. Government owns rights in the present invention pursuant to grant number CA 65611 from the National Institutes of Health.

FIELD OF THE INVENTION

The present invention relates generally to the field of malignant cell proliferation. More particularly, it provides compositions and methods to limit Bcr-Abl oncoprotein-driven malignant cell proliferation. Peptide and protein molecules are provided that inhibit various Bcr-Abl signal transduction pathways, e.g., activation of the Ras protein. Methods for reducing Philadelphia chromosome-positive cells in cell populations, including bone marrow culture, and methods of treating various leukemias are also provided.

BACKGROUND OF THE INVENTION

The Philadelphia chromosome (Ph[1]) is associated with the bulk of chronic myelogenous leukemia (CML) patients (more than 95%), 10–25% of acute lymphocytic leukemia (ALL) patients, and about 2–3% of acute myelogenous leukemias (AML). This abnormal chromosome fuses most of the ABL gene to the 5' two-thirds of the BCR gene.

A number of different kinds of evidence support the contention that Bcr-Abl oncoproteins, such as p210 and p185 BCR-ABL, are causative factors in these leukemias (Campbell et al., 1991). The malignant activity is due in large part to the Bcr-Abl protein's highly activated protein tyrosine kinase activity and its abnormal interaction with protein substrates (Campbell et al., 1991, Arlinghaus et al., 1990). The Bcr-Abl oncoprotein p210 Bcr-Abl is associated with both CML and ALL, whereas the smaller oncoprotein, p185 BCR-ABL, is associated with ALL patients, although some CML patients also express p185 (Campbell et al., 1991).

Some reports suggest that Bcr-Abl oncoproteins, p210 and p185 BCR-ABL, function at least in part by activating the Ras pathway. The RAS gene is a proto-oncogene involved in controlling normal cell growth. When continuously activated, the Ras protein becomes a potent cancer gene product. Bcr-Abl oncoproteins have been observed by the present inventors and others to perturb normal Ras function (Pendergast et al., 1993).

The mechanism by which Bcr-Abl oncoproteins activate p21 Ras is believed to involves several factors. One event involves the autophosphorylation of the Bcr-Abl oncoprotein on tyrosine residues within the coding sequence of the first Bcr exon (Liu et al., 1993). This finding was unexpected, as it had previously been postulated that Bcr-Abl phosphorylates itself on Abl tyrosines, not Bcr tyrosine residues.

Several adaptor proteins have been implicated in Ras-activation as well. FIG. 2 lists several such adaptor proteins that contain SH2/SH3 motifs. Such domains have been observed in proteins involved in transmitting growth signals to the nucleus (Pawson et al., 1992).

Grb2 is an adaptor protein that binds to tyrosine phosphorylated receptor proteins. Bcr-Abl induced oncogenesis has also been reported to be mediated by direct interaction with the SH2 domain of Grb2 (Pendergast et al., 1993; Puil et al., 1994). Grb2 also binds mSos1, a GTP exchange factor (see FIG. 3). The latter activates Ras by forming GTP/Ras. GTP/Ras in turn activates Raf, a serine/threonine protein kinase that activates Mek. Mek is a kinase that phosphorylates and activates MAP kinase. The latter is believed to activate and/or regulate various transcription factors (i.e., c-Jun), resulting in cell growth (FIG. 4).

Another peptide that has been implicated in the malignant effects of Bcr-Abl involves Shc (Puil et al., 1994). Crkl is another adaptor molecule that forms a protein/protein interaction with Bcr-Abl (Reichman et al., 1992; Ten Hoeve et al., 1993; 1994). Still another adaptor molecule that interacts with Bcr-Abl is p120 Ras Gap (Druker et al. 1992).

Another protein/protein interaction that has been examined in relation to Bcr-Abl induced malignancy concerns the formation of tetramer structures. In Philadelphia chromosome-positive human leukemias, the c-abl proto-oncogene on chromosome 9 becomes fused to the bcr gene on chromosome 22, and chimeric Bcr-Abl proteins are produced. The fused Bcr sequences activate the tyrosine kinase, actin-binding, and transforming functions of Abl.

Activation of the Abl transforming function is believed to require two distinct domains of Bcr: domain 1 (Bcr amino acids 1 to 63) and domain 2 (Bcr amino acids 176–242) (McWhirter et al., 1993). Domain 1 of Bcr has been shown to form a homotetramer (McWhirter et al., 1993). The Bcr-Abl tetramer activates its inherent Abl tyrosine kinase activity, its actin binding function, and its cellular transformation function (McWhirter et al., 1993). Disruption of the coiled coil by insertional mutagenesis inactivates the oligomerization function and the ability of Bcr-Abl to transform Rat-1 fibroblasts.

Despite the description of certain events and molecules that are believed to be involved in Bcr/Abl function and pathologies associated with the activities of its gene product, comprehensive strategies for controlling Bcr/Abl and, e.g., its activation of the Ras oncogene, have not been developed. Thus, a need continues to exist in the scientific and medical arts for approaches that target effectively and specifically inhibit Bcr/Abl. Such techniques would provide new therapies for inhibiting Philadelphia chromosome-positive cells in tissues, such as in bone marrow.

SUMMARY OF THE INVENTION

The present invention overcomes certain of the limitations of the prior art by defining specific peptide sequences from Bcr-Abl that inhibit Bcr-Abl function and activation. The peptides and compositions of the invention are thus useful in methods for inhibiting Bcr-Abl, for purging bone marrow of Philadelphia chromosome-positive cells in bone marrow samples and for treating various leukemias, including chronic myelogenous leukemia (CML), acute lymphocytic leukemia (ALL) and acute myelogenous leukemias (AML).

The peptides of the present invention are those comprising a sequence based upon a segment of a Bcr-Abl amino acid sequence that includes at least one of a combination of several tyrosine residues found by the present inventors to be important in Bcr-Abl function. These are termed herein the "tyrosine-containing peptides". Generally, the compositions and methods of the invention require that at least one tyrosine-containing peptide be present.

The amino acid sequence of the first exon of p160 Bcr is given in SEQ ID NO:1. Tyrosines are present at residues 58, 70, 177, 231, 246, 276, 279, 283, 316, 328 and 360. The particularly important tyrosines in the context of the present invention are tyrosines at positions 177, 283 and 360, and also tyrosine 328.

The present invention thus provides purified peptides and polypeptides, of between about 4 and about 500 amino acids in length, that have or comprise a contiguous amino acid sequence from the Bcr-Abl protein (of SEQ ID NO:1), which sequence includes or surrounds at least one of tyrosine 177, tyrosine 283, tyrosine 360, or even tyrosine 328, which peptides or polypeptides become phosphorylated on tyrosine 177, 283, 360 and/or 328 upon contact with active Bcr-Abl.

These peptides are thus characterized as being substrates for the tyrosine phosphorylating activity of Bcr-Abl. The peptides are also characterized as being capable of effectively competing with Bcr as a substrate for Bcr-Abl, and being capable of reducing the Bcr-Abl-mediated tyrosine phosphorylation of Bcr in an intact cell that contains Bcr-Abl.

Exemplary useful peptides including tyrosine 177 are those comprising the sequence of SEQ ID NO:8 (positions 164 to 181 of SEQ ID NO:1). Exemplary useful peptides including tyrosine 283 are those comprising the sequence of SEQ ID NO:11 (positions 255 to 293 of SEQ ID NO:1). It is currently preferred that the peptide include the tyrosine in a generally central region, rather than at the extreme termini of the peptide.

Although understanding the mechanism of action of any given peptide is not necessary in order to practice the invention, it should be noted that peptides containing tyrosine 177 or tyrosine 283 likely function by inhibiting the oncogenic effects of Bcr-Abl. This is believed to be achieved by the peptides competing with other substrates, particularly Bcr, in order to become phosphorylated by Bcr-Abl. In effect, this reduces the Bcr-Abl-driven phosphorylation of other cellular targets and limits the adverse effects of Bcr-Abl.

Still further useful tyrosine-containing peptides are those containing tyrosine 360. Exemplary useful peptides of this group include those comprising the sequence of SEQ ID NO:10 (positions 353 to 364 of SEQ ID NO:1) and SEQ ID NO:22 (positions 350 to 366 of SEQ ID NO:1). It is currently preferred that the a phosphorylated serine, corresponding to Serine 354, be provided in these peptides.

The advantageous effects of peptides containing tyrosine 360 are believed to be based on the stimulation of the beneficial effects of Bcr, which neutralizes Bcr-Abl. Such Bcr neutralization is achieved, in part, by its Serine/Threonine kinase activity. Phosphorylation of Bcr tyrosine 360 and tyrosine 328 by Bcr-Abl has been shown by the inventors to reduce its Serine/Threonine phosphorylating activity. Importantly, the Ser 354 form of a tyrosine 360-containing peptide is demonstrated herein to be a direct inhibitor of the Bcr-Abl oncoprotein's tyrosine kinase activity.

Therefore, peptides containing tyrosine 360 sequences, or even tyrosine 328 sequences, will compete with Bcr as a Bcr-Abl substrate and will reduce the levels of Bcr-Tyr-360-P, thereby facilitating the beneficial effects of Bcr. However, it will again be understood that the present invention is still useful even if this proposed mechanism of action does not prove to be entirely correct.

In terms of the tyrosine-containing peptides of the invention, peptides that include at least a 4-mer or 5-mer sequence, or preferably, that include at least a 6-mer or 7-mer sequence, that includes the tyrosine of importance are expected to provide effective molecules in the compositions for Bcr-Abl inhibition. For example, a sequence that includes at least the amino acid sequence of SEQ ID NO:24 (positions 176 to 180 of SEQ ID NO:1) may be employed. Exemplary 5- and 7-mers are represented by SEQ ID NO:25 (positions 359 to 363 of SEQ ID NO:1) and SEQ ID NO:26 (positions 279 to 285 of SEQ ID NO:1).

However, longer peptides, from about 10–12 to 15–20, to about 50, 100, 150, 200, 250, 300, 350, 400 or about 500 residues or so may also be used. An exemplary 13-mer is SEQ ID NO:27, corresponding to positions 168 to 180 of SEQ ID NO:1. A currently preferred longer peptide is that of SEQ ID NO:28.

Shorter peptides, such as SEQ ID NO:10 and SEQ ID NO:22, will generally be administered to cells or patients as a peptide or liposomal-peptide formulation. Longer peptides and polypeptides, such as SEQ ID NO:28, will generally be administered to cells or patients using gene therapy, in which a vector that expresses the peptide or polypeptide is employed.

While a given peptide alone will be useful in inhibiting Bcr-Abl, the compositions and methods of the present invention may include two or more such peptides. Where two peptides are employed, it may be preferred to use peptides with sequences including distinct tyrosine regions, preferably selected from those regions of SEQ ID NO:1 including 177, 283 and/or 360. Three distinct peptides including the foregoing various tyrosine regions may also be used to advantage.

A single peptide that itself contains sequences surrounding two of the three tyrosines at positions 177, 283 and 360 may also be used. Such peptides may contain only contiguous Bcr-Abl sequences, or may contain two contiguous stretches of Bcr-Abl sequence operatively joined by an irrelevant, preferably flexible, linker sequence.

Further, the use of a single peptide that contains a contiguous sequence that includes each of the three tyrosines at positions 177, 283 and 360 is also contemplated. An exemplary peptide containing only contiguous Bcr-Abl sequences is SEQ ID NO:28, which begins at residue 64 and ends at residue 413 of SEQ ID NO:1. Peptides may also contain longer stretches of Bcr-Abl sequences or other sequences as desired.

Other peptides of the present invention that may be used in addition to at least one tyrosine-containing peptide are those that comprise the sequence of an important binding site on Bcr-Abl for an adaptor molecule, i.e., a molecular target of the Bcr-Abl oncoprotein. These are termed the "binding site peptides".

The binding site peptides for use in the invention are purified peptides and polypeptides, of between about 4 and about 500 amino acids in length, that have or comprise a contiguous adaptor molecule binding site sequence from the Bcr-Abl sequence, which peptides or polypeptides bind to an adaptor molecule.

The binding site peptides may also contain tyrosine residues. However, binding site peptides are characterized as binding to an adaptor molecule, such as Grb2, Shc, Crkl, Ras Gap or an N-terminal coiled-coil region of Bcr. Preferably, they are characterized as inhibiting the binding of Bcr-Abl to an adaptor molecule, and as being capable of reducing Bcr-Abl-adaptor molecule interactions in an intact cell.

The binding site peptides for use in the compositions and methods of the invention generally mimic the sites on Bcr-Abl to which key oncoproteins bind. In these embodiments, supplementary peptides are provided that bind one or more signal transduction molecules, such as Shc, Crkl, Ras Gap and/or Grb2/mSos1, thereby preventing these molecules from carrying out their growth-promoting functions.

Accordingly, the tyrosine-containing peptide compositions of the invention may further comprise one or more of the binding proteins: a purified peptide that binds to an Abl SH3 binding protein-rich region of Shc; a purified peptide that binds to a proline-rich ABl binding site on Crkl; a purified peptide that binds to an SH2 domain of p120 Ras Gap; and/or a purified peptide or protein that binds to an N-terminal coiled-coil region of Bcr.

Exemplary compositions of the invention are those that additionally comprise one or more peptides that bind an Abl SH3 binding protein-rich region of Shc. Shc binds to Grb2 and this complex has potential to activate Ras. Peptides that bind to Shc will comprises a sequence from the Abl region, not from the Bcr region.

Further binding peptides of the present invention are those that inhibit binding of Crkl to Bcr-Abl. Crkl is a 38-kDa protein that forms complexes with both Abl and Bcr/Abl and is tyrosine phosphorylated by Abl and Bcr-Abl. Peptides that mimic the proline-rich Abl binding site on CRKL are thus also components of some embodiments of the present invention.

Still further Bcr/Abl peptides included in these embodiments are those that interact with p120 Ras Gap. Peptides of this nature are described more particularly as peptides that bind an SH2 domain of p120 Ras Gap. These peptides involve tyrosine 279 and a tyrosine outside of the first exon of Bcr. Exemplary useful peptides are those comprising the sequence of SEQ ID NO:11 (positions 255 to 293 of SEQ ID NO:1) and SEQ ID NO:12.

In further embodiments, the compositions of the invention will comprise one or more peptides or proteins that bind an N-terminal coiled-coil region of Bcr. These peptides and proteins are exemplified by peptides that comprise a sequence corresponding to SEQ ID NO:2 (positions 1 to 63 of SEQ ID NO:1); SEQ ID NO:3 (positions 1 to 71 of SEQ ID NO:1); SEQ ID NO:4 (positions 28 to 58 of SEQ ID NO:1); a sequence corresponding to SEQ ID NO:5 (positions 1 to 159 of SEQ ID NO:1); a sequence corresponding to SEQ ID NO:6 (positions 1 to 221 of SEQ ID NO:1); or a sequence corresponding to SEQ ID NO:7 (positions 1 to 413 of SEQ ID NO:1).

The present inventors observed that the Bcr protein contains the consensus binding site Y*VNV (SEQ ID NO:13) for Grb2 that enables the Bcr-Abl oncoprotein to form a complex with Grb2. Tyrosine phosphorylation of Bcr sequences at tyrosine 177 causes Grb2/mSos1 to bind membrane-bound Bcr-Abl and to activate p21 Ras (FIG. 5).

Peptides comprising the Y*VNV consensus binding site (SEQ ID NO:13; residues 177 to 180 of SEQ ID NO:1) will thus interfere with Grb2 binding to Bcr-Abl block Bcr-Abl induced malignant effects, particularly when used in combination with one or more of the Shc, Crkl, SH2 or p120 Ras Gap binding sequences. The Bcr peptide GHGQPGADAEKPFp.$Y_{177}$VNVE, SEQ ID NO:8 (residues 164–181 of SEQ ID NO:1), also strongly binds to the SH2 binding site on Grb2 and may be used in the compositions of the invention.

The binding site peptides of the invention may thus be any length from between about 4 amino acids to about 500 amino acids or so, so long as the peptide is of sufficient length to include an effective binding site, as described herein.

Any of the peptide compositions of the present invention may further include a pharmaceutically acceptable carrier, such as Ringers solution, saline, and the like. Such carriers are known to those of ordinary skill in the pharmaceutical arts.

Another embodiment of the invention provides compositions comprising one or more of the above tyrosine-containing peptides in association with a liposomal formulation. The peptides may be encapsulated within the liposome or simply maintained in functional association with the liposome.

The foregoing peptide compositions may be used in enriching for Philadelphia chromosome-negative cells in a mixture of cells containing Philadelphia chromosome-positive cells.

Further provided by the present invention is a first expression vector, such as a plasmid, adenovirus or retrovirus, that contains a first DNA sequence or sequences that encodes and expresses at least one of the tyrosine-containing peptides of the invention. DNA sequences that encodes the amino acid sequence of SEQ ID NO:1 are known to those of skill in the art and are further described herein. The identification of a particular coding region that encodes one or more tyrosine-containing peptides will be straightforward to one of skill in the art.

The first expression vector may further comprise a second DNA sequence or sequences that encodes and expresses at least one of: a peptide that binds an Abl SH3 binding protein-rich region of Shc; a peptide that binds a proline-rich Abl binding site on Crkl; a peptide that binds an SH2 domain of p120 Ras Gap; a peptide or protein that binds an N-terminal coiled-coil region of Bcr; and/or a peptide that binds an SH2 binding site on Grb2.

Equally, a second expression vector, such as a plasmid, adenovirus or retrovirus, may be provided for use with the first expression vector described above. The second expression vector will generally be a plasmid, adenovirus or retrovirus that contains a DNA sequence or sequences that encodes and expresses at least one of: a peptide that binds an Abl SH3 binding protein-rich region of Shc; a peptide that binds a proline-rich Abl binding site on Crkl; a peptide that binds an SH2 domain of p120 Ras Gap; a peptide or protein that binds an N-terminal coiled-coil region of Bcr; and/or a peptide that binds an SH2 binding site on Grb2.

In certain embodiments, an amphotropic retrovirus, defective in replication but capable of infecting bone marrow cells from animals or patients, is provided that expresses one or more of the peptides of the present invention, either singly or as part of a fused polypeptide. AAV, adenoviral and plasmid vectors associated with liposomes are also provided.

Methods of the invention provide for the inhibition, killing or effective reversal of phenotype of Philadelphia chromosome-positive cells. The methods generally comprise contacting a Philadelphia chromosome-positive cell, or a population of cells that includes Philadelphia chromosome-positive cells, with a composition that includes or encodes a biologically effective amount of any one of, or a combination of, any of the tyrosine-containing peptide compositions described herein. The compositions are maintained in contact with the cells for a period of time effective to result in inhibition or killing of the Philadelphia chromosome-positive cells.

It will be understood that the methods may be achieved by contacting one or more Philadelphia chromosome-positive cells with an effective amount of one or more tyrosine-containing peptides themselves. Equally, the cells may be contacted with one or more expression vectors, including viral vectors, that encode and express one or more such tyrosine-containing peptides.

The compositions for use in such methods will generally include or encode at least one peptide having or comprising a sequence that includes at least one of the tyrosine residues 177, 283 or 360 from SEQ ID NO:1. In certain embodiments, the composition will further include or encode: a peptide that binds an Abl SH3 binding protein-rich region of Shc; a peptide that binds a proline-rich Abl binding site on Crkl; a peptide that binds an SH2 domain of p120 Ras Gap; a peptide or protein that binds an N-terminal coiled-coil region of Bcr; and/or a peptide that binds an SH2 binding site on Grb2.

In the methods for inhibiting, killing or reversing the phenotype of Philadelphia chromosome-positive cells, the cells or populations of cells may be contacted either in vivo or in vitro. The methods thus encompass both in vivo treatment and in vitrotex vivo protocols. Both in vivo and in vitro, the cells may be contacted with a composition of peptides, a composition of liposomally-associated peptides and/or with a composition comprising an expression vector or virus that encodes and expresses the peptides. The compositions will generally be pharmaceutically acceptable.

The invention thus further provides methods for enriching Philadelphia chromosome-negative cells in a mixture of cells containing Philadelphia chromosome-positive cells. The methods generally comprise contacting, for en effective period of time, a mixture of cells, such as a bone marrow sample, that contains, or is suspected of containing, Philadelphia chromosome-positive cells with a composition that includes or encodes a Bcr-Abl-inhibiting amount of any one of, or a combination of, any of the tyrosine-containing peptide compositions of the present invention. In certain embodiments, the bone marrow will be obtained from a patient having CML, AML or ALL.

The invention particularly contemplates that the bone marrow sample treated with the peptides of the invention will be re-administered to the patient from whom it was obtained. The invention thus provides methods for ex vivo treatment and bone marrow purging prior to autologous bone marrow transplants. The treated bone marrow samples enhance the immunocompetency of the transplant recipient.

In the methods for enriching Philadelphia chromosome-negative cells in a mixture of cells containing Philadelphia chromosome-positive cells, the Philadelphia chromosome-negative cells are generally enriched relative to numbers naturally occurring in a sample containing Philadelphia chromosome positive cells. An example is enriching for Philadelphia chromosome-negative cells relative to numbers naturally occurring in a bone marrow sample from a patient having CML, AML or ALL.

In still further embodiments, the invention provides methods for purging a bone marrow sample of Philadelphia chromosome-positive cells. The methods generally comprise exposing, for an effective period of time, a bone marrow sample that contains Philadelphia chromosome-positive cells to a composition that includes or encodes any one of, or a combination of, any of the tyrosine-containing peptide compositions of the present invention in an amount effective to reduce the numbers of Philadelphia chromosome-positive cells in the bone marrow sample.

Yet still further embodiments of the invention provide methods of treating a patient having or suspected of having a Philadelphia chromosome-positive leukemia, comprising treating a bone marrow sample of the patient with a composition including or encoding at least one of the tyrosine-containing peptides of the invention in an amount effective to prepare an essentially leukemia cell-free autologous bone marrow sample (i.e., using a leukemia cell-cytotoxic amount) and administering the treated sample to the patient.

The treatment methods also comprise obtaining a bone marrow sample from the patient, contacting the bone marrow sample ex vivo with a composition that includes or encodes any one or more of the tyrosine-containing peptides of the invention in a therapeutic amount and for a period of time effective to purge Philadelphia chromosome-positive cells from the bone marrow sample and re-administering the purged bone marrow sample to the patient.

For the purpose of this invention, an autologous bone marrow sample is defined as a sample of bone marrow from a patient intended for re-administration to the patient after treatment outside the body.

A defined method for treating leukemia in a patient according to the present invention comprises: administering to a patient with leukemia a chemotherapeutic regimen sufficient to generate at least some cytogenetic remission in the patient; obtaining a bone marrow sample from the patient in remission; exposing the bone marrow sample to a Philadelphia chromosome-positive cell cytotoxic concentration of tyrosine-containing peptides to provide an essentially Philadelphia chromosome-positive cell free bone marrow sample; and reintroducing the essentially Philadelphia chromosome-positive cell free bone marrow sample into the patient, wherein the reintroduction replaces Philadelphia chromosome-positive marrow cells with normal hematopoietic progenitor cells.

The approaches of the present invention provide an improvement over current strategies, e.g., anti-sense Bcr-Abl approaches, in that the activity of Bcr-Abl is inhibited while at the same time neutralizing more than one of the principal targets of Bcr-Abl oncoproteins.

The present invention also has practical uses in that the peptides mat be used as molecular weight markers, protein stain standards and as standards for radioiodination.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A depicts a normal progenitor cell.

FIG. 1B depicts a leukemic progenitor cell.

FIG. 6A shows a Western blot with Anti-Tyr antibody. Bcr-Abl induces tyrosine phosphorylation of Bcr221 and Bcr413 but not Bcr159, indicating that the first two tyrosines of Bcr are not targets for Bcr-Abl. The next tyrosine is at residue 177, and it is expected to be phosphorylated by Bcr-Abl (Puil et al., 1994). Bcr221 is tyrosine phosphorylated, but as with Bcr413, only in the presence of Bcr-Abl.

FIG. 6B shows a Western Blot of the same extracts probed with anti-Bcr 1–16. Note that all three Bcr proteins fragments are specifically expressed under both conditions.

FIG. 8A, p210-wild type; FIG. 8B, p210-F283; FIG. 8C, p210-F276; FIG. 8D, p185-F360.

FIG. 20A, B15 cells cultured in 20% FCS containing RPMI media with either the 3' BCR antisense oligonucleotides (10 $\mu$M at day 1) (open squares) or the sense oligonucleotides (10 $\mu$M at day 1) (closed squares).

FIG. 20B, M3.16 cells cultured in 10% FCS containing DMEM media with either the 3' BCR antisense oligonucleotides (open squares) or the sense oligonucleotide (closed squares) as above. Oligonucleotides were added at day 1 at a final concentration of 10 $\mu$M and added again at day 5 at half of the initial concentration. Cell viability was determined by trypan blue dye exclusion. The data are the mean +/–SEM of a triplicate analysis.

FIG. 23A, Lane 1, boiled Bcr fragment mixed with P185 BCR-ABL; lane 2, untreated Bcr fragment mixed with P185 BCR-ABL; lane 3, 50 $\mu$g of Bcr S17K (not phosphorylated) added to P185 BCR-ABL; lane 4, P185 BCR-ABL alone.

FIG. 23B, Western blotting of the immune complexes containing P185 BCR-ABL. The P185 protein present in lanes 2 and 4 of FIG. 23A was analyzed by Western blotting with anti-Bcr 181–194. Lane 1, P185 detected in lane 2 of FIG. 23A; lane 2, P185 detected in lane 4 of FIG. 23A. This shows that although the kinase activity of Bcr-Abl was dramatically reduced by the Bcr fragment protein, the amount of Bcr-Abl in the reaction mixtures was similar.

FIG. 23C. The anti-Bcr 181–194 antibody does not inhibit the Bcr-Abl tyrosine kinase activity. In this study anti-Bcr 181–194 antibody was added to a reaction mixture containing P185 BCR-ABL to determine whether the antibody itself was responsible for the inhibitory activity exhibited by the antibody/Bcr fragment complex (FIG. 23A, lane 2). Lane 1, P185 BCR-ABL alone; lane 2, P185 BCR-ABL plus protein A Sepharose beads containing the anti-Bcr 181–194. The top pattern is the P185 autokinase activity; the bottom portion is the anti-Abl 8E9 Western blot of the immune complexes. These results show that the anti-Bcr antibody itself does not inhibit the Bcr-Abl kinase activity.

DETAILED DESCRIPTION OF THE PREFERRED EMBODIMENTS

Figure 1A:
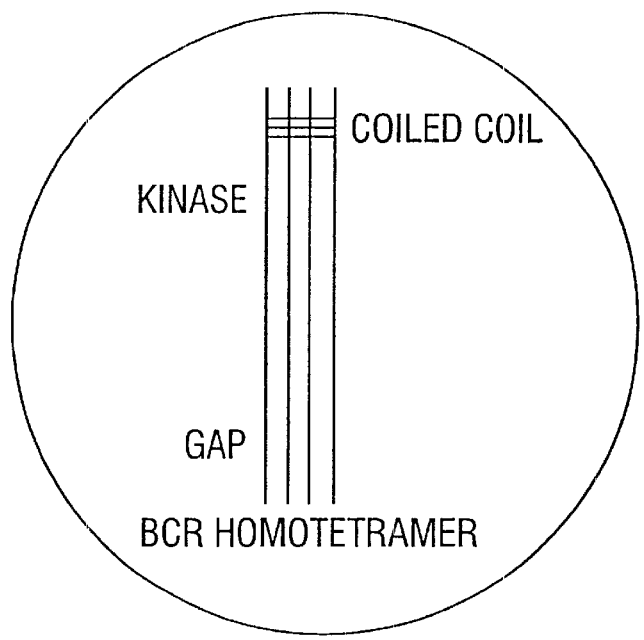
FIG. 1A and FIG. 1B provide models for Bcr and Bcr-Abl interaction.
Figure 1B:
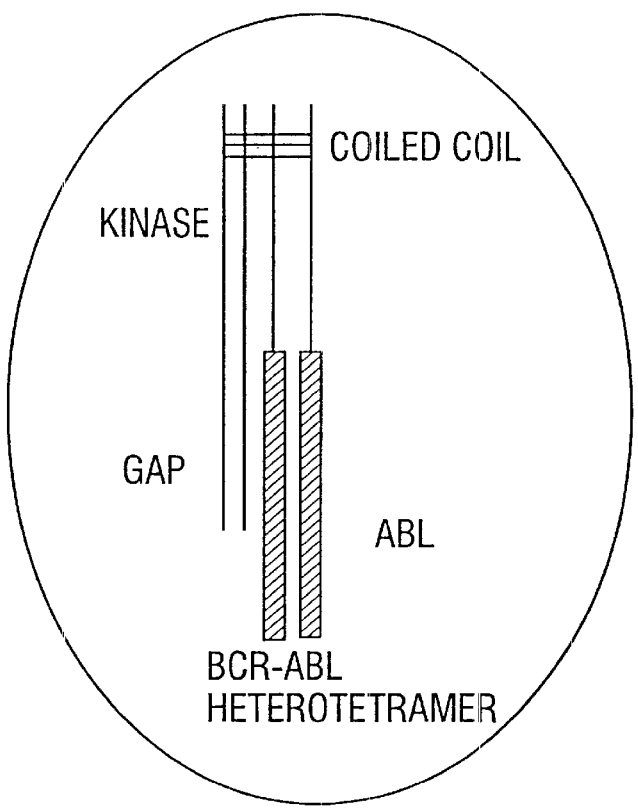

The present invention provides one or more peptides comprising BCR sequences including $Y^{177}$, $Y^{283}$ and/or $Y^{360}$, or even $Y^{328}$, for the inhibition of Bcr-Abl oncogenic activities. The peptides also inhibit BCR-Abl-adaptor protein interactions (FIG. 1A and FIG. 1B). This inhibition prevents the adaptor proteins from participating in the cascade that leads to adverse effects, such as Ras oncogene activation.

1. Tyrosine-Containing Peptides

Currently preferred tyrosine-containing peptides are those comprising sequences of SEQ ID NO:8, SEQ ID NO:11, SEQ ID NO:10, SEQ ID NO:22, and the longer peptide, SEQ ID NO:28. However, peptides comprising sequences of any one or more of SEQ ID NO:1 through SEQ ID NO:28 may be used in the present invention.

These peptides have a tyrosine within their sequence, at the beginning, middle or end, with the middle of the peptide being generally preferred.

The peptides may be phosphorylated at tyrosine residues or they may be provided in nonphosphorylated form because the target cell has the capacity to phosphorylate the peptides. Peptides comprising $Y^{177}$ and $Y^{283}$ will generally be provided in nonphosphorylated form, in order to compete for tyrosine kinase activity. Peptides comprising $Y^{360}$ will generally be provided in a form that includes a phosphorylated serine, e.g., corresponding to position 354, in order to be most effective. Peptides comprising $Y^{328}$ may even be provided.

In addition to the mechanisms discussed hereinabove, phosphorylation of tyrosine 328 and 360 is contemplated to alter the structure of Bcr. Bcr is a novel Ser/Thr kinase not structurally related to other Ser/Thr kinases. Tyrosine 328 and 360 are located around two pairs of cysteines important in Bcr function. When tyrosines 360 and/or 328 become phosphorylated it is contemplated by the inventors to induce a conformational change that hampers Bcr function. Thus, peptides comprising tyrosine 328-surrounding sequences form another aspect of the invention.

The Bcr-Abl peptides of the present invention may be virtually any length from about 3–4 amino acids up to about 5, 6, 7, 8, 9, 10, 11, 12, 13, 14, 15, 16, 17, 18, 19 or about 20 amino acids long. Peptides of about 25, 30, 35, 40, 45, 50, 75, 100, 150, 200, 250, 300, 350, 400, 450 or about 500 amino acids in length may also be employed.

Exemplary shorter peptides are those based upon the sequence of SEQ ID NO:24. SEQ ID NO:9 (positions 314 to 320 of SEQ ID NO:1), surrounding tyrosine 316, may even be used in certain embodiments. Exemplary longer peptides include SEQ ID NO:23 (positions 299 to 351 of SEQ ID NO:1) and SEQ ID NO:28.

A further embodiment of the invention is the use of the full length normal Bcr protein. The normal Bcr protein has 1271 amino acids and the sequence is presented in Campbell and Arlinghaus (1991), incorporated by reference herein.

2. Binding Site Peptides

Binding site peptides that comprise the sequence of an important binding site on Bcr-Abl for an adaptor molecule may also be used in the present invention. The binding site peptides are generally characterized as binding to an adaptor molecule, such as Grb2, Shc, Crkl, Ras Gap or an N-terminal coiled-coil region of Bcr.

Preferred binding site peptides are: peptides that bind to an Abl SH3 binding protein-rich region of Shc; peptides that bind to a proline-rich ABl binding site on Crkl; peptides that bind to an SH2 domain of p120 Ras Gap; and peptides or proteins that bind to an N-terminal coiled-coil region of Bcr. The peptides or proteins that bind an N-terminal coiled-coil region of Bcr include peptides of any one of SEQ ID NO:2 through SEQ ID NO:7.

3. Biologically Functional Equivalents

Modifications and changes may be made in the sequence of the peptides of the present invention, except for the tyrosine residue that is the site of phosphorylation and other key residues, and still obtain a peptide having like or otherwise desirable characteristics.

One of skill in this art would realize, in light of the present disclosure, that the tyrosine site of phosphorylation of the peptides is not amenable to replacement; nor are other key residues, such as the asparagine at position 179 of SEQ ID NO:1, or the Serine 354 equivalent in SEQ ID NO:22. However, functional equivalents of other amino acids are acceptable in the present invention.

In a functional equivalent, certain amino acids may be substituted for other amino acids in a protein structure without appreciable loss of interactive binding capacity with structures such as, for example, binding sites on substrate molecules. Since it is the interactive capacity and nature of a protein that defines that protein's biological functional activity, certain amino acid sequence substitutions can be made in a protein sequence (or, of course, its underlying DNA coding sequence) and nevertheless obtain a protein with like (agonistic) properties.

It is thus contemplated by the inventors that various changes may be made in the sequence of the tyrosine-containing proteins or peptides (or underlying DNA) without appreciable loss of their biological utility or activity. Equally, the same considerations may be employed to create a protein or peptide with countervailing (e.g., antagonistic) properties.

In terms of functional equivalents, it is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. In particular, where shorter peptides are concerned, it is contemplated that less changes will be tolerated. Of course, a plurality of distinct proteins/peptides with different substitutions may easily be made and used in accordance with the invention.

It is also well understood that where certain residues are shown to be particularly important to the biological or structural properties of a protein or peptide, such as the tyrosines of the present invention, such residues may not generally be exchanged. This is clearly the case in the present invention, as detailed above.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

To effect more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent, and in particular, an immunologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid. A table of amino acids and their codons is presented herein (Table 1) for use in such embodiments, as well as for other uses, such as in the design of probes and primers and the like.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In addition to the peptidyl compounds described herein, the inventors also contemplate that other sterically similar compounds may be formulated to mimic the key portions of the peptide structure. Such compounds, which may be termed peptidomimetics, may be used in the same manner as the peptides of the invention and hence are also functional equivalents. The generation of a structural functional equivalent may be achieved by the techniques of modelling and chemical design known to those of skill in the art. The art of modelling is now well known, and by such methods a chemical that mimics a given peptide's function can be designed and then synthesized. It will be understood that all such sterically similar constructs fall within the scope of the present invention.

4. Peptide Synthesis

Peptides less than about 45 amino acids are generally synthesized chemically. The synthesis of peptides is readily achieved using conventional peptide synthetic techniques such as the solid phase method (e.g., through the use of commercially available peptide synthesizer such as an Applied Biosystems Model 430A Peptide Synthesizer, Foster City, Calif., or Vega Synthesizer, DuPont Inc., Wilmington, Del.).

The solid phase technique uses the method of Merrifield (Merrifield, 1963, incorporated by reference herein) using an automatic peptide synthesizer with standard t-butoxycarbonyl (t-Boc) chemistry. The amino acid composition of a synthesized peptides is determined by amino acid analysis, e.g., with a Waters Pico-tag analyzer (Medford, Mass.), to confirm that they correspond to the expected compositions. The purity of the peptides is determined by sequence analysis or HPLC.

It is generally desirable for the amino terminal end of synthetic peptides to be protected from degradation by having an N-terminal acetyl group. This can be accomplished during synthesis of the peptide by using acetic anhydride to acetylate the N-terminal end. Similarly, protection for the carboxyl end may be achieved by forming an amide bond, as described in Example 2. Such protecting groups will generally reduce the degradation of the synthetic peptides by proteolytic enzymes once they are introduced into a cell.

The phosphorylated form of peptides is obtained in vitro by using standard methods for synthesis of peptides. The amino acid to be phosphorylated is introduced without side-chain protection. The terminal residue should be Boc protected by either direct incorporation of a Boc protected amino acid or acylation of the free amino group with $Boc_2O$. The resin is washed and placed into the reaction vessel. The peptidyl resin and reaction vessel are dried overnight under high vacuum at 40° C., sealed with a rubber septum and flushed with dry argon.

An ampoule of DNA grade tetrazole is dissolved in dry DMF, DMA or $CH_3CN$ and 50 eq. and transferred to the reaction vessel using a dried argon flushed gas tight syringe. 10 eq. of di-t-butyl-N,N,-disopropylphosphoramidite are added to the reaction vessel again using a dried, argon flushed gas tight syringe, and gently agitated for 1 hour.

The contents of reaction vessel are transferred to a sintered glass funnel and the resin washed with a generous volume of solvent. 20 eq. of t-butyl peroxide in DMF are added to the resin and left to stand for 30 mins. The resin is washed and dried in a normal manner. Standard methods are used for cleavage.

Peptides synthesized in these manners may then be aliquoted in predetermined amounts and stored in conventional manners, such as in aqueous solutions or, even more preferably, in a powder or lyophilized state pending use.

In general, due to the relative stability of peptides, they may be readily stored in sterile aqueous solutions for fairly long periods of time if desired, e.g., up to six months or more, in virtually any aqueous solution without appreciable degradation or loss of immunogenic activity.

However, where extended aqueous storage is contemplated, it will generally be desirable to include agents including buffers such as Tris-HCl or phosphate buffers to maintain a pH of 7.0 to 7.5. Moreover, it may be desirable to include agents which will inhibit microbial growth, such as sodium azide or merthiolate. For extended storage in an aqueous state, it will be desirable to store the solutions at 4° C., or more preferably, frozen.

Of course, where the peptide(s) are stored in a lyophilized or powdered state, they may be stored virtually indefinitely, e.g., in metered aliquots that may be rehydrated with a predetermined amount of water (preferably distilled) or buffer prior to use.

Peptides longer than about 50 or so amino acids are preferably provided by a plasmid or viral expression system, as described herein.

5. Gene Therapy

Vectors that encode and express one or more tyrosine-containing peptides, or even normal Bcr, form further aspects of the present invention. Recombinant expression can be used to provide any tyrosine-containing peptide, as desired, but it will generally be preferred for providing peptides of intermediate or longer length.

Exemplary vectors are those expressing the Bcr-159 fragment (SEQ ID NO:5) or normal Bcr, as may be used to inhibit the Bcr-Abl kinase to neutralize the malignant form of Bcr-Abl directly. Further vectors are those expressing a polypeptide of SEQ ID NO:28.

Suitable Bcr-Abl DNA sequences for use in the present invention will be known to those of skill in the art. Further, given the standard knowledge in the art and the information presented herein, e.g., in Table 1, the synthesis or generation, e.g., by cloning or PCR, of any given DNA fragment that encodes a desired peptide sequence will be straightforward.

A first approach for gene therapy in the context of the present invention is to transfect DNA containing the gene of interest into cells, e.g., by permeabilizing the cell membrane either chemically or physically. This approach is generally limited to cells that can be temporarily removed from the body and can tolerate the cytotoxicity of the treatment (i.e. lymphocytes). However, it is very suitable for use with the present invention.

Liposomes or protein conjugates formed with certain lipids and amphophilic peptides can be used for transfection (Stewart et al., 1992; Torchilin et al., 1992; Zhu et al., 1993), as described herein. The use of naked DNA and plasmids to directly transfer genetic material into a cell is also possible (Wolfe et al., 1990).

A second approach capitalizes on the natural ability of viruses to enter cells, bringing their own genetic material with them. Retroviruses have promise as gene delivery vectors due to their ability to integrate their genes into the host genome, transferring a large amount of foreign genetic material, infecting a broad spectrum of species and cell types and of being packaged in special cell-lines (Miller, 1992).

A third method uses other viruses, such as adenovirus; herpes simplex viruses (HSV), U.S. Pat. No. 5,288,641, incorporated herein by reference; cytomegalovirus (CMV); and adeno-associated virus (AAV), such as those described by Kotin (1994) and in U.S. Pat. No. 5,139,941, incorporated herein by reference; which are engineered to serve as vectors for gene transfer. Many viruses have been demonstrated to successfully effect gene expression. The term "herpes virus" is used in this context to particularly refer to herpes simplex virus (HSV), Epstein-Barr Virus (EBV), cytomegalovirus (CMV) and pseudorabies virus (PRV).

In using a retrovirus approach, the desired BCR coding sequences are inserted into a retroviral vector; this vector is transfected into a packaging cell line that generates an amphotropic host range defective virus. The virus is used to infect stem cells from the bone marrow of autotransplant patients.

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new binding specificity. Engineering viral vectors targeted to tumor cell markers is now straightforward in light of the Kasahara et al. (1994) work.

Of course, in using any viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

(a) Adenovirus

Human adenoviruses are a further means for introducing nucleic acid expression vectors into tissue. Adenoviruses are double-stranded DNA tumor viruses with genome sizes of approximately 36 kb. As a model system for eukaryotic gene expression, adenoviruses have been widely studied and well characterized, which makes them an attractive system for development of adenovirus as a gene transfer system. This group of viruses is easy to grow and manipulate, and they exhibit a broad host range in vitro and in vivo. In lytically infected cells, adenoviruses are capable of shutting off host protein synthesis, directing cellular machineries to synthesize large quantities of viral proteins, and producing copious amounts of virus.

In general, adenovirus gene transfer systems are based upon recombinant, engineered adenovirus which is rendered replication-incompetent by deletion of a portion of its genome, such as E1, and yet still retains its competency for infection. Relatively large foreign proteins can be expressed when additional deletions are made in the adenovirus genome. For example, adenoviruses deleted in both E1 and E3 regions are capable of carrying up to 10 kb of foreign DNA and can be grown to high titers. Persistent expression of transgenes follows adenoviral infection.

Particular advantages of an adenovirus system for delivering foreign genes and their protein products to a cell include (i) the ability to substitute relatively large pieces of viral DNA with foreign DNA; (ii) the structural stability of recombinant adenoviruses; (iii) the safety of adenoviral administration to humans; (iv) lack of any known association of adenoviral infection with cancer or malignancies; (v) the ability to obtain high titers of the recombinant virus; and (vi) the high infectivity of adenovirus.

Further advantages of adenovirus vectors over retroviruses include the higher levels of gene expression. Additionally, adenovirus replication is independent of host gene replication, unlike retroviral sequences. Because adenovirus transforming genes in the E1 region can be readily deleted and still provide efficient expression vectors, oncogenic risk from adenovirus vectors is thought to be negligible.

Human subjects testing positive for the Philadelphia chromosome and for whom the medical indication for adenovirus-mediated gene transfer has been established are tested for the presence of antibodies directed against adenovirus. If antibodies are present and the patient has a history of allergy to either pharmacological or naturally occurring substances, application of a test dose of on the order of $10^3$ to $10^6$ recombinant adenovirus under close clinical observation is indicated.

Recombinant adenovirus providing BCR peptides or fusion peptides of the present invention is prepared and purified by any method that is acceptable to the Food and Drug Administration for administration to human subjects, including, but not limited to cesium chloride density gradient centrifugation, and subsequently tested for efficacy and purity. Virus is administered to patients by means of administration to bone marrow in any pharmacologically acceptable solution, either as a bolus or as an infusion over a period of time. Generally speaking, it is believed that the effective number of functional virus particles to be administered would range from $5 \times 10^{10}$ to $5 \times 10^{12}$.

Patients would remain hospitalized for at least 48 hr to monitor acute and delayed adverse reactions. Bone marrow levels of Philadelphia chromosome-positive cells may be monitored. Adjustments to the treatment may include adenovirus constructs that use different promoters or a change in the number of pfu administered.

6. Pharmaceutical Formulations (a) Liposomes

The peptides of the present invention may be associated with liposomes. These liposome preparations may be used both in vivo and in ex vivo protocols, e.g., in bone marrow purging.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 µm. Sonication of MLVs results in the formation of small unilamellar vesicles (SUVs) with diameters in the range of 200 to 500 Å, containing an aqueous solution in the core.

Liposomes bear many resemblances to cellular membranes and are contemplated for use in connection with the present invention as carriers for the BCR peptides. They are widely suitable as both water- and lipid-soluble substances and can be entrapped, i.e., in the aqueous spaces and within the bilayer itself, respectively. It is possible that drug-bearing liposomes may even be employed for site-specific delivery of active agents by selectively modifying the liposomal formulation.

The formation and use of liposomes is generally known to those of skill in the art. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

In addition to temperature, exposure to proteins can alter the permeability of liposomes. Certain soluble proteins such as cytochrome c bind, deform and penetrate the bilayer, thereby causing changes in permeability. Cholesterol inhibits this penetration of proteins, apparently by packing the phospholipids more tightly.

The ability to trap solutes varies between different types of liposomes. For example, MLVs are moderately efficient at trapping solutes, but SUVs are extremely inefficient. SUVs offer the advantage of homogeneity and reproducibility in size distribution, however, and a compromise between size and trapping efficiency is offered by large unilamellar vesicles (LUVs). These are prepared by ether evaporation and are three to four times more efficient at solute entrapment than MLVs.

In addition to liposome characteristics, an important determinant in entrapping compounds is the physicochemical property of the compound itself. Polar compounds are trapped in the aqueous spaces and nonpolar compounds bind to the lipid bilayer of the vesicle. Polar compounds are released through permeation or when the bilayer is broken, but nonpolar compounds remain affiliated with the bilayer unless it is disrupted by temperature or exposure to lipoproteins. Both types show maximum efflux rates at the phase transition temperature.

Liposomes interact with cells via four different mechanisms: endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

The fate and disposition of intravenously injected liposomes depend on their physical properties, such as size, fluidity and surface charge. They may persist in tissues for hours or days, depending on their composition, and half lives in the blood range from minutes to several hours. Larger liposomes, such as MLVs and LUVs, are taken up rapidly by phagocytic cells of the reticuloendothelial system, but physiology of the circulatory system restrains the exit of such large species at most sites. They can exit only in places where large openings or pores exist in the capillary endothelium, such as the sinusoids of the liver or spleen. Thus, these organs are the predominate site of uptake. On the other hand, SUVs show a broader tissue distribution but still are sequestered highly in the liver and spleen. In general, this in vivo behavior limits the potential targeting of liposomes to only those organs and tissues accessible to their large size. These include the blood, liver, spleen, bone marrow and lymphoid organs.

Targeting is generally not a limitation in terms of the present invention. However, should specific targeting be desired, methods are available for this to be accomplished. Antibodies may be used to bind to the liposome surface and to direct the antibody and its drug contents to specific antigenic receptors located on a particular cell-type surface. Carbohydrate determinants (glycoprotein or glycolipid cell-surface components that play a role in cell-cell recognition, interaction and adhesion) may also be used as recognition sites as they have potential in directing liposomes to particular cell types.

Mostly, it is contemplated that intravenous injection of liposomal preparations be used, but other routes of administration are also conceivable. Of course, with ex vivo protocols, administration is straightforward.

(b) Injectables

Compositions of the present invention comprise an effective amount of the tyrosine-containing peptide or peptides, liposomes, or viral vectors, dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The active compounds will generally be formulated for parenteral administration, e.g., formulated for injection via the intravenous, intramuscular, sub-cutaneous, intralesional, or even intraperitoneal routes. The preparation of an aqueous composition that contains a tyrosine-containing peptide or expression vector, as an active component or ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

A tyrosine-based peptide can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus ny additional desired ingredient from a previously sterile-filtered solution thereof.

The preparation of more, or highly, concentrated solutions for intramuscular injection is also contemplated. In this regard, the use of DMSO as solvent is preferred as this will result in extremely rapid penetration, delivering high concentrations of the active peptides or agents to a small area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g., tablets or other solids for oral administration; time release capsules; and any other form currently used, even including cremes, lotions, mouthwashes, inhalents, suppositories and the like.

7. Bone Marrow Purging

The present invention provides a most practical system for purging human bone marrow samples of leukemic patients. The general protocol for standard human bone marrow transplantion has already been established in the medical arts and is thus an available technique to those of ordinary skill in the art.

In the typical clinical management of a patient with leukemia, the patient is given chemotherapy (for example, Daunomycin, Ara-C, GMCSF). The chemotherapy treatment will typically generate cytogenetic remissions in 50% of the treated patients. Cytogenetic remission is defined as a reduction in the ratio of leukemia cells (Philadelphia chromosome-positive) to normal cells (Philadelphia chromosome-negative) from about 10,000/1 to 1/1.

The bone marrow of these patients is then subjected to separations based on the immunophenotype of the patient.

The inventors will define a DR negative lineage CD33 negative, DC34 positive phenotype (i.e., through fractionation of a DR negative CD34 cell line). This separation, based on immunophenotype, will, in most cases, reduce the ratio of leukemic to normal cells by another 2 logs (100×).

By then employing the described BCR-peptide treatment methods to bone marrow samples of the patient described herein, the ratio of leukemia cells (Philadelphia chromosome-positive) to normal cells may advantageously be expected to be reduced by still another 2 or even 3 logs. Generally, the bone marrow sample is exposed to about 10 $\mu$M of the tyrosine-containing BCR peptide or peptides.

The treated bone marrow is then transplanted back into the patient. This method therefore provides a highly selective method of treating leukemia in the patient without damaging or inhibiting normal cells of the patient.

While the present technique may not accommodate the entire population of patients afflicted with CML (because of the small percentage of CML patients eligible for allogenic bone marrow transplantation due to advanced age (i.e., a chronological age of greater than 50 at most medical centers) or availability of donors (25% of 30% of patients with CML have donors)), the present invention nonetheless provides a marked improvement in the overall effectiveness of bone marrow transplant procedures for treating leukemic patients compared to those with non-pre-treated bone marrow samples currently employed.

8. Peptides as Standards for Radioiodination

The Bcr/Abl peptides of the present invention having a tyrosine residue are also provided as standards for radioiodination. The tyrosine-containing peptides are at least about 3–4 amino acids long, preferably 10–12 amino acids long, and may be 14–16 or 20–25 amino acids long or even longer. These peptides are useful as controls for testing the efficiency of radioiodinating a test peptide or protein by comparing the specific radioactivities of the test radioiodinated peptide or protein to a radioiodinated peptide of the present invention.

Radioiodination of proteins is discussed in Bailey 1984, incorporated by reference herein. Radioiodinated molecules are of major importance in studies of intermediary metabolism, in determinations of agonist and antagonist binding to receptors, and in quantitative measurements of physiologically active molecules in tissues and biological fluids, for example. In those studies, it is necessary to measure very low concentrations of the particular substance, and that requires a radioactively labeled tracer molecule of high specific radioactivity. Such tracers, particularly in the case of peptides and proteins, are conveniently produced by radioiodination.

Two $\tau$-emitting radioisotopes of iodine are widely available, $^{125}$I and $^{131}$I. As $\tau$-emitters they can be counted directly in a $\tau$ counter without the need for sample preparation, which is in direct contrast to $\beta$-emitting radionuclides, such as $^3$H and $^{14}$C. The counting efficiency for $^{125}$I, is approximately twice that for $^{131}$I. Thus, in most circumstances, $^{125}$I is the radionuclide of choice for radioiodination.

Several different methods of radioiodination of proteins have been developed (Bolton 1977; incorporated herein by reference). They differ primarily in the nature of the oxidizing agent for converting $^{125}$I$^-$ into the reactive species $^{125}$I$_2$ or $^{125}$I$^+$. Those reactive species substitute into tyrosine residues of the protein, but substitution into other residues, such as histidine, cysteine, and tryptophan, can occur.

The chloramine-T method, developed by Hunter and Greenwood (1962; incorporated herein by reference), is a commonly used technique for protein or peptide radioiodination. It is a straightforward method in which the radioactive iodide is oxidized by chloramine-T in aqueous solution. The oxidation is stopped after a brief period of time by addition of excess reductant. Some proteins or peptides are denatured under the relatively strong oxidizing conditions, and so other methods of radioiodination that employ more gentle conditions have been devised, e.g., the lactoperoxidase method (Marchalonis, 1969).

Materials:
1. Na$^{125}$I: 1 mCi, concentration 100 mCi/mL.
2. Buffer A: 0.5M sodium phosphate buffer, pH 7.4.
3. Buffer B: 0.05M sodium phosphate buffer, pH 7.4.
4. Buffer C: 0.01M sodium phosphate buffer containing 1M sodium chloride, 01% bovine serum albumin, and 1% potassium iodide, final pH 7.4.
5. Chloramine-T solution: A 2 mg/mL solution in buffer B is made just prior to use.
6. Reductant: A 1 mg/mL solution of sodium metabisulfite in buffer C is made just prior to use.
7. Protein or peptide to be iodinated: A 0.5–2.5 mg/mL solution is made in buffer B.

Method:
1. Into a small plastic test tube (1×5.5 cm) are added successively the protein or peptide to be iodinated (10 $\mu$g), radioactive iodide (5 $\mu$L), buffer A (50 $\mu$L), and chloramine-T solution (25 $\mu$L).
2. After mixing by gentle shaking, the solution is allowed to stand for 30 s to allow radioiodination to take place.
3. Sodium metabisulfite solution (500 $\mu$L) is added to stop the radioiodination and the resultant solution is mixed. It is then ready for purification.

Purification of Radioiodinated Protein or Peptide:

For most uses of radioiodinated proteins or peptides, it is desirable to have the labeled species as pure as possible with the constraints, however, that the purification is achieved as rapidly as possible. For that purpose the most widely used of all separation techniques is gel filtration. Various types of Sephadex resin can be employed, e.g., G-50, G-75 and G-100 depending on the differences in sizes of the molecules present in the mixture.

Typically the mixture is applied to a column (1×25 cm) of Sephadex resin and is eluted with 0.05M sodium phosphate buffer of pH 7.4 containing 0.15M sodium chloride and 0.1% bovine serum albumin. Fractions (0.5–1.0 mL) are collected in plastic tubes and aliquots (10 $\mu$L) are counted. Using those results, an elution profile is drawn.

Several parameters are used to assess the quality of the labeled protein or peptide. The specific radioactivity of the protein is the amount of radioactivity incorporated per unit mass of protein or peptide. It can be calculated in terms of the total radioactivity employed, the amount of the iodination mixture transferred to the gel filtration column, and the amount of radioactivity present in the labeled protein or peptide, in the damaged components, and in the residual radioiodine.

However, in practice, the calculation does not usually take into account damaged and undamaged protein. The specific activity is thus calculated from the yield of the radioiodination procedure, the amount of radioiodide and the amount of protein or peptide used, assuming that there are not significant losses of those two reactants. The yield of the reaction is simply the percentage incorporation of the radionuclide into the protein.

The nature of the materials giving rise to elution peaks from a chromatography column can be checked by employing a specific antiserum to the protein or peptide being radioiodinated. Aliquots (10 µL) of different fractions making up the two peaks are diluted so that each gives the same number of counts (e.g., 5000–10,000 counts/min) per 100 µL). Those samples are incubated with an excess of the antiserum. Only samples containing immunoreactive protein will react with the antiserum. The amount of the radioactive protein associated with the antibody molecules can then be measured by radioimmunoassay.

Having identified the peak or peaks containing the radioiodinated protein or peptide, the yield of the radioiodination can be calculated in terms of the ratio of the total counts associated with the protein or peptide peak to the sum of the total counts associated with the iodide peak.

It is important that the radioiodinated protein or peptide should as far as possible have the same properties as the unlabeled species. Thus the behavior of both molecules can be checked on electrophoresis or ion-exchange chromatography. The ability of the two species to bind to specific antibodies can be assessed by radioimmunoassay.

To store the labelled protein or peptide, immediately after purification, split the sample into small aliquots and then rapidly freeze and store at −20° C. Alternatively, the aliquots can be freeze-dried. Each aliquot should be melted and used only once. Radioiodinated proteins or peptides differ markedly in their stability. Some can be stored for several weeks (though it must be borne in mind that the half-life of $^{125}I$ is about 60 d), whereas others can only be kept for several days. If necessary, the labeled protein can be repurified by gel filtration or ion-exchange chromatography prior to use.

The pH optimum for iodination of tyrosine residues of a protein by the chloramine-T method is about pH 7.4. Lower yields of iodinated protein are obtained at pH values below about 6.5 and above about 8.5. Indeed, above pH 8.5, the iodination of histidine residues appears to be favored.

The total volume of the chloramine-T reaction mix should be as low as practically possible to achieve a rapid and efficient incorporation of the radioactive iodine into the protein or peptide. Because of the small volumes of reactants that are employed it is essential to ensure adequate mixing at the outset of the reaction. Inadequate mixing is one of the commonest reasons for a poor yield of radioiodinated protein by this procedure.

If the protein or peptide has been seriously damaged by the use of 50 µg of chloramine-T, it may be worthwhile repeating the radioiodination using much less oxidant (10 µg or less). The minimum amount of chloramine-T that can be used will depend, among other factors, on the nature and amount of protein to be iodinated.

It is normal to carry out the chloramine-T method at room temperature. However, if the protein is especially labile, it may be beneficial to run the procedure at a low temperature.

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLE I

Materials and Methods

Cell Line K562: Source; American Type Culture Collection (ATCC), Rockville, Md. Isolation; Established by Lozzio and Lozzio (1975) from the pleural effusions of a female in blast crisis CML. This cell line contains multiple copies of the $Ph^1$ with breakpoint on chromosome 22 within the Mbcr (b3/a2 translocation). Cells are grown at 37° C. and 5% $CO_2$ in RPMI 1640 growth medium supplemented with 10% fetal calf serum (Gibco Laboratories, Grand Island, N.Y.).

Cell Lines, SUTP-B13 and SUTP-B15: Source: Cell lines were obtained from Dr. Steve D. Smith, Department of Pediatrics, University of Chicago. Isolation: Cell lines were obtained from the first and second bone marrow relapse samples, respectively, of an 8-yr-old male admitted to Children's Hospital at Stanford, Calif. in 1983 (Naumovski et al., 1988).

Cell lines contain the $Ph^1$ chromosome with ALL specific breakpoint on chromosome 22 with in the mbcr. However, these cell lines differ in the expression of some cell surface antigens rendering them related but unique.

Cells are grown at 37° C. and 5% $CO_2$ in RPMI 1640 growth medium supplemented with 20% fetal calf serum (Gibco Laboratories, Grand Island, N.Y.). Initial culture conditions require that these cells be grown in a six-well culture plate at optimum cell density, $0.5 \times 10^6$ ml, for 10–14 days. During this period, the cells must be counted daily to insure against overgrowth of the culture and the media must be replenished.

The cells are then diluted to appropriate volumes with fresh culture media and the suspension aliquoted into the wells at approximately 6 mls of culture per well. After a sufficient number of wells have been seeded and culture remains healthy, the stocks are plated into T75 or T150 culture flasks for general growth.

However, these cells are extremely fragile and appear to undergo a form of apoptosis or programmed cell death if the culture becomes either too dense or too dilute from optimal cell concentrations. This condition is immediately recognizable as the culture flask appears to be bacterially contaminated with small particles of cellular debris.

This condition can be remedied by gentle centrifugation of the cell culture through 2 mls of fetal calf serum. The resulting cell pellet, free of cellular debris, is resuspended at appropriated cell concentrations in fresh culture media. Again, a careful monitoring on the status of this cell culture is required to insure proper cell viability.

Cell Line SMS-SB: Source: R. Peter Gale, Los Angeles, Calif. Cells were isolated from the peripheral blood of a 17-yr-old female suffering from a relapse of lymphoblastic lymphoma. The cells synthesize but do not secrete u-chains and except for the lack of u-chain secretion, the phenotype of SMS-SB cells is the same as the major population of marrow pre-B cells (see Smith et al., 1981). Cells are cultured at 37° C. in 5% $CO_2$ in RPMI 1640 media supplemented with 10% fetal calf serum (Gibco Laboratories, Grand Island, N.Y.).

Cell Line HL60: Source: American Type Culture Collection (ATCC), Rockville, Md. Isolation: Peripheral blood leukocytes were obtained from an adult female with acute promyelocytic leukemia. Most of the cells stained by the Wright-Giemsa procedure were myeloblasts and promyelocytes with azurophilic granules, but more mature myeloid cells were also seen (Collins et al., 1977). Cells are grown at 37° C. and 5% $CO_2$ in RPMI 1640 growth medium supplemented with 10% fetal calf serum (Gibco Laboratories, Grand Island, N.Y.).

Cell Line M3.16: Source: The cells were obtained from Dr. Pierre Laneuville at Hospital Royal Victoria Hospital in Montreal, Canada. Isolation: The IL3/GM-CSF-dependent cell line, designated M-07E cells was derived from an early passage of the primary culture from a patient with acute megakaryoblastic leukemia. M3.16 cell line was derived from M-07E cells that contain a retroviral vector that expresses P210 BCR-ABL. M3.16 cells grow without added IL3/GM-CSF in a DMEM/10%FCS (Sirard et al., 1994). Cells are grown at 37° C. and 5% $CO_2$ in DMEM supplemented with 10% fetal calf serum (Gibco Laboratories, Grand Island, N.Y.).

Cell Line COS1: Source: ATCC (Rockville, Md.). Isolation: COS1 is a fibroblast-like cell line established from simian kidney cells (CV1) that were transformed by an origin-defective mutant of SV40, which codes for wild-type T antigen. Cells were cultured in 37° C. and 5% $CO_2$ in DMEM supplemented with 10% fetal calf serum (Gibco Laboratories, Grand Island, N.Y.).

Plasmid Psp65 BCR: This plasmid was obtained from Dr. John Groffen (Childrens Hospital of Los Angeles, Calif.). It is used for in vitro transcription (using SP6 polymerase) and translation.

Plasmid Psp65 c-ABL(1b) and Psp65/P210 BCR-ABL: These plasmids contain full length c-ABL(1b) or P210 BCR-ABL cDNAs, respectively. They were obtained from Dr. Eli Canaani (Weissman Institute, Israel) and can be used for in vitro transcription (using SP6 polymerase) and translation.

Plasmid PSG5BCR: The original human full length BCR cDNAs were obtained from Dr. John Groffen (Children's Hospital of Los Angeles, Calif.). The B3 clone that has the complete coding region of BCR plus about 150 bp 5' untranslated region was cloned into the EcoRI site of psp65 vector.

The original human full length p210 BCR-ABL cDNA was obtained from Dr. Eli Canaani (The Weizmann Institute of Science, Israel). The p210 BCR-ABL construct, having the complete coding region plus about 10 bp 5' untranslated region, was positioned in the EcoRI/HindIII sites of psp65 vector. In order to reduce the 5' untranslated sequence of BCR for better expression, the EcoRI-XhoI fragment from p210 BCR-ABL was used to replace the EcoRI-XhoI fragment of the B3 clone.

The newly constructed human full length BCR cDNAs containing about 10 bp 5' untranslated sequences were released from the psp65 vector by EcoRI digestion and subsequently inserted into the EcoRI site of an eucaryotic expression vector pSG5 (Stratagene, La Jolla, Calif.). The pSG5 vector contains the early SV40 promotor to facilitate in vivo expression in cells also expressing the T antigen.

Plasmid PSG5BCR-ABL: The human full length p210 BCR-ABL was released from the psp65 vector by EcoRI complete digestion and SacI partial digestion. The full length cDNA was then used to replace the EcoRI-SacI fragment of BCR in the pSG5 vector. This construct contains a large C-terminal BCR sequence after the stop codon of p210 BCR-ABL. Almost all of this C-terminal portion of the BCR sequence was removed by releasing a BamHI partial digested fragment.

Plasmid PSG5ABL(1b): The human full length p145 c-Abl (1b) cDNA was obtained from Dr. Eli Canaani (The Weizmann Institute of Science, Israel). The c-Abl(1b) insert was released from psp65 vector by StuI (blunt end) partial digestion followed by EcoRI complete digestion. The EcoRI-StuI fragment was then ligated with PSG5 linearized by EcoRI and BalI (blunt end) digestion.

Figure 7:
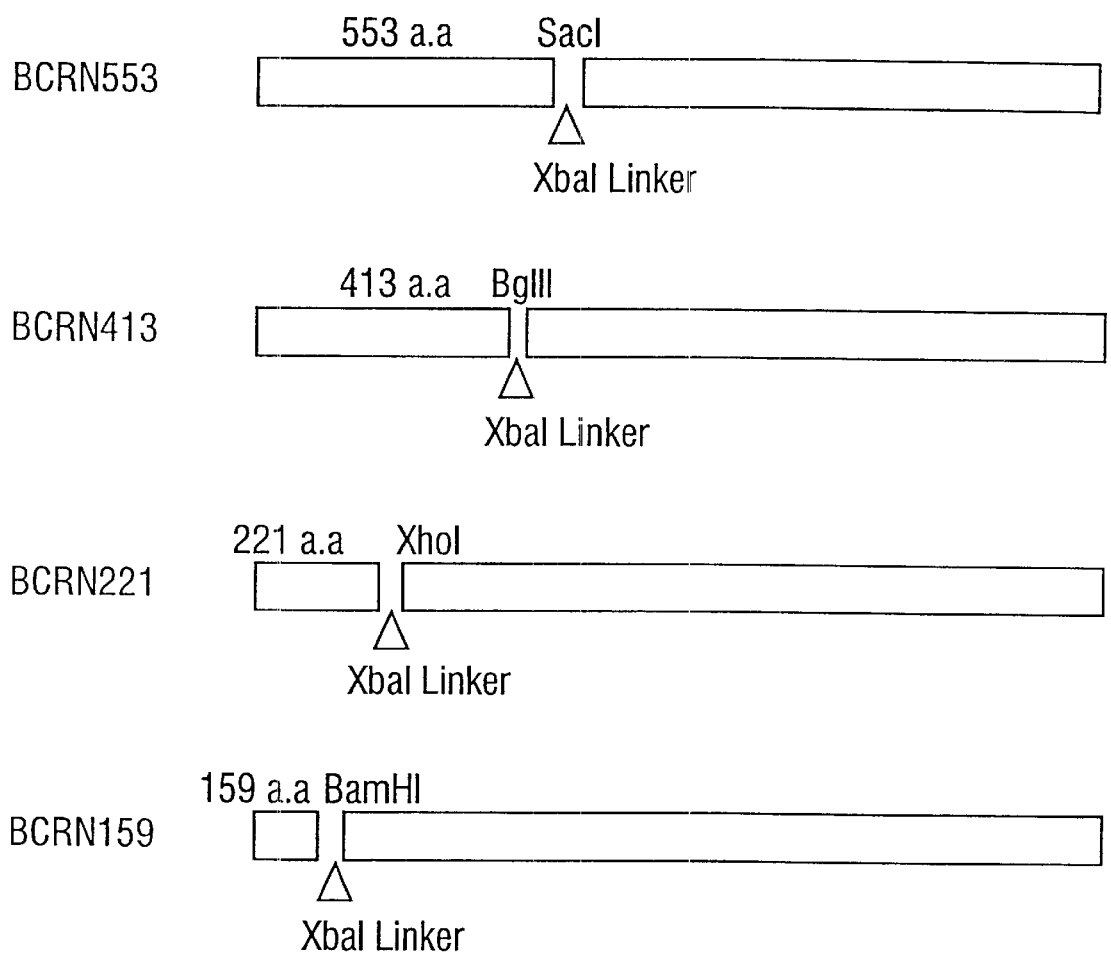
FIG. 7 provides a schematic diagram of the BCR deletion mutants.
Figure 8A:
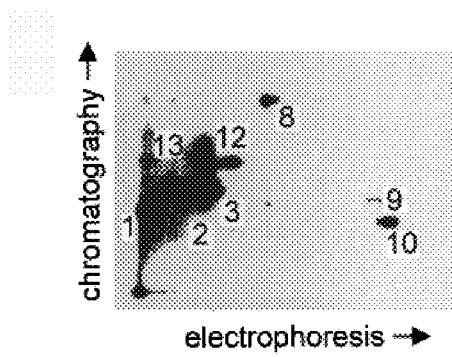
FIG. 8A, FIG. 8B, FIG. 8C and FIG. 8D show two-D tryptic maps of in vitro phosphorylated Bcr-Abl proteins. Mutant and wild type Bcr-Abl proteins were expressed in COS-1 cells as described. Bcr-Abl proteins were phosphorylated in vitro using anti-Abl(52–64) immune complexes, and mapped. The dashed circles identify peptides lacking in the mutant.
Figure 8B:
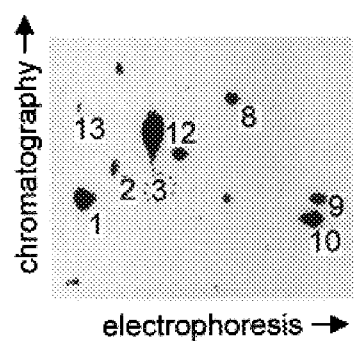
Figure 8C:
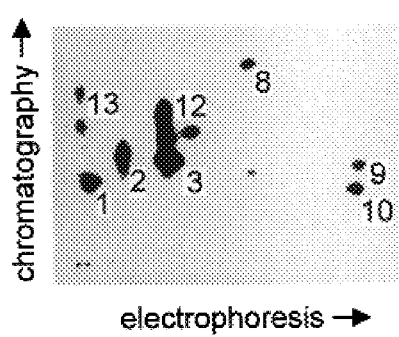
Figure 8D:
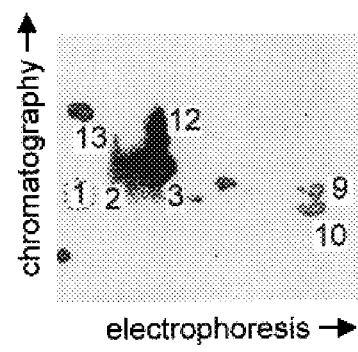

Plasmids PSG5BCRN553, PSG5BCRN413, PSG5BCRN221, PSG5BCRN159: These deletion mutants were obtained by inserting a XbaI linker containing stop codons at all three reading frames (CTAGTCTAGACTAG, SEQ ID NO:14, Stratagene, La Jolla, Calif.) into SacI, BglII, XhoI or BamHI site within the BCR first exon coding sequences, respectively (FIG. 7).

Mutations: p185 BCR-ABL and p160 BCR constructs with Tyr to Phe mutations at residues 177 and 360 of BCR were supplied by Dr. Groffen's group (Childrens Hospital of Los Angeles, Calif.). Other mutations were first made in the wild type BCR by the method described below. p210 BCR-ABL mutants were then obtained by exchanging XhoI/SacI fragments of wild type p210 BCR-ABL with the same fragment from the mutant p160 BCR.

The TRANSFORMER™ Site-Directed Mutagenesis Kit (CloneTech Laboratories, Palo Alto, Calif.) was used for generating Tyr to Phe mutants. The mutagenic primers used for mutating tyrosine residues within BCR first exon were obtained from Operon Technologies (Alameda, Calif.), and their sequences are listed below.

| Tyrosine residue | Mutagenic primer | |
|---|---|---|
| 276 | 5' CCCCTGGAGTTCCAGCCCTAC 3' | SEQ ID NO:15 |
| 283 | 5' CAGAGCATCTTCGTCGGGGGC 3' | SEQ ID NO:16 |
| 316 | 5' CGCAGGTCCTTCTCCCCCCGG 3' | SEQ ID NO:17 |
| 328 | 5' GGAGGCGGCTTTACCCCGGAC 3' | SEQ ID NO:18 |

These mutagenic primers are used to mutate tyrosine to phenylalanine. The selection primer (5' TGGTC-GACTCGCGACTCTTCC 3' (SEQ ID NO:19)) for mutagenesis on pSG5BCR constructs was used to eliminate a unique restriction site XbaI in the vector pSG5. All of the mutations were verified by direct sequencing of the mutagenized regions.

Immunokinase Assay: The immunokinase assays were performed as described by Campbell et al. (1990) with modifications. The cells are lysed by homogenizing the cell pellet in two different lysis buffers at 0° C. in a tight fitting Wheaton homogenizer (either 0.1% Triton-X100, 100 mM NaCl, 5 mM EDTA, 10 mM sodium phosphate, pH 7.2 or 1% Triton-X100, 100 mM NaCl, 0.5% sodium deoxycholate, 0.1% SDS, 5 mM EDTA, 10 mM sodium phosphate pH 7.2). Both buffers were supplemented with 30 mM sodium pyrophosphate, 100 KIU aprotinin, 1 mM benzamidine, 1 mM phenylmethylsulfonyl fluoride and 0.2 mM sodium vanadate.

The cell lysate was then clarified by centrifugation at 100,000×G for 30–60 minutes at 4° C. The clarified supernatant was collected and divided equally among the samples for immunoprecipitation.

Immunoprecipitation reactions were carried out utilizing 20–40 μl of the respective anti-peptide rabbit sera or 5 μl of monoclonal antibody at 0° C. for 1 hour. Blocked immunoprecipitations refer to those immunoprecipitation reactions performed with antisera that have been preincubated with excess cognate peptide to specifically block the anti-peptide antibodies.

The resulting antigen-antibody immunoprecipitates were collected with 30 μl of 50% protein A-Sepharose (Pharmacia, Uppsala, Sweden), pelleted and washed with RIPA buffer (0.1% Triton X-100, 0.05% SDS, 0.5% sodium deoxycholate, 100 mM NaCl in 10 mM phosphate buffer, pH 7.2), wash buffer (0.1% Triton X-100, 100 mM NaCl, in 10 mM phosphate buffer, pH 7.2) and finally with 50 mM Tris buffer, pH 7.2.

The immunoprecipitate pellet was suspended in 50 μl of kinase assay buffer (100 mM NaCl, 0.1% Triton X-100, 10 mM MnCl in 20 mM HEPES buffer pH 7.2) containing 0.02 mCi [gamma-$^{32}$P] adenosine triphosphate for 10 minutes at 0° C. The labeled pellets were washed once in RIPA buffer and then denatured by boiling in mercaptoethanol/sodium dodecyl sulfate (SDS) sample buffer (1% SDS, 10% 2-mercaptoethanol, 10% glycerol, 1 mM EDTA, in pH 8.0 Tris buffer).

The boiled supernatant was resolved by SDS polyacrylamide gel electrophoresis (PAGE) on a 6.5% polyacrylamide gel. The dried gel was exposed to X-ray film using enhancing screens.

Immunoblotting Assays: Cells were lysed in Laemmli sodium dodecyl sulfate (SDS) sample buffer containing 10% 2-mercaptoethanol. The lysates were boiled for 3 minutes and then clarified by centrifugation at 100,000×g for 1 hour at room temperature. The supernatant fluid was collected and allocated.

The samples were resolved by SDS polyacrylamide gel electrophoresis (PAGE). The gels were electroblotted onto Immobilon P membranes (Millipore Corp., Bedford, Mass.) at 4° C. in transfer buffer (192 mM glycine, 25 mM Tris-HCl, pH 7.5, and 1% methanol) for 4–5 hours at 1.2 amps.

Blots were blocked by washing in 1–3% bovine serum albumin (BSA) in washing buffer (1150 mM NaCl, 0.1% NONADET™ P40, 50 mM Tris-HCl, pH 7.5 or 0.01M Tris, pH 7.5, 0.1 M NaCl, 0.1% TWEEN™ 20) or 10% nonfat milk in washing buffer (20 mM Tris-HCl base, pH 7.6, 137 mm NaCl, 3.8 mM HCl and 0.1% TWEEN™ 20) for 1–2 hours at 37° C. The filters were then reacted with antibodies of appropriate dilution (1: 20,000 for 8E9; 1:1,000 for anti-peptide antibodies; 1:250 for anti-Grb2 antibody; 1:1,000–2,500 for anti-phosphotyrosine antibodies) in blocking buffer 2 hours at room temperature or overnight at 4° C.

The filters were washed in washing buffer and scored with $I^{125}$-protein A (Amersham Co., Arlington Hts., Ill.) directly for rabbit antibody or mixed with rabbit anti-mouse IgG for monoclonal antibody (1 μg/10uCi of $I^{125}$-protein A) for 1 hr at room temperature in blocking buffer. Filters were washed in washing buffer, air dried and exposed to X-ray film.

An alternative method is to incubate the filters with horseradish peroxidase coupled anti-rabbit or anti-mouse Ig and then react with ECL reagents (Amersham Co., Arlington Hts., Ill.) after washing with washing buffer. The signals are detected by exposing the filters to hyperfilm (Amersham).

Tryptic Peptide Mapping of Phosphopeptides: $^{32}$P labeled proteins from in vitro kinase assays were resolved by electrophoresis on a SDS-6.5% PAGE gel. After electrophoresis, the gel was dried and autoradiographed with Kodak RP-1 X-ray film.

The $^{32}$P-labeled proteins were excised from the dried gel using the autoradiograph as a template. The blocking paper was scraped from the dried gel bands that were cut into small pieces and allowed to swell in a volume of elution buffer (0.05M $NH_4CO_3$, pH 8.5, 0.1% SDS, 0.5% 2-mercaptoethanol) corresponding to 2 ml buffer/1 cm$^2$ dried gel. The swollen gel pieces were further crushed with a glass stir rod.

The homogenate solution was boiled for 5 min and shaken overnight at 37° C. in a rotating wheel mixer to elute the labeled protein. The gel fragments were pelleted by centrifugation at 10,000×G for 10 min and the supernatant fluid carefully decanted and saved. A volume of fresh elution buffer at half the initial volume was then added to the gel fragments and this solution mixed at 37° C. for 4 hours as before. The gel fragments were pelleted again by centrifugation and the supernatant fluid decanted and saved.

The elution fractions were pooled and the combined eluate filtered through a 0.2 μ pore size millipore syringe filter. Bovine serum albumin (75 μg) was added to the eluate and mixed thoroughly. The BSA carrier and eluted $^{32}$P labeled protein was pelleted by making the solution 20% in trichloroacetic acid and incubating on ice for 4 hr.

The precipitated protein was pelleted by centrifugation, washed successively with ice-cold ethanol followed by an ice-cold solution of ethanol: ether (1:1) and the washed pellet centrifuged and air dried. The dried protein pellet was dissolved in 150 μl of chilled performic acid (30% $H_2O_2$ and 98% formic acid [1:9]) previously incubated for 1 hr at room temperature and incubated for 2 hr. at 0° C. The performic acid oxidizing solution was diluted with water and lyophilized on a speed vacuum dryer.

The resulting oxidized protein was digested with 30 μg of L-(1-tosylamido-2-phenyl) ethyl choromethyl ketonetreated trypsin (TPCK trypsin) in 0.5 ml of 0.05 M $NH_4HCO_3$ for 18 hr at room temperature. After 28 hr, an additional 20 μg of TPCK trypsin was added to the solution and the digestion continued for an additional 4 hrs.

The digested protein was diluted with water and lyophilized repeatedly until the $NH_4HCO_3$ salt was removed. The salt-free digest was dissolved in 15 μl of pH 2.1 electrophoresis buffer (distilled water, formic acid and acetic acid [90:2:8], pH 2.1) and applied as a spot to cellulose thin layer plate (Kodak #13255, Rochester, N.Y.) and electrophoresed for 1 hr at 1000V on a Hunter systems electrophoretic unit (HTLE 7000, CBS Scientific Co., Del Mar, Calif.).

Following electrophoresis, the plate was air dried and chromatographed in a thing-layer chromatography tank using a chromatography buffer consisting of N-butanol, acetic acid, water and pyridine [75:15:60:50]. The chromatography was run until the chromatography buffer had run the length of the plate or approximately four hours.

Phosphoamino acid analysis of tryptic peptides was accomplished by carefully removing the labeled tryptic peptide from the chromatography plate by scraping the cellulose matrix using the autoradiograph as a template. The labeled tryptic peptide was eluted from the cellulose matrix with 20% acetonitrile and treated with 6N HCl for 90 min at 11° C.

The clarified supernatant fluid was fractionated on thin layer plates (Chromogram without fluorescent indicator, Eastman Kodak, Rochester, N.Y.) in the presence of standard phosphoserine, phosphothreonine and phosphotyrosine. Radioactive phosphoamino acids were detected by autoradiography and the position of the standard phosphoamino acids detected by ninhydrin treatment.

V8 Protease Digestion: $^{32}$P labeled protein bands were cut out from a polyacrylamide gel and rehydrated with buffer A (0.125M Tris-HCl, pH 6.8, 0.1% SDS, and 1 mM EDTA). The gel slice was loaded into the wells of a 10.5% polyacrylamide gel and the wells were covered with buffer A containing 20% glycerol and 1 μg V8 protease. The gel was then run at 20 mA for 20 mins and stopped for 30 min. After that, electrophoresis continued.

EXAMPLE II

Bcr-Abl Peptides that Bind Adapter Proteins

The present inventors provide herein sets of adapter protein-Bcr peptide pairs that demonstrate binding affinity for each other. Therefore, these Bcr peptides, when provided in excess, would bind their respective binding sites on the adapter protein and prevent the adapter protein from interacting with endogenous Bcr-Abl. This interaction prevents the adapter protein from effecting its role in signal transduction, most particularly, in the Ras activation pathway.

The peptides may be provided in a phosphorylated form or a nonphosphorylated form. Phosphorylation is expected to occur within the cell; the form of the peptide that binds to the adaptor protein is the phosphorylated form.

The adapter protein-Bcr peptide pairs provided by the present invention include the following:
Bcr Peptide 164–181 (SEQ ID NO:8) and Adapter Protein Grb2/mSos1: The Bcr binding site within Bcr-Abl has been identified by the inventors. The following Bcr peptide sequence binds the SH2 domain of Grb2: GHGQPGADAEKPFpY$^{177}$VNVE (residues 164–181) (SEQ ID NO:8). The tyrosine residue at position 177 is phosphorylated by the Abl tyrosine kinase within Bcr-Abl.

Figure 2:
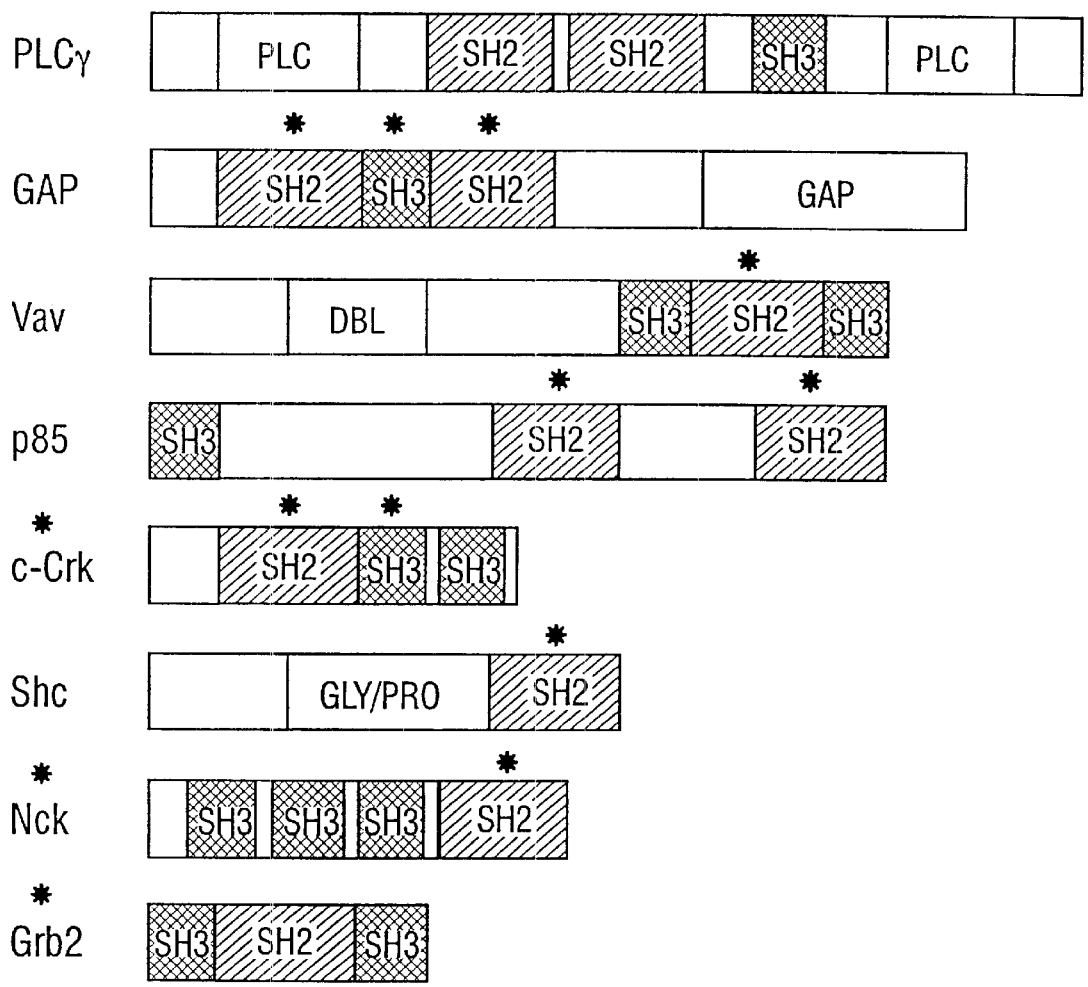
FIG. 2 provides a diagram of SH2/SH3 containing proteins involved in signal transduction.
Figure 3:
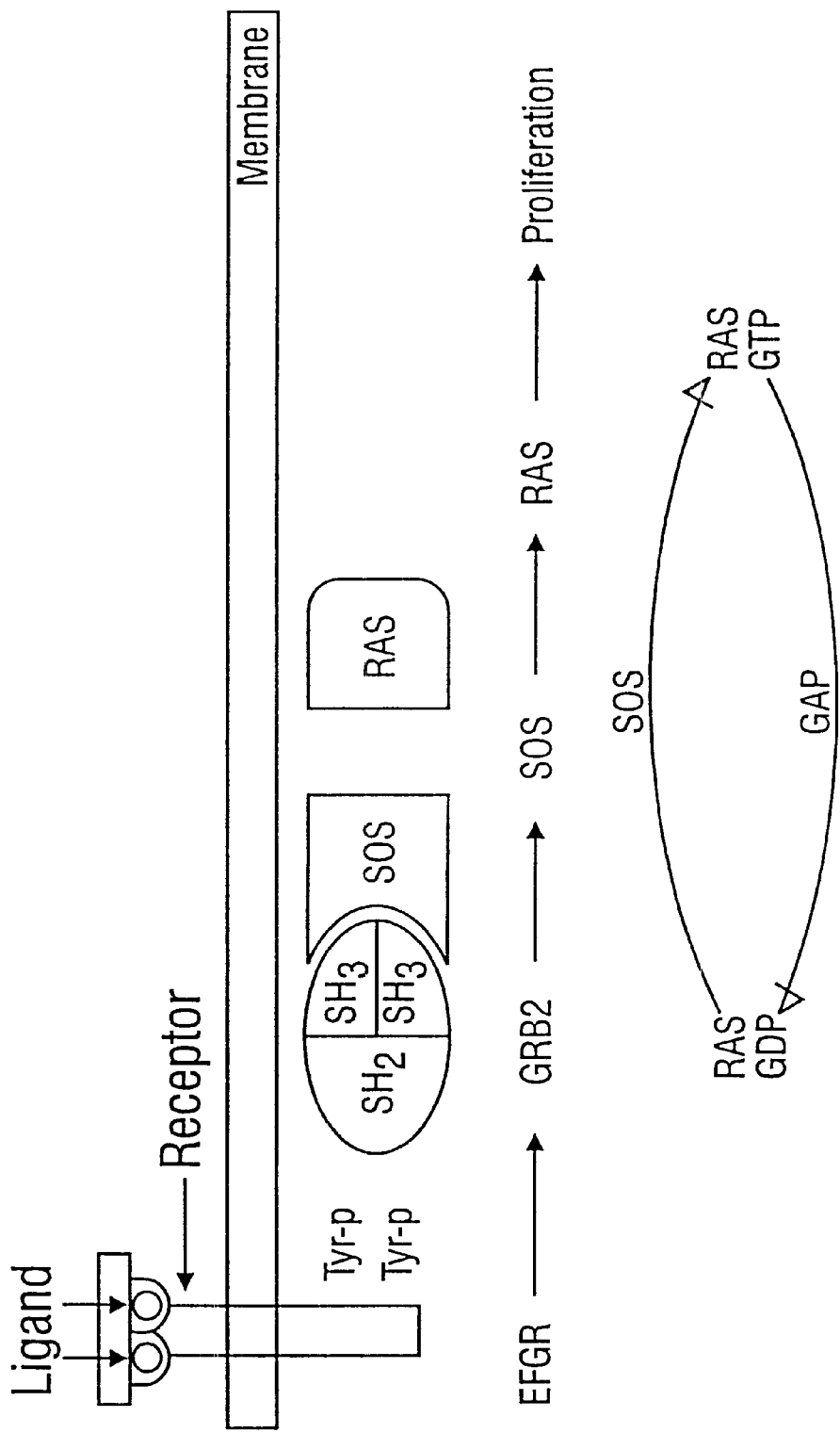
FIG. 3 outlines the activation of RAS by ligand receptor interaction.

In using a Bcr peptide containing pY$^{177}$ (SEQ ID NO:8), at least a 4-mer fragment thereof should be used, such as Bcr 176–180 (SEQ ID NO:24). An exemplary 13-mer is that corresponding to 168–180 Bcr (SEQ ID NO:27).
SH3 Domain of Abl, and Adapter Protein Shc: The SH3 domain of Abl contains a sequence that binds a proline-rich sequence of Shc.
Abl Peptide, and Adapter Protein Crkl: Crkl has a structure similar to Crk (the oncogene of V-Crk) (FIG.2) (Reichman et al., 1992; Ten Hoeve et al., 1993). Crk is an SH2/SH3-containing adaptor protein first discovered in an avian sarcoma virus (Reichman et al., 1992).

The Crkl protein product is a 38-kDa protein that is expressed in several cell types. This p38 is phosphorylated on tyrosine by Abl and Bcr/Abl and forms complexes in vivo with both Abl and Bcr/Abl. Crkl is tyrosine phosphorylated in cell lines expressing Bcr-Abl and in uncultured blood cells from patients that express the Bcr-Abl oncoprotein (Ten Hoeve et al., 1994). In addition, Crkl is capable of binding to mSos1 (Ten Hoeve et al., 1993).

Crk is phosphorylated on Y$^{221}$ by p145Abl. CRKL is proposed to be a biologically significant substrate for Bcr/Abl. One of the SH3 domains of CRKL binds to a proline-rich sequence within the Abl domain of Bcr-Abl. Peptides that mimic the Abl binding site on CRKL are therefore components of some embodiments of the present invention.
Bcr peptide 353–364 (SEQ ID NO:10) and an SH2 domain of an adapter protein. Another phosphotyrosine peptide within Bcr, VSPSPTTpY$^{360}$RMFR, SEQ ID NO:10, (residues 353–364) is also involved in binding of an adapter SH2-containing protein. This sequence surrounds tyrosine 360 of Bcr and Y$^{360}$ is also phosphorylated by the Abl tyrosine kinase within Bcr-Abl.

In using a Bcr peptide based upon 353–364 (SEQ ID NO:10), at least a 4-mer fragment thereof, such as Bcr 359–363 (SEQ ID NO:25), should be used. SEQ ID NO:22 is also useful.

A preferred peptide combination of the present invention is thus a set of peptides or a polypeptide having or comprising sequences from Bcr that include Y$^{177}$, Y$^{283}$ and Y$^{360}$, such as, for example, the peptide of SEQ ID NO:8, SEQ ID NO:11 and/or SEQ ID NO:10. A peptide including this set of binding sites should be at least 3 or 4 amino acids long, and preferably, about 10 or 12 or 15 amino acids long.

The tyrosine is about in the middle of the peptide since sequences to the carboxy-terminal side may be especially important for peptide binding, e.g., Asn 179 of the peptide that contains Y$^{177}$.

A polypeptide containing these sequences would have spacer amino acids to allow flexibility of the molecule for optimum binding.

The peptides of the present invention are preferably provided with amino-terminal acetyl groups so as to block the NH$_2$-terminal end from protease degradation and with an amide group at the carboxy terminal end.

Acetylation of the amino terminal end is accomplished using acetic anhydride following completion of the peptide. The acetylation is done on the nascent peptide bound to the resin during synthesis. The carboxy-terminal amide is accomplished by beginning the synthesis of the peptide onto derivatized resin (i.e., PAL Support; Millipore #GEN077483; Medford, Mass.). When the peptide is removed from this type of resin, it will have an amide group at its C-terminus.

EXAMPLE III

Bcr Peptides for Inhibition of Coiled Coil Interaction Between Bcr-Abl Molecules to Prevent Oligomerization Peptides comprising sequences from the N-terminal region of the Bcr portion of Bcr-Abl will inhibit a coiled-coil interaction between the Bcr portion of Bcr-Abl monomers, an interaction that is involved in formation of the tetrameric active form of Bcr-Abl. An excess of these N-terminal peptides will prevent tetramer formation and, thereby, prevent autophosphorylation of Bcr-Abl and its subsequent oncogenic functions.

SEQ ID NO:1 provides the amino acid sequence of the first exon of Bcr. The N-terminal peptides for use in the invention may comprise the sequence of amino acids 1–63 (SEQ ID NO:2), or amino acids 1–71 (SEQ ID NO:3), or amino acids 28–58 (SEQ ID NO:4), or amino acids 1–159 (SEQ ID NO:5), or amino acids 1–221 (SEQ ID NO:6) or amino acids 1–413 (SEQ ID NO:7) or equivalents thereof.

A fragment of the BCR gene encoding a 159 amino acid amino terminal fragment Bcr preferred in certain uses. Since normal Bcr protein forms a stable complex with Bcr-Abl, overexpression of Bcr 159 is expected to generate heterotetrameric structures composed of one molecule of Bcr-Abl and three molecules of Bcr 159. The tetramer should be inactive as a tyrosine kinase not only for autophosphorylation of Bcr-Abl but also inactive as a kinase to phosphorylate substrates such as Shc and Crkl.

EXAMPLE IV

Peptide 255–293 Mutation Studies

The inventors have conducted studies in which the amino terminal SH2 domain of Ras Gap was expressed as a fusion protein containing the glutathione S transferase protein (GST). These studies involve mixing GST-Gap SH2 with phosphotyrosine tryptic peptides of Bcr-Abl.

FIG. 8A, FIG. 8B, FIG. 8C and FIG. 8D show two-D tryptic maps of in vitro phosphorylated Bcr-Abl proteins. Bcr-Abl proteins were phosphorylated in vitro using anti-Abl(52–64) immune complexes, and mapped. The dashed circles identify peptides lacking in the mutant.

Figure 9A:
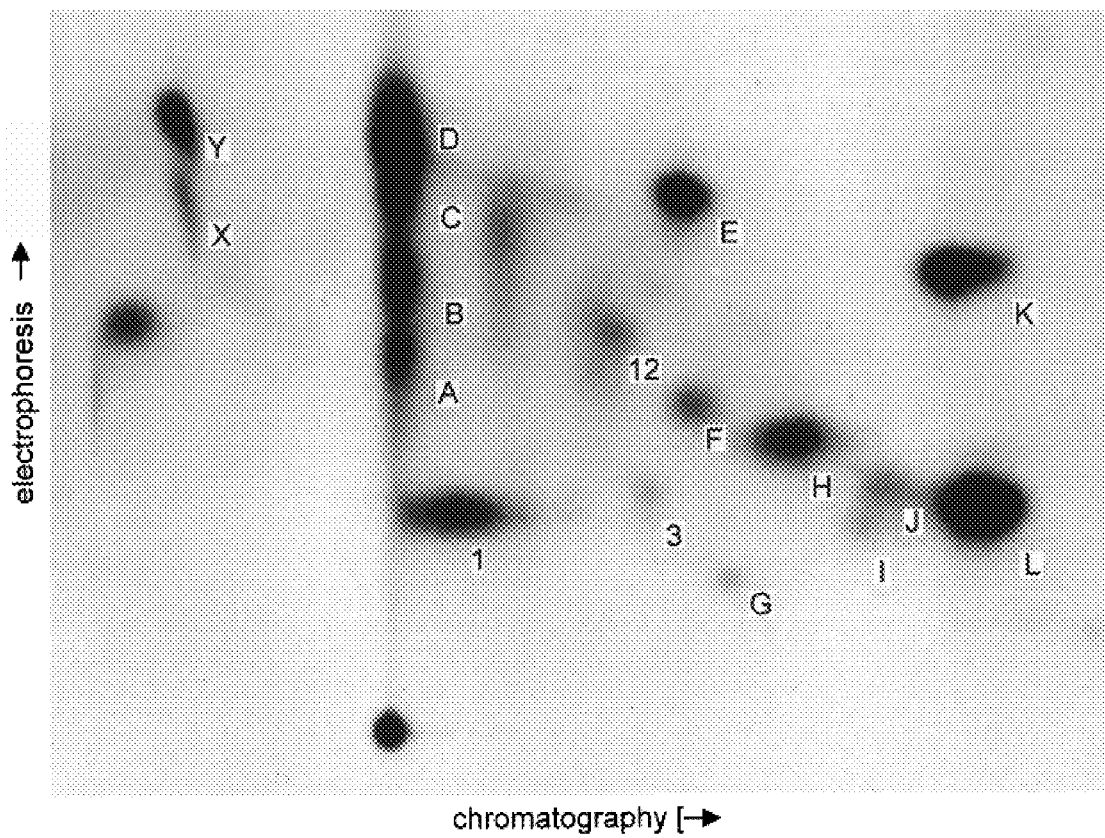
FIG. 9A and FIG. 9B show trypsin/V8 mapping of F283 and wild type p210 Bcr-Abl. The F283 mutant of p210 Bcr-Abl (FIG. 9B) expressed in COS-1 cells was compared to the map of p210 Bcr-Abl from K562 cells (FIG. 9A). In vitro labeling and mapping was performed. The dashed circles or Xs identify peptides lacking in the mutant.
Figure 9B:
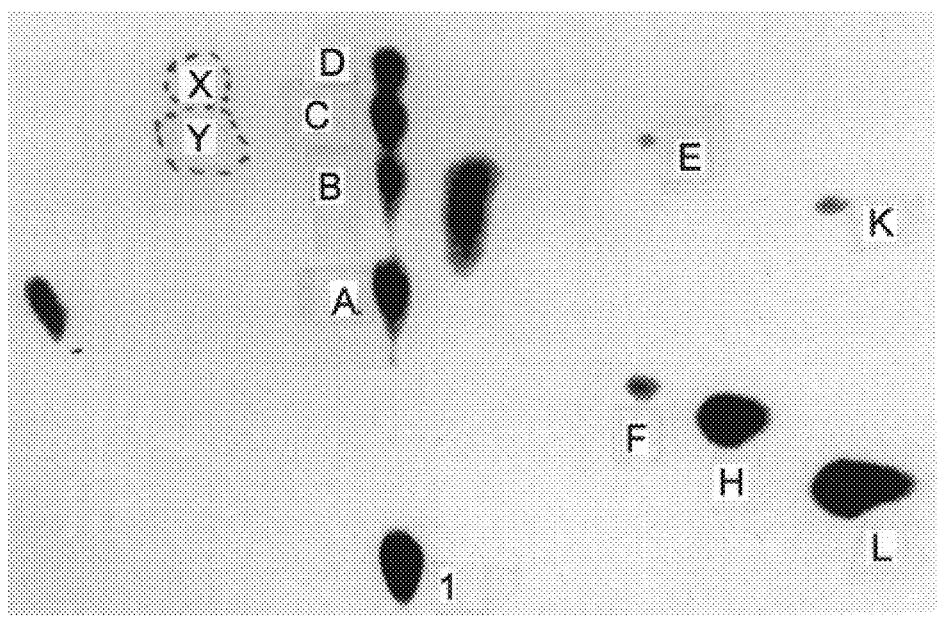

FIG. 9A and FIG. 9B show trypsin/V8 mapping of F283 and wild type p210 Bcr-Abl. The F283 mutant of p210 Bcr-Abl from COS cells is compared to the map of p210 Bcr-Abl from K562 cells (FIG. 9A). The dashed circles or Xs identify peptides lacking in the mutant.

Figure 10A:
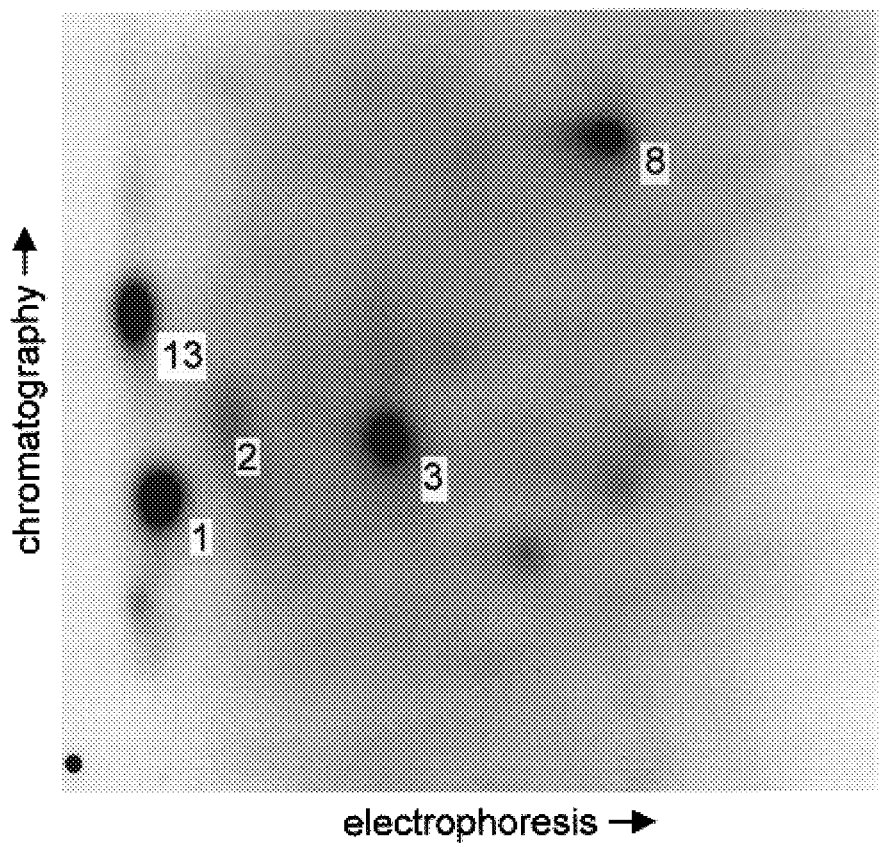
FIG. 10A and FIG. 10B show an absorbed tryptic map of p210. GST-Abl SH2 binds phosphotyrosine tryptic peptide 3, which contains tyrosine 283. p210 Bcr-Abl labeled in the in vitro kinase assay from K562 cells was purified on SDS gels, digested with trypsin and the digest was split in two parts. One was absorbed with GST (FIG. 10A) and the other with GST-Abl SH2 (FIG. 10B). The peptides that did not bind to the beads were separated on thin layer plates as usual. The dashed circles identify peptides lacking in the GST-Abl SH2 absorbed fractions.
Figure 10B:
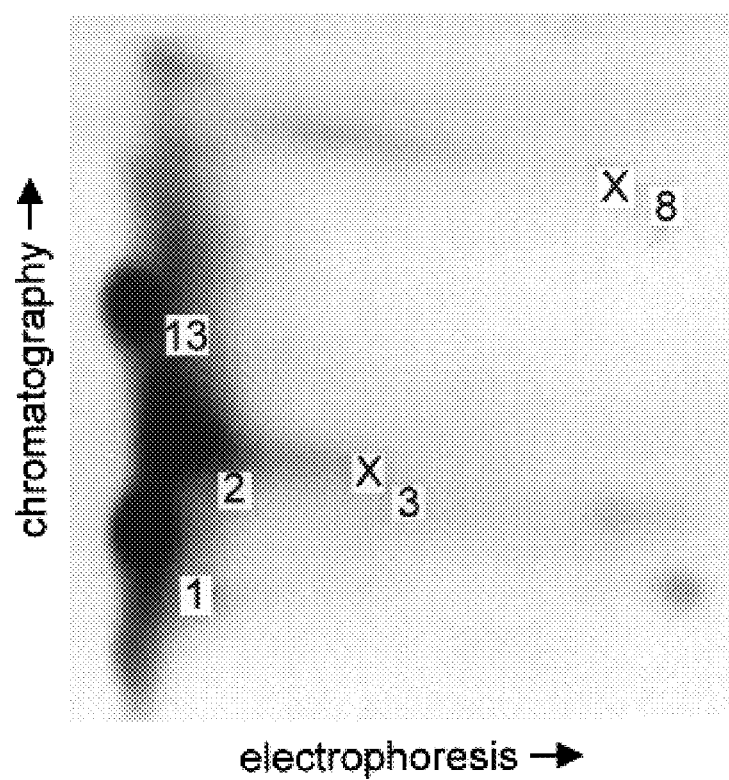

In FIG. 10A AND FIG. 10B, spots #3 and #8 specifically bound to the GST-Ras Gap SH2 fusion protein, but not to GST. Spot #3 contains a peptide designated 255–293 (SEQ ID NO:11) having tyrosines 283, 279 and 276 (not phosphorylated). Tyrosine 283 is not involved in binding Ras Gap. Therefore, tyrosine residue 279 is likely to be part of the peptide of Bcr that binds Ras Gap.

The sequence 255–293 (SEQ ID NO:11) binds Ras Gap and an SH2 domain of Abl. Fragments of this peptide that include at least Bcr 278–284 or Bcr 278–282, such as Bcr 278–290, provide useful peptides for inhibition of Bcr-Abl.

A further tyrosine at position 283 (residues 255–293, SEQ ID NO:11) is also phosphorylated by the Abl tyrosine kinase within Bcr-Abl. Several other tyrosines within Bcr are also phosphorylated by Bcr-Abl. They are likely to be $Y^{70}$ and $Y^{279}$, or possibly tyrosine at positions 58, 231 or 246. $Y^{276}$, $Y^{316}$ and $Y^{328}$ appear not to be sites of phosphorylation.

EXAMPLE V

Abl SH2 Domain Binds to a Bcr Peptide Within the First Exon of Bcr-Abl

The inventors performed similar studies with the SH2 domain of Abl. These were performed with a mouse c-Abl SH2 sequence, which differs by only two amino acids from the human sequence within the SH2 domain.

The results indicate that phosphotyrosine tryptic peptides #3 and #8 bind to GST-Abl SH2 but not to GST (FIGS. 10A and 10B). It is not known why Ras Gap SH2 and Abl SH2 bind the very same phosphotyrosine tryptic peptides.

The sequence of peptide 8 is 637 NSLETLLYK 644, (SEQ ID NO:12), its position is outside of the first exon (it is lacking in p185 Bcr-Abl but present in p210 Bcr-Abl; the former contains only the first exon of Bcr whereas the latter contains more than 900 amino acids of Bcr.) Peptide #3 has the sequence of amino acids 255 FLKDNLIDANGGS RPPWPPLEYQPYQSIYVGGMMEGEGK 293 (SEQ ID NO:11, the underlined residues are sites resistant to trypsin).

EXAMPLE VI p160 Bcr Binds to Grb2

The following study was carried out to demonstrate that tyrosine 177 phosphorylated p160 Bcr binds to a simian Grb2 molecule, an activator of the Ras signaling pathway.

It has been shown that phosphotyrosine 177 of Bcr sequences within Bcr-Abl is required for its direct interaction with SH2 domain of Grb2, an SH2 and SH3 domain-containing adaptor molecule (Pendergast et al., 1993). The interaction is important for activation of Ras function and transformation by Bcr-Abl (Pendergast et al., 1993).

As p210 Bcr-Abl can transphosphorylate p160 Bcr on tyrosine 177, it was of interest to test whether tyrosine 177 phosphorylated p160 Bcr might also be able to bind to Grb2 protein within cells. Searching for such a complex is difficult in cells that express both p210 Bcr-Abl and p160 BCR since p210 Bcr-Abl will interact with both p160 Bcr and Grb2 proteins.

In order to demonstrate direct interaction between tyrosine phosphorylated p160 Bcr and Grb2 proteins, it is reasonable to take the advantage of the facts that p160 BCR can be tyrosine phosphorylated by p146 c-Abl and the lack of physical interaction of p145 c-ABL with either p160 Bcr or Grb2.

Figure 18:
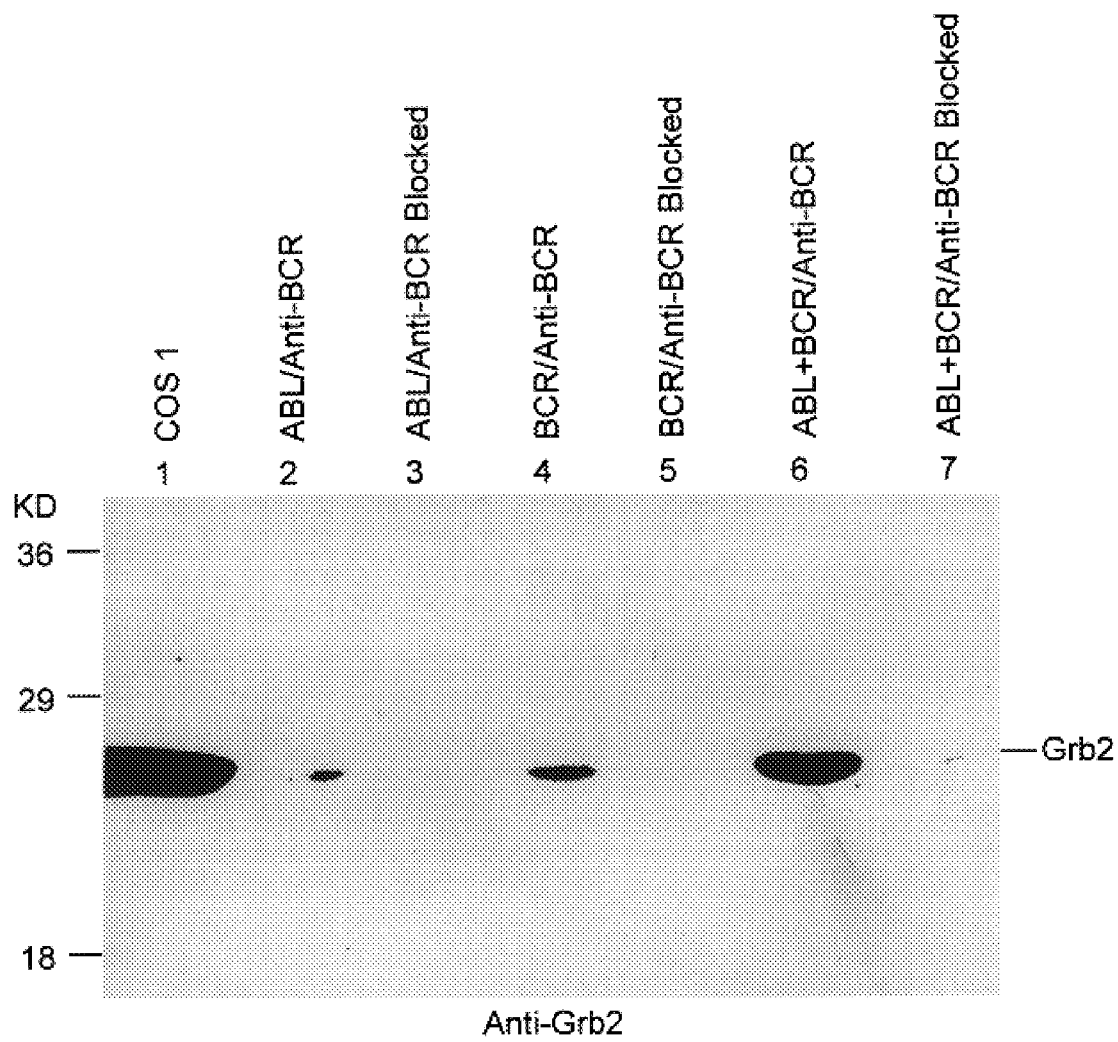
FIG. 18 shows physical interaction of tyrosine phosphorylated p160 BCR with simian Grb2 protein in COS1 cells overexpressing both p160 BCR and p145 c-ABL. Anti-Grb2 Western blotting was performed on lysates of COS1 cell lysates (lane 1) or anti-BCR (1256–1271) antibody immunoprecipitates from COS1 cells transfected with human full length c-ABL (1b) (lanes 2 and 3), human full length Bcr (lanes 4 and 5) or cotransfected both human full length Bcr and c-ABl(1b) (lanes 6 and 7). Lane 3, 5 and 7 are immunoprecipitates obtained with pre-blocked anti-BCR (1256–1271) antibody. The bands were detected using the ECL method. Exposure time: 30 seconds.

COS1 cells express an endogenous simian Grb2 protein detected by Western blotting (FIG. 18, lane 1). P160 BCR and p145 c-ABL(1b) were separately or simultaneously expressed in COS1 cells. Two days after transfection, cells were harvested. The cell lysates were clarified by ultracentrifugation and the supernatants were incubated with either anti-BCR c-terminal (1256–1271) antibody (FIG. 18, lanes 2, 4 and 6) or peptide preblocked antibody (FIG. 18, lanes 3, 5 and 7). The immunoprecipitated proteins were then fractionated by a 10% polyacrylamide SDS PAGE and then transferred to a p-immoblin membrane. The membrane was then blotted by an anti-Grb2 antibody (FIG. 18).

The result showed that Grb2 protein can be specifically co-immunoprecipitated with tyrosine phosphorylated p160 BCR by anti-BCR c-terminal (1256–1271) antibody from COS1 cells overexpressing both p160 BCR and p145 c-ABL (1b) (compare FIG. 18, lanes 6 and 7). However, expression of either p160 BCR alone (FIG. 18, lanes 2 an d3) or p145 c-ABL alone (FIG. 18, lanes 4 and 5) did not result in significantly specific co-immunoprecipitation of Grb2 protein by anti-BCR c-terminal (1256–1271) antibody. The weakly blocked 24 kd protein bands are likely resulted form non-specific immunoprecipitation of simian Grb2 molecule by the polyclonal anti-BCR c-terminal (1256–1271) rabbit serum and the presence of low amount of tyrosine phosphorylated endogenous BCR protein.

The results indicate that p160 BCR when tyrosine phosphorylated by p145 c-ABL can interact with the endogenous similar Grb2 protein.

In order to determine whether phosphorylation of tyrosine 177 of p160 BCR by p145 c-ABL(1b) is responsible for the interaction of p160 BCR with simian Grb2 protein, the Grb2 binding ability of tyrosine 177 to phenylalanine mutant of p160 BCR was tested.

In this study, p145 c-ABL was coexpressed with either wild type p160 BCR or the mutant p160 BCR(F177) in COS1 cells. Cell lysates were subjected to immunoprecipitation by anti-BCR C-terminal (1256–1271) antibody and the immunoprecipitates were analyzed by Western blotting with an anti-Grb2 antibody.

Figure 19:
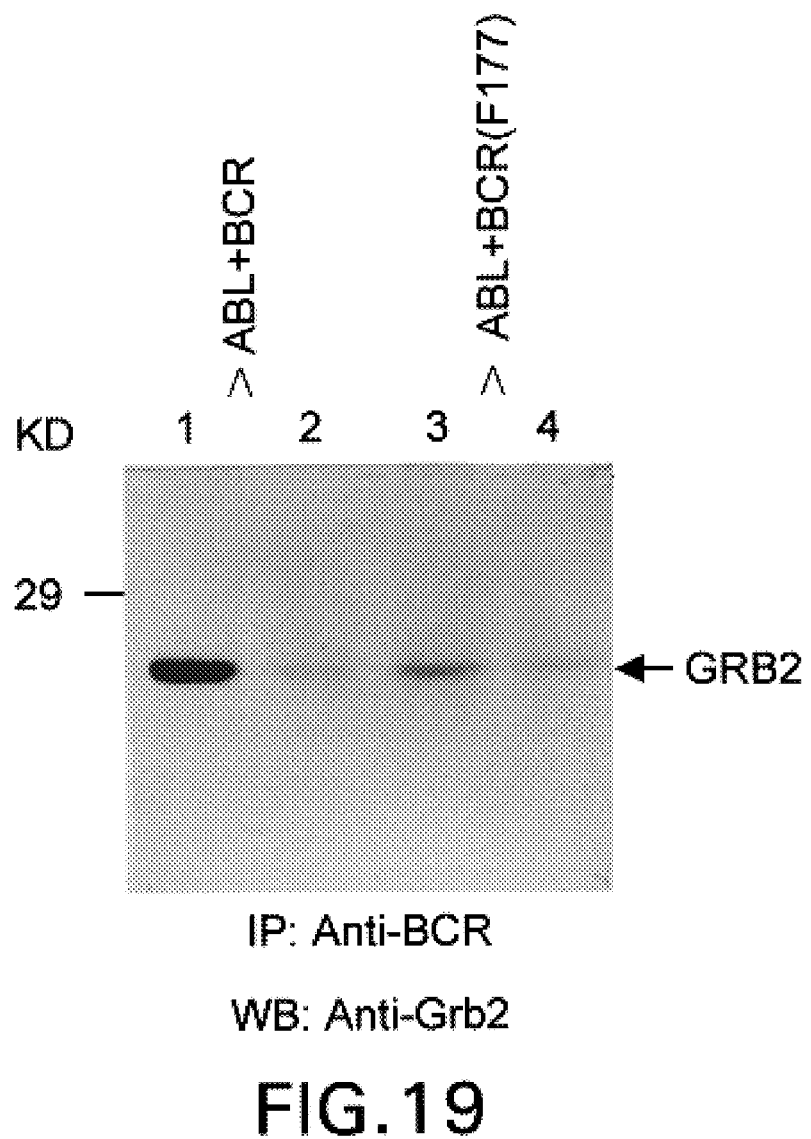
FIG. 19 shows phosphotyrosine 177 of p160 BCR is critical for its interaction with the simian Grb2 protein. Anti-Grb2 Western blotting was performed on anti-BCR (1256–1271) antibody immunoprecipitates of lysates from COS1 cells cotransfected p145 c-ABL with either wild type p160 BCR (lanes 1 and 2) or p160 BCR (F177) (lanes 3 and 4) mutant. Lanes 2 and 4 are immunoprecipitation with pre-blocked anti-BCR (1256–1271) antibody.

As expected, tyrosine phosphorylated wild type p160 PCR by p145 c-ABL(1b) was able to bind specifically to simian Grb2 proteins (compare lanes 1 and 2 of FIG. 19). However, coexpression of p145 c-ABL(1b) with p160 BCR lacking tyrosine 177 in COS1 cells resulted in a much reduced level of coimmunoprecipitate simian Grb2 protein by anti-BCR C-terminal (1256–1271) antibody (compare lanes 3 and 4 of FIG. 19 to lanes 1 and 2). This weak coimmunoprecipitation observed in lane 3 and 4 of FIG. 19 is likely resulted from non-specific immunoprecipitation by the anti-GBCR (1256–1271) antibody and the presence of endogenous wild type BCR.

These results indicate that not only phosphotyrosine 177 of Bcr-Abl but also phosphotyrosine 177 of p160 BCR are able to bind to Grb2 proteins. It also implicated that normal c-Abl protein, when activated, may activate Ras pathway through phosphorylation of tyrosine 177 of p160 BCR.

EXAMPLE VII

Inhibition of Bcr-Abl by Short Peptides

This example shows that a short peptide sequence encoded by the first exon of the BCR gene (SEQ ID NO:22) strongly inhibits Bcr-Abl protein tyrosine kinase activity in test tube kinase reactions. This Bcr peptide must be phosphorylated on a serine residue (possibly only one of several) in order for it to function as an inhibitor.

SEQ ID NO:10, Bcr 353–364 (housing Tyr 360), is identified herein as a useful inhibitory peptide. The inventors next initiated studies with a longer form of this peptide (SEQ ID NO:22). This was chosen because SH2 domains generally require a motif that includes sequences preceding and following a phosphorylated tyrosine residue.

The inventors first focused on a modified form of SEQ ID NO:22 containing a phosphoserine. This peptide is also termed pS354 S17K. The effect and inhibitory activity of pS354 S17K towards the Bcr-Abl kinase was determined.

pS354 S17K is 350-SSRVpS*PSPTTYRMFRDK-366 (SEQ ID NO:22). The sequence begins at Bcr residue 350 and ends at Bcr residues 366, located within the first exon coding region of the BCR gene. The pS* identifies phosphoserine. The peptide was made by Merrified chemistry and purified by column chromatography and HPLC to about 95% purity.

Figure 21:
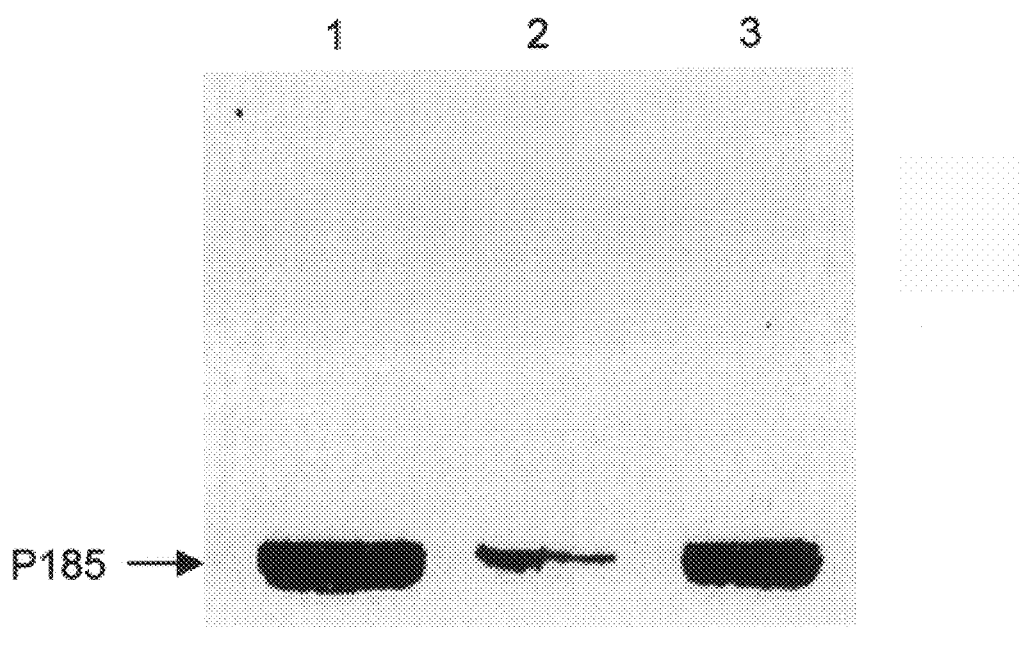
FIG. 21. Phosphoserine Bcr peptide pS354 S17K (SEQ ID NO:22) inhibits the Bcr-Abl tyrosine kinase activity. The SUP B15 cell line derived from a patient with Bcr-Abl-positive acute lymphocytic leukemia (ALL) were grown in culture; cells were lysed and the Bcr-Abl oncoprotein immunoprecipitated with a monoclonal antibody p6D (anti-Abl 51–64). The immune complexes were mixed with either no peptide or 50 $\mu$g of peptide prior to addition of the kinase activating buffer containing [$\gamma$-$^{32}$P]ATP. After the assay was completed, the proteins were fractionated by SDS gel electrophoresis. Radioactive proteins were detected by phospho-image analysis. Lane 1, no peptide; lane 2, 50 $\mu$g of pS354 S17K; lane 3, 50 $\mu$g of unphosphorylated S17K.

Assays that measure the Bcr-Abl kinase activity frequently utilize the autophosphorylation reaction in which one molecule of Bcr-Abl tyrosine phosphorylates another Bcr-Abl molecule. The Bcr peptide was shown to inhibit the Bcr-Abl tyrosine kinase as measured by its addition to immunocomplexes that contain P185 BCR-ABL in auto kinase assays (FIG. 21).

The pS354 S17K peptide sequence strongly inhibited the Bcr-Abl kinase activity (compare lane 1 to lane 2), whereas unphosphorylated S17K had little affect (lane 3). Similar results were obtained with the other form of the Bcr-Abl oncoprotein (P210 BCR-ABL).

EXAMPLE VIII

Inhibition of Bcr-Abl by Long Peptides

The present example shows that a larger segment of the Bcr protein, encoded by the first exon of the BCR gene, inhibits the tyrosine kinase activity of the Bcr-Abl oncoprotein in test tube kinase reactions. This Bcr protein is a potent inhibitor of the Bcr-Abl tyrosine kinase within cells.

The inventors reasoned that a fragment of the Bcr protein containing both serine-rich boxes of Bcr might also function as a potent inhibitor of the Bcr-Abl tyrosine kinase.

Figure 22:
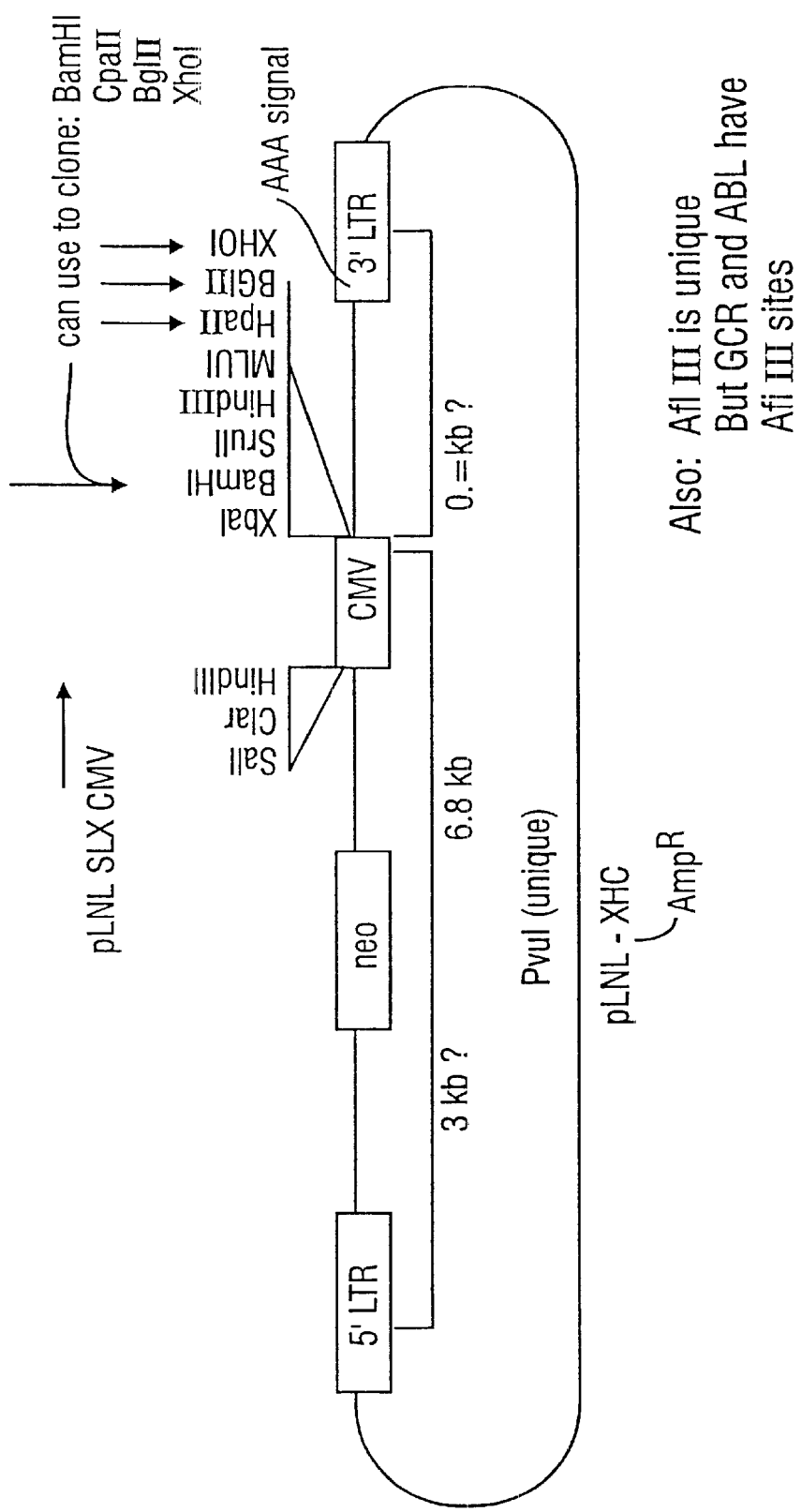
FIG. 22. Structure of the Bcr fragment that inhibits the Bcr-Abl protein tyrosine kinase. The amino acid sequence of the Bcr fragment used is that of SEQ ID NO:28, which begins at residue 64 and ends at residue 413 of SEQ ID NO:1. The Bcr coding sequence (McWhirter and Wang, 1991) was inserted into vector pLNL SLX CMV at the Bam H1 site of the vector with a linker sequence. The translation product begins with five amino acids fused to the amino terminal Bcr sequence beginning with AKE - - - ; the linker sequence at the 3' end adds a LV followed by a stop codon to the carboxy terminus of the Bcr sequence ( - - - GQI).

The inventors constructed a DNA vector encoding Bcr sequences from amino acid 64 to 413 (SEQ ID NO:28; FIG. 22). This construct produces a short Bcr protein containing both A and B serine-rich boxes (Pendergast et al., 1991). The DNA segment encoding amino acids 64 to 413 was derived from a Bcr-Abl DNA clone provided by Dr. Jean Wang (McWhirter and Wang, 1991). The Bcr coding sequence was inserted into vector pLNL SLX CMV.

The Bcr fragment was expressed in COS-1 cells by transient transfection with the Bcr fragment vector construct shown in FIG. 22. Lysates of transfected COS-1 cells were immunoprecipitated with a rabbit antibody prepared against a synthetic Bcr peptide encompassing Bcr residues EFH-HERGLVKVNDKE (181–194 of SEQ ID NO:11). In other studies, the inventors showed this construct produced the expected size Bcr protein fragment of the appropriate size in NIH 3T3 cells by Western blotting with the anti-Bcr 181–194 antibody.

Figure 23A:
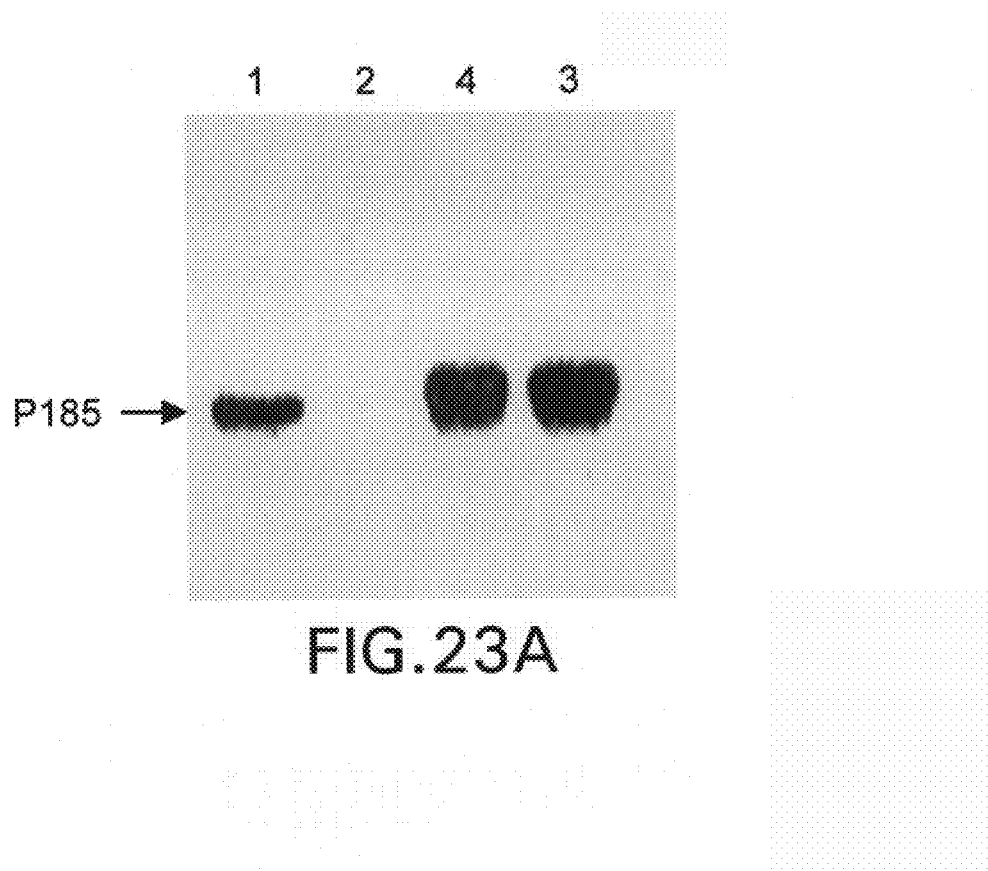
FIG. 23A, FIG. 23B and FIG. 23C. A Bcr fragment expressed in COS-1 cells inhibits the Bcr-Abl tyrosine kinase in vitro. In these studies, the Bcr fragment was expressed in COS-1 cells, then isolated by immunoprecipitation with anti-Bcr 181–194 antibody. This immune complex was isolated by binding to protein A Sepharose beads; these immune complexes were added to protein A Sepharose beads containing P185 BCR-ABL harvested from SUP B15 leukemic cells with anti-Abl 51–64. The autokinase reaction was performed to measure the tyrosine kinase activity of Bcr-Abl.

The immunoprecipitate from the COS-1 cell transfected with Bcr fragment (64–413) was added to immuoprecipitates of P185 BCR-ABL derived from the leukemic cell line SUP B15. The results showed that the Bcr fragment was a potent inhibitor of the Bcr-Abl tyrosine kinase activity (FIG. 23A, compare lane 4 to lane 2).

When the immunoprecipitate was boiled for a few minutes prior to addition to the kinase assay, the inhibitory activity was strongly decreased (compare lanes 1 and 2). This is the expected result if the inhibitor is in fact the Bcr fragment protein, as protein confirmation is largely destroyed by temperatures approaching 100° C.

Figure 23B:
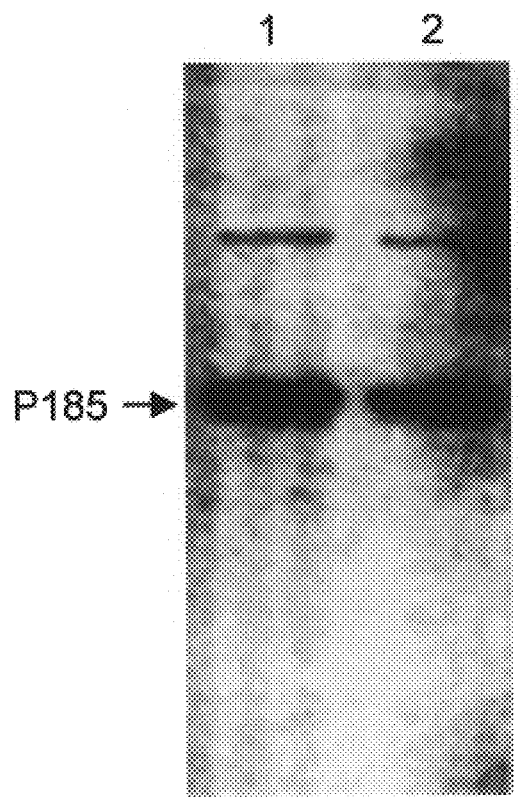

To measure the level of the Bcr-Abl oncoprotein in the kinase assay, the anti-Abl immunocomplexes from lanes 2 and 4 were analyzed by Western blotting with the anti-Bcr 181–194 antibody. The results indicate that the amount of Bcr-Abl protein (P185) was essentially unchanged in amount (FIG. 23B), but the level of autophosphorylation was dramatically decreased by exposure to the anti-Bcr immunocomplex containing the Bcr fragment protein (FIG. 23A, lane 2).

Figure 4:
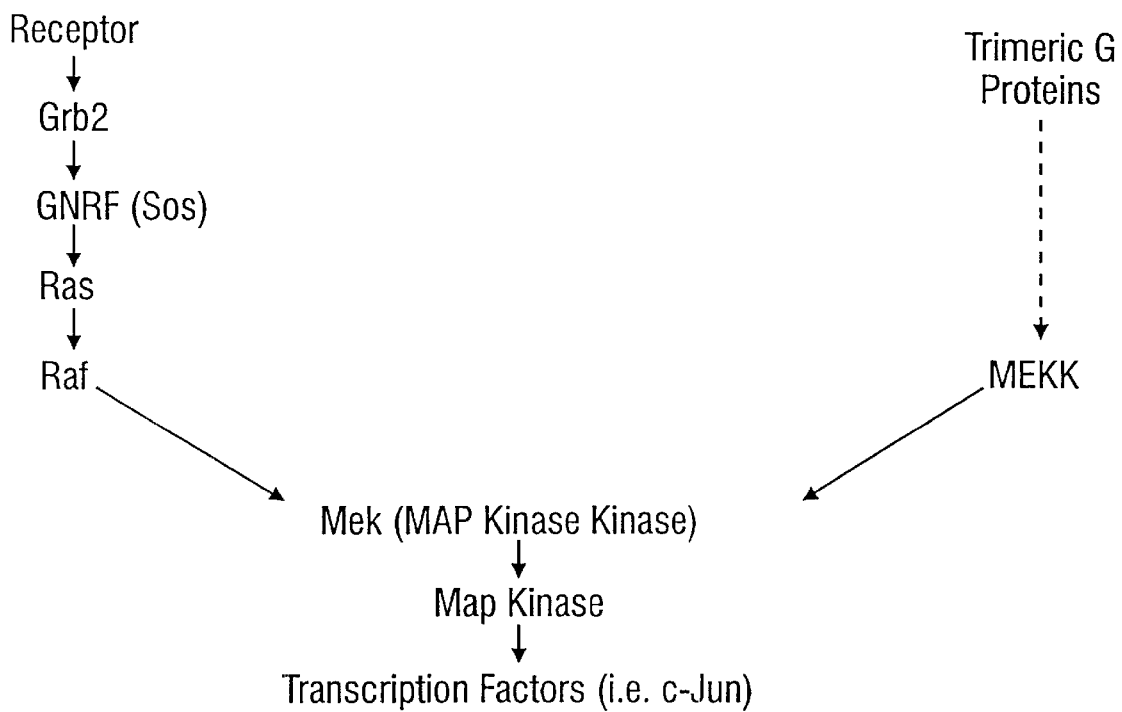
FIG. 4 outlines the pathway of activation of transcription factors by receptor/ligand interaction.
Figure 5:
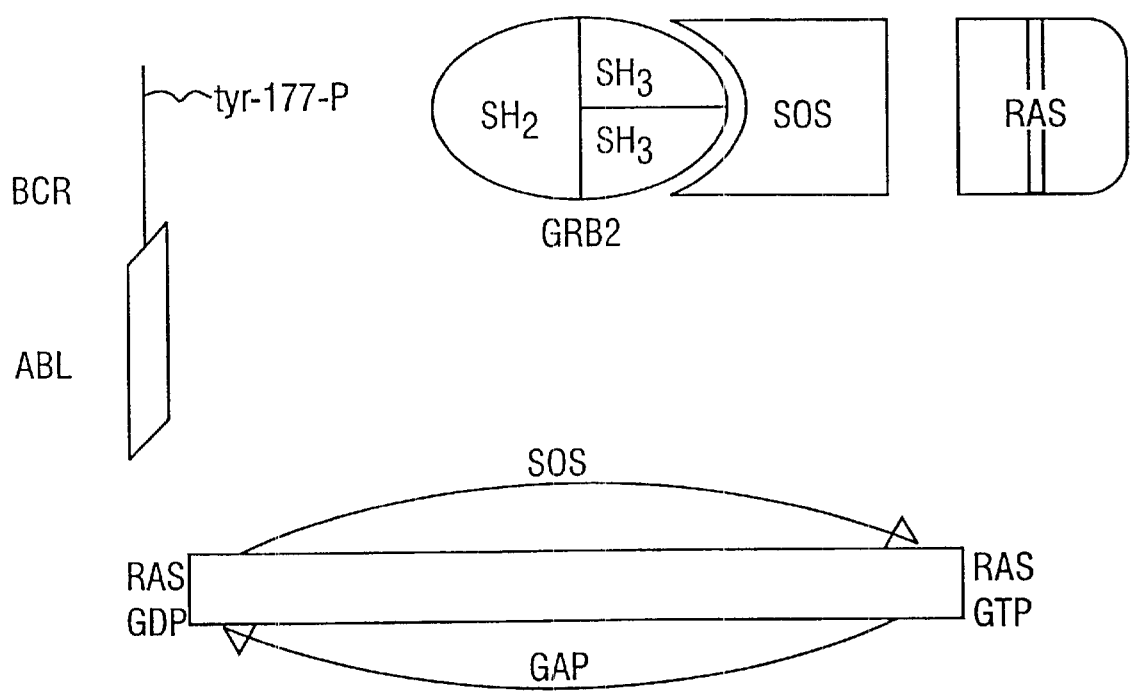
FIG. 5 outlines an activation pathway of Ras by Bcr-Abl.
Figure 23C:
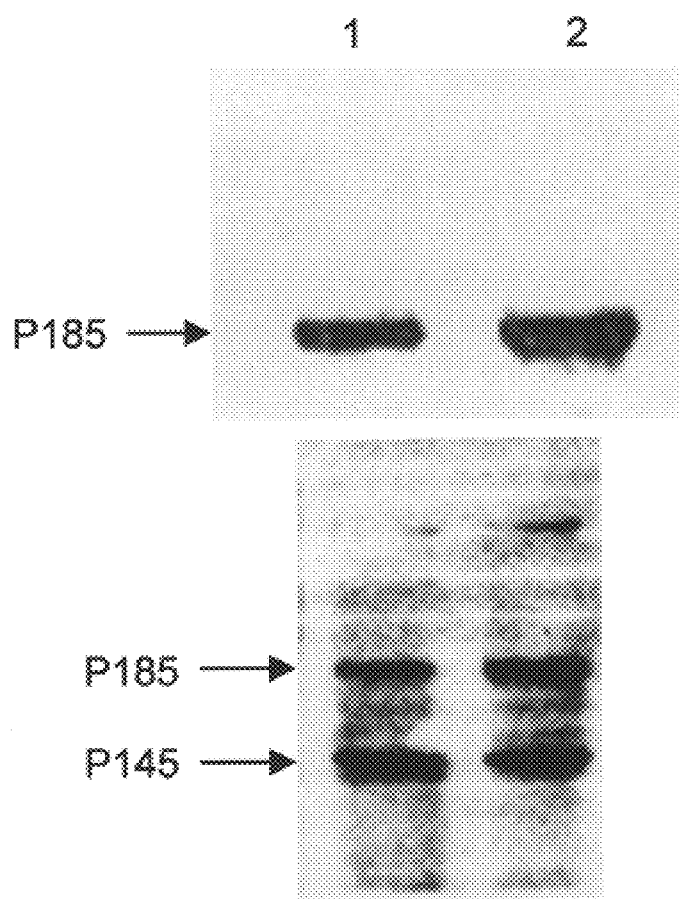

To eliminate the possibility that the anti-Bcr 181–194 antibody was itself inhibitory to Bcr-Abl, the inventors mixed antibody not exposed to the Bcr fragment with Bcr-Abl (FIG. 23C). The results show that the antibody itself was not inhibitory to Bcr-Abl (compare lanes 1 and 2 of FIG. 23C). Again the inventors measured the level of the Bcr-Abl protein in the immune complexes but this time by Western blotting with anti-Abl 8E9 antibody (lower portion of FIG. 23C of FIG. 4). The level of Bcr-Abl protein did not change.

In this study (FIG. 23A), the level of the Bcr fragment protein in COS-1 cells was likely to be at the same level as that observed for the Bcr-Abl protein in most cell lines. Therefore, the amount of the Bcr protein fragment was likely to be at similar molar amounts to the amount of the Bcr-Abl protein in these kinase assays.

Therefore, the inventors conclude that the Bcr fragment protein of SEQ ID NO:28 is a very potent inhibitor of the Bcr-Abl tyrosine kinase. The Bcr fragment was likely to be phosphorylated on serine residues (at least on serine 354) as a result of expression in COS-1 cells. The inventors presume that its phosphorylation was catalyzed by cellular serine kinases present in COS-1 cells (possibly endogenous Bcr, which is a serine/threonine kinase).

The effects of the Bcr peptide on other kinases were measured and results indicate that the Bcr inhibitory peptide stimulates the Bcr kinase but has little effect on the p60 Src tyrosine kinase.

These results support the proposal that normal Bcr can oppose the growth effects of Bcr-Abl. Importantly, they strengthen the strategy of producing specific drugs to counteract the leukemic effects of the Bcr-Abl oncoprotein. The drugs include either liposome/peptide formulations or gene therapy induced expression of the Bcr fragment protein of SEQ ID NO:22 and the other peptides described herein.

EXAMPLE IX

Inhibition of Bcr Serine Kinase by Tyrosine Phosphorylation

Bcr is known to possess an intrinsic serine/threonine kinase activity. In this example, the inventors have examined the significance of tyrosine residues within the Bcr amino terminus with regard to their effect on its serine/threonine kinase activity. The phosphorylation of Bcr by Bcr-Abl on tyrosine residues, including T-360, greatly inhibited the serine/threonine kinase function of Bcr.

P160$^{BCR}$ (Y360F) has Reduced Transphosphorylation Activity, but its Autophosphorylation Activity is Unaffected: Tyrosine phosphorylation of different Bcr exon 1 residues could affect Bcr's enzymatic activity. Moreover, tyrosine residues may be involved in regulating Bcr's serine/threonine kinase activity.

To test this, the inventors generated Y>>F BCR cDNAs for several residues and these mutant Bcr proteins were examined for serine/threonine kinase activity.

Mutant forms of P160$^{BCR}$ were expressed in COS-1 cells and tested for serine/threonine kinase activities in immune complex kinase assays.

Mutant Y360F Bcr P160 was severely inhibited in its ability to transphosphorylate an exogenously added substrate, casein, compared with that of wild-type Bcr. In contrast, P160$^{BCR}$ autophosphorylation was not detectably altered by the Y360F mutation.

Western blotting of such extracts showed that the Y360F Bcr mutant protein was stable. Using the intensities of the P160$^{BCR}$ bands as an indication of the amount of active P160$^{BCR}$ in the immune complex and the intensities of the casein bands as a measure of transphosphorylation activity, the transphosphorylation activity of the Y360F Bcr mutant was reduced about sevenfold, compared with that of the wild type. Similarly, the Y360F Bcr mutant was also defective in transphosphorylating another exogenous substrate, histone H1.

To determine whether other tyrosine residues in Bcr exon 1 are similarly important to Bcr's serine/Threonine kinase activity, the inventors assayed the Y283F mutant Bcr protein. Bcr Y283F was not significantly altered in its ability to phosphorylate casein.

The amounts of Bcr within these immune complexes were quantitated in two ways. In a first method, the amounts of Bcr mutants would be underestimated by about 10%, compared with that of the wild type. On the basis of these measurements, the specific activity of transkinase activity (casein intensity/P160$^{BCR}$ intensity) of the Y360F Bcr mutant (0.03) was reduced more than 20-fold in this study, compared with that of the wild type.

The second method of estimating the amounts of P160$^{BCR}$ in immune complexes involved the Western blotting of these immune complexes with an anti-Bcr antibody. The specific activity of Y360F was reduced by about sixfold. Thus, these two methods established that the Y360F Bcr protein had significantly reduced ability to phosphorylate an added substrate, compared with that of wild-type Bcr. By using autophosphorylation of the Bcr protein as a measure of its relative amount, the reduction of Bcr's transkinase by the Y360F mutation was about sevenfold, confirming the results obtained by the Western blot method.

Depression of Bcr's Serine Kinase Activity by Bcr-Abl: Because the Y-360 residue is critically involved in Bcr's transphosphorylation activity and because of the failure of wild-type Bcr-Abl to reduce the Y360F defect, the inventors tested the effects of tyrosine phosphorylation of wild-type Bcr on it serine/threonine kinase activity. Bcr-Abl and Bcr immune complexes from separate aliquots of COS-1 cells were mixed to allow Bcr-Abl to tyrosine phosphorylate Bcr. The inventors then assayed the effect of tyrosine phosphorylation of Bcr on it serine/threonine kinase activity.

Control Bcr P160 phosphorylated casein, mostly on serine with low levels of threonine, P160$^{BCR}$ itself was also phosphorylated on serine/threonine residues. However, the addition of Bcr-Abl immune complexes to Bcr immune complexes severely reduced the level of serine/threonine phosphorylation of casein and caused phosphorylation of casein on tyrosine residues.

The addition of Bcr-Abl to Bcr immune complexes also resulted in the transphosphorylation of Bcr on tyrosine residues and simultaneously blocked the serine/threonine autophosphorylation activity of Bcr. In these studies, the inventors measured the phosphoamino acid contents in P160$^{BCR}$ with and without treatment of Bcr immune complexes with Bcr-Abl. In these studies, Bcr and Bcr-Abl proteins were immunoprecipitated with anti-Bcr, which directly reacts with Bcr and Bcr-Abl proteins.

Autophosphorylated P160$^{BCR}$ contained phosphoserine/threonine. In contrast, P160$^{BCR}$ treated with Bcr-Abl contained predominantly phosphotyrosine, with only low levels of phosphoserine/threonine. These results demonstrate that in vitro tyrosine phosphorylation of wild-type Bcr severely inhibits its serine/threonine protein kinase, including both autokinase and transkinase activities.

Tyrosine-phosphorylated Bcr Isolated From Intact Cells is Deficient in Transkinase Activity: To determine whether Bcr harvested from cells coexpressing Bcr-Abl is also deficient in transkinase activity, the inventors isolated Bcr from cells under conditions that favor the retention of phosphotyrosine.

In these studies, the inventors immunoprecipitated Bar with anti-Bcr either from extracts of cells lacking Bcr-Abl or from cells that express Bcr-Abl. Under these conditions, Bcr-Abl is co-immunoprecipitated with Bcr. The inventors lysed cells in buffer containing 0.4 mM vanadate to block tyrosine phosphatases and therefore maintain the phosphotyrosines with Bcr.

Cells coexpressing Bcr with either P210$^{BCR-ABL}$ was severely deficient in casein phosphorylation activity. Quantitative measurements indicated that was 25-fold less active for casein phosphorylation than was Bcr from COS-1 cells lacking Bcr-Abl. These results demonstrate that tyrosine phosphorylation of Bcr by Bcr-Abl in the predominant factor in reducing Bcr's serine/threonine kinase activity.

EXAMPLE X

Bcr is a Negative Regulator of Bcr-Abl Function

The present example demonstrates reduction of Bcr kinase activity and Bcr/Bcr-Abl complexes by treatment of cells with a 3' BCR anti-sense oligonucleotide.

The facts that p160 BCR is a target for BCR-ABL protein tyrosine kinase and that tyrosine phosphorylated p160 BCR is able to interact within live cells with the Grb2 molecule, an activator of the Ras signaling pathway, are consistent with the hypothesis that p160 BCR plays a role in the pathogenesis of Ph$^1$-positive leukemias.

Tyrosine phosphorylation of p160 BCR by the activated tyrosine kinase of p145 c-ABL and its subsequent interaction with Grb2 protein indicate that p160 BCR might also be a very important signaling molecule in certain normal physiological processes.

In order to address the role of BCR in the oncogenic effects of BCR-ABL, BCR protein expression was specifically eliminated or reduced in cells expressing BCR-ABL. Antisense oligodeoxynucleotides are able to bind to the specific mRNA through base-pairing and then by degradation of the mRNA, interfere with protein expression. Since BCR-ABL lacks 3' BCR coding sequences (amino acid residues 927–1271), a 3' BCR antisense oligodeoxynucleotide should be useful in selectively reducing BCR expression without interfering with BCR-ABL expression.

3' BCR sequences share homology with several human genes such as p21 RasGAP and ABR genes. Therefore, selected 3' BCR sense and antisense oligonucleotide sequences were examined by FASTA search in GeneBank database to eliminate oligonucleotides that share significant homology with known human genes. Examination of the oligonucleotides by a primer selection program showed no significant secondary structure formation.

The following oligonucleotide sequences were selected: BCR3351-antisense, 5'ATCATCACCGACACATCC 3', SEQ ID NO:20; BCR3351-sense, 5'GGATGTGTCGGT-GATGAT 3', SEQ ID NO:21. The oligonucleotide sequences correspond to BCR coding sequences 3351 to 3368, which are not found within BCR-ABL sequences and other known human gene sequences.

The oligonucleotides were synthesized by Genosys Biotechnologies, Inc. (Houston, Tex. 77380-3600). Two phosphotriester linkages were placed at both ends of each oligonucleotide to enhance their resistance to endonuclease digestion and prolong their effects.

Figure 13:
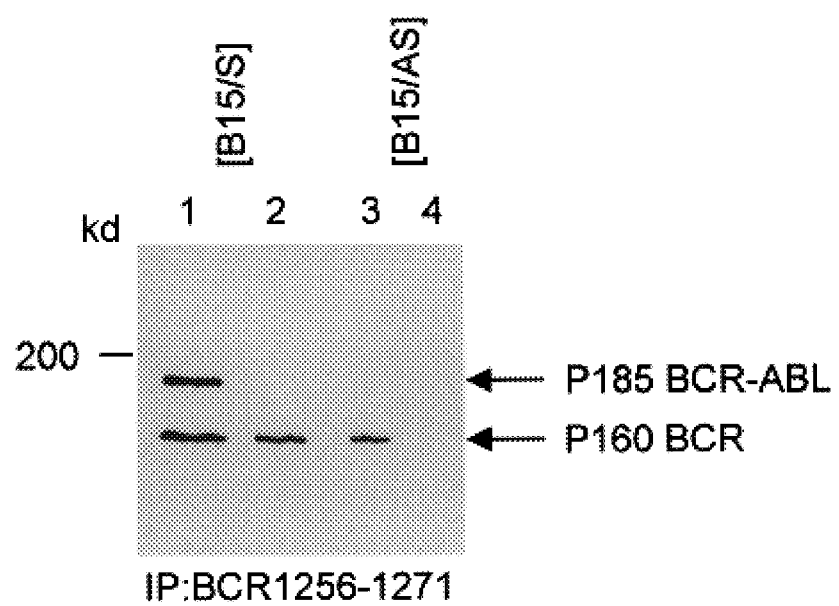
FIG. 13 shows inhibition of p160 BCR expression by 3' anti-sense BCR oligonucleotide treatment of SUP B15 ALL cells. SUP B15 cells were treated with anti-sense BCR oligonucleotides as in FIG. 12. Equal amounts of cells processed from sense and antisense treated cultures were harvested at day 7. Cells were analyzed for Bcr protein and Bcr/Bcr-Abl complexes by assaying with an antibody to the carboxy terminal of Bcr, as described (Liu et al., 1993). Lane 1 is an SDS gel pattern of the sense treated culture; lane 2 is the assay performed with peptide-blocked antibody. Lane 3 is the pattern from anti-sense treated culture; lane 4 is the peptide-blocked control. Comparison of lanes 1 and 3 indicates that the level of Bcr protein as well as its ability to form Bcr/Bcr-Abl complexes was severely inhibited by 3' BCR anti-sense treatment. Quantitation measurements indicate that the level of Bcr protein was reduced about 10-fold by antisense treatment compared to sense, when normalized for the amount of Abl protein in the cultures.

The effects of the sense and antisense 3' BCR oligonucleotides were tested on BCR expression in SUP-B15 cells, a cell line derived from a Ph[1]-positive acute lymphocytic leukemia patient that expresses p185 BCR-ABL. Immunokinase assays were performed with anti-BCR (1256–1271) peptide antibody (the antibody detects Bcr proteins but not Bcr-Abl proteins) to determine the level of BCR expression in B15 cells after 7 days treatment with either the sense or antisense 3' BCR oligonucleotides (FIG. 13, lanes 1 and 3).

The results showed that the antisense treated B15 cells express much lower levels of BCR protein compared with that of the sense treated cells.

Figure 12:
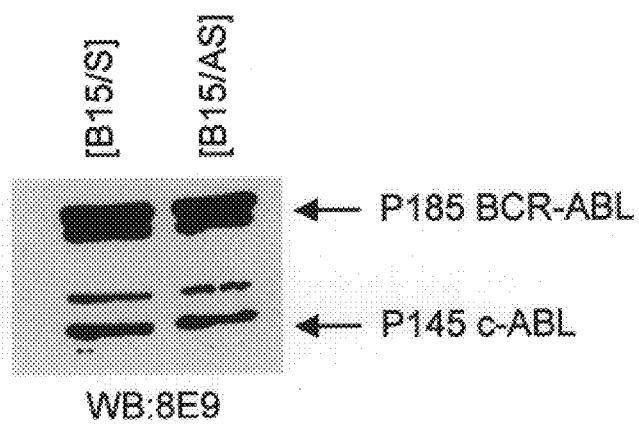
FIG. 12 shows Bcr-Abl protein expression in SUP-B15 cells treated with sense and anti-sense 3'BCR. SUP-B15 cells express p185 BCR-ABL; they were derived from a patient with Philadelphia chromosome-positive ALL. One-tenth of the cells harvested in the study shown in FIG. 13 was assayed for Bcr-Abl expression by Western blotting with the anti-Abl monoclonal antibody 8E9. Quantitation of these results indicates that there was a 35% reduction in Bcr-Abl protein in the anti-sense treated cultures (lane 1) compared to sense (lane 2). Similarly, the Abl protein was reduced about 26% in the anti-sense treated culture compared to sense. Quantitation was done by a densitometer SI unit (Molecular Dynamics).

Since the C-terminal Bcr antibody does not detect Bcr-Abl, the level of co-precipitated Bcr-Abl with Bcr gives an estimate of the amount of Bcr/Bcr-Abl complexes. Of importance, these assays showed that the amount of p160 BCR/p185 BCR-ABL complexes were also reduced in the antisense treated B15 cell compared to the sense treated cells (FIG. 13, lanes 1 and 3). In this study, equal amounts of the sense and the antisense oligonucleotide treated B15 cells were analyzed. Western blot analyses with an anti-Abl monoclonal antibody showed that the expression of p185 BCR-ABL was not significantly altered by the antisense and the sense oligonucleotides treatment (FIG. 12).

These results showed the 3' BCR antisense oligonucleotide specifically reduced the expression of normal BCR without interfering with the expression of BCR-ABL.

Quantitation analyses of the p160 BCR observed in lanes 1 and 3 of FIG. 13 by a densitometer (Molecular Dynamics) showed that the antisense treated B15 cells contained about 14 times less Bcr than that of the sense treated cells. However, quantitation analyses of FIG. 12 showed that levels of Bcr-Abl and c-Abl of antisense treated B15 cells were reduced about 1.6 and 1.35 fold, respectively, than that of the sense treated cells. Using c-Abl as an internal control, the actual reduction of p160 BCR in B15 cells by the antisense treatment is about 10 fold.

Figure 20A:
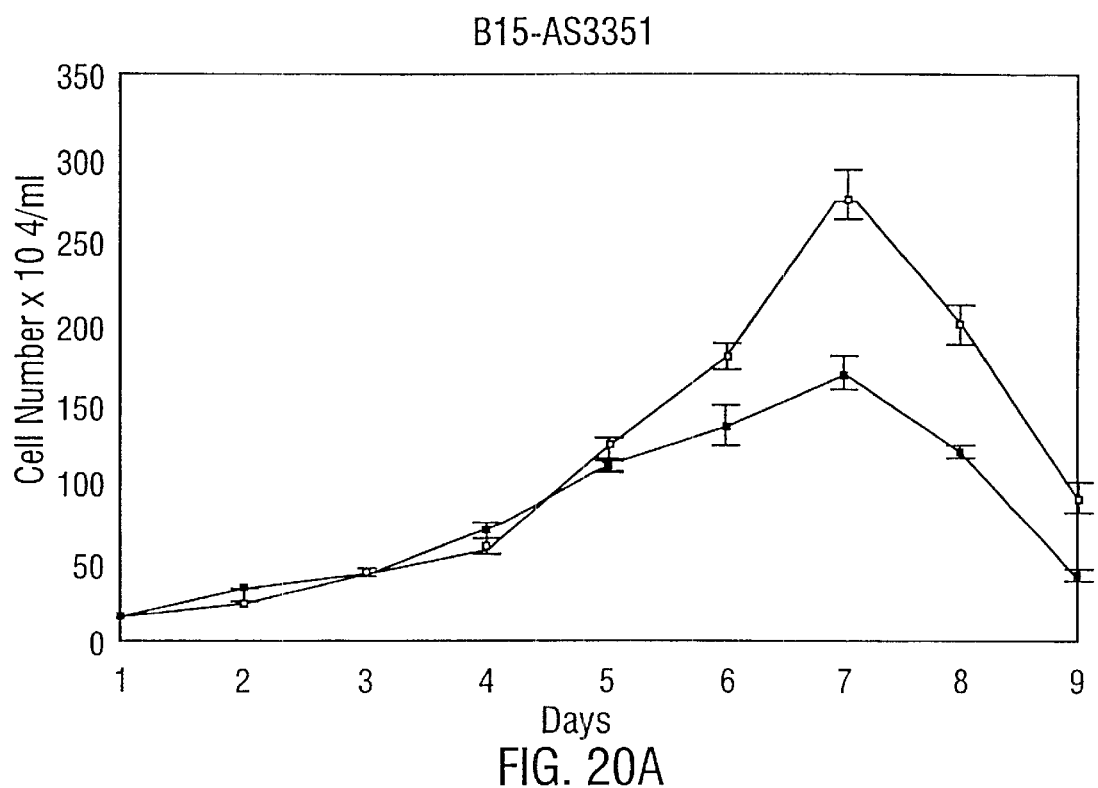
FIG. 20A and FIG. 20B show effects of 3' BCR antisense oligonucleotides on the growth of p185 BCR-ABL expressing SUP-B15 cells and p210 BCR-ABL expressing M3.16 cells.

The biological effects of the 3' BCR antisense oligonucleotide treatment were tested on SUP-B15 cells. SUP-B15 cells were seeded in triplicate wells at a concentration of $1.6 \times 10^5$ cells/ml in a 200 µl volume of RPMI media supplemented with 20% FCS. Oligonucleotides were added to the cells at a final concentration of 10 µM. Cell number was monitored by trypan blue exclusion assay for 9 days. The mean cell number of the triplicates was determined each day (FIG. 20A).

It was expected that antisense 3' BCR oligo would increase growth of Bcr-Abl expressing cells because of the proven role of Bcr phosphotyrosine 177 in stimulating the Ras pathway (Pendergast et al., 1993; Puil et al., 1994; FIG. 18 and FIG. 19). Results showed that antisense oligonucleotide treatment of SUP-B15 cells sustained a higher growth density compared to sense oligonucleotide treatment.

Figure 20B:
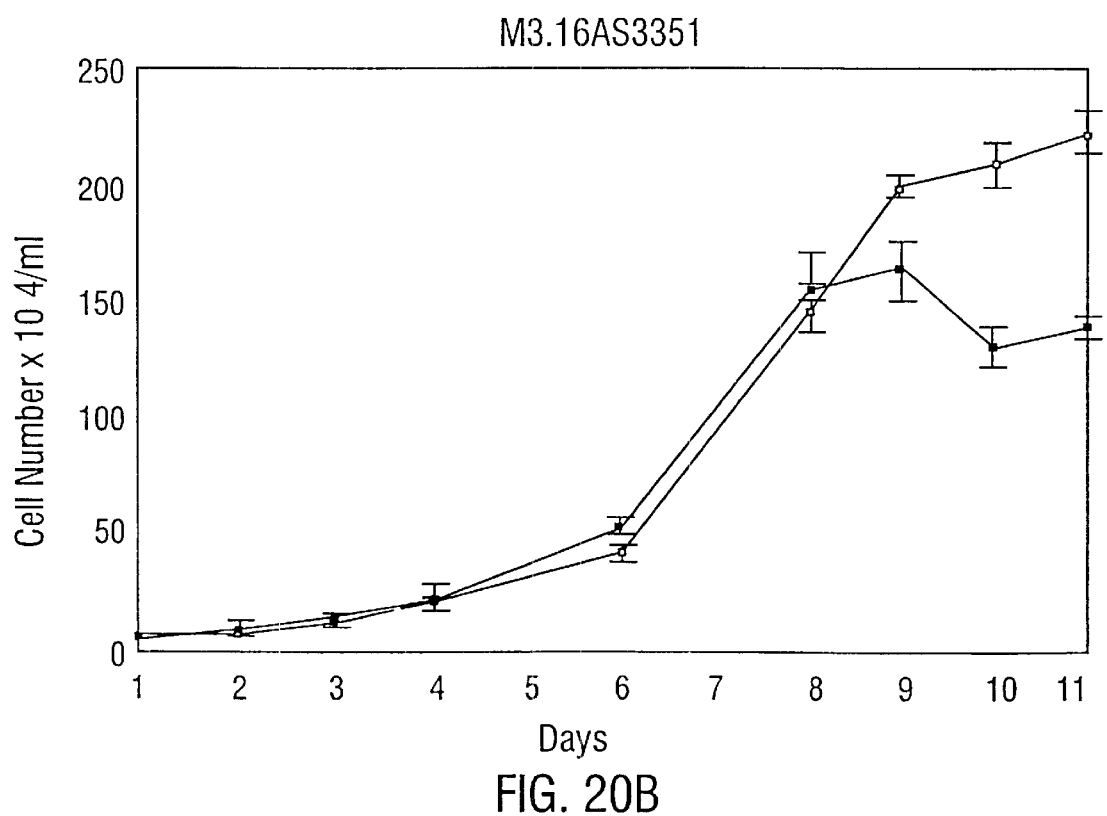

Similar results were obtained from treatment of M3.16 cells (human megakaryocytic cells transfected with p210 BCR-ABL) (FIG. 20B). For this particular study, the cell number was followed up for a longer period of time (11 days) and oligonucleotides were added again at day 5 at half of the initial concentration. Light microscopic examination of the cell culture at day 9 revealed that the antisense treated M3.16 cells were more confluent than sense treated cells.

In summary, the inventors performed studies to determine whether Bcr protein was reduced by the 3' BCR anti-sense treatment. Therefore, a sufficient amount of p185 BCR-ABL expressing SUP-B15 cells was treated with sense and antisense 3' BCR oligos for seven days in culture. Anti-sense treated cultures had twice as many live cells as the sense treated cultures. Two types of assays were performed on these cultures.

First, the level of Bcr-Abl protein was assayed by Western blotting. The anti-sense treated culture had no significant change in the expression of the Bcr-Abl protein compared to the sense-treated culture (FIG. 12). Therefore, the increased rate of growth was not a result of increased Bcr-Abl expression.

Second, lysates of anti-sense and sense-treated cultures were assayed by immune complex kinase assays with antibodies to the carboxy terminus of Bcr, which have been shown to detect Bcr/Bcr-Abl complexes (Campbell et al., 1990; Liu et al., 1993). These antibodies detect Bcr directly but not Bcr-Abl protein. However because Bcr can complex with Bcr-Abl, this assay also detects Bcr-Abl which is co-precipitated along with Bcr.

Incubation of these immune complexes with labeled ATP causes tyrosine phosphorylation of Bcr by Bcr-Abl and autophosphorylation of Bcr-Abl (Liu et al., 1993). Comparison of lysates from sense and anti-sense treated cultures showed a dramatic reduction in Bcr and Bcr/Bcr-Abl complexes by anti-sense (FIG. 13). Phosphorimager analyses indicated that the amount of Bcr was reduced about 14-fold by anti-sense 3' BCR. Using Abl Western blot data as an internal control for mass, the specific reduction in Bcr is estimated to be about 10-fold.

Therefore, the data in FIG. 12 and FIG. 13 indicated that the anti-sense 3' BCR oligo dramatically reduced the amount of functional Bcr and Bcr/Bcr-Abl complexes while not significantly affecting the level of Bcr-Abl protein. These results provide support for Bcr being a negative regulator of Bcr-Abl function.

EXAMPLE XI

Normal Bcr Protein has a Negative Regulatory Role

The present example demonstrates that 3' BCR anti-sense treated Bcr-Abl expressing cells maintained in low serum have enhanced survival compared to sense treated cells.

The differences between the growth patterns of sense and antisense oligonucleotide treated cells are not observed until late in the culture cycle. These results suggest that some factor in the medium could overcome the effects of antisense 3' BCR oligonucleotide. It is possible that reduced serum level is required for the effects induced by antisense oligonucleotide treatment.

B15 cells were cultured in a low serum containing media [5% fetal calf serum (FCS)]. These cells normally require 20% FCS. A batch of B15 cells ($2.2 \times 10^6$/ml) was cultured in RPMI containing 5% FCS. 200 µl of this suspension was seeded into each well of a 96 well culture plate. Either the antisense or sense oligonucleotides were added to the culture at a final concentration of 10 µM. The cell numbers were determined as an average of the triplicates and plotted in FIG. 14.

B15 cells cultured in low serum containing media were found to have increased survival after treatment with the 3'

BCR antisense oligonucleotide compared to sense oligonucleotide treatment. Thus, after five days of treatment with antisense 3' BCR the number of viable cells was about twice that of sense-treated cells.

These results indicate that the normal Bcr protein inhibits survival of Bcr-Abl expressing cells under serum conditions that inhibit cell growth. Thus, this result is consistent with normal Bcr protein having a negative effect on cells by stimulating cell death.

Figure 14:
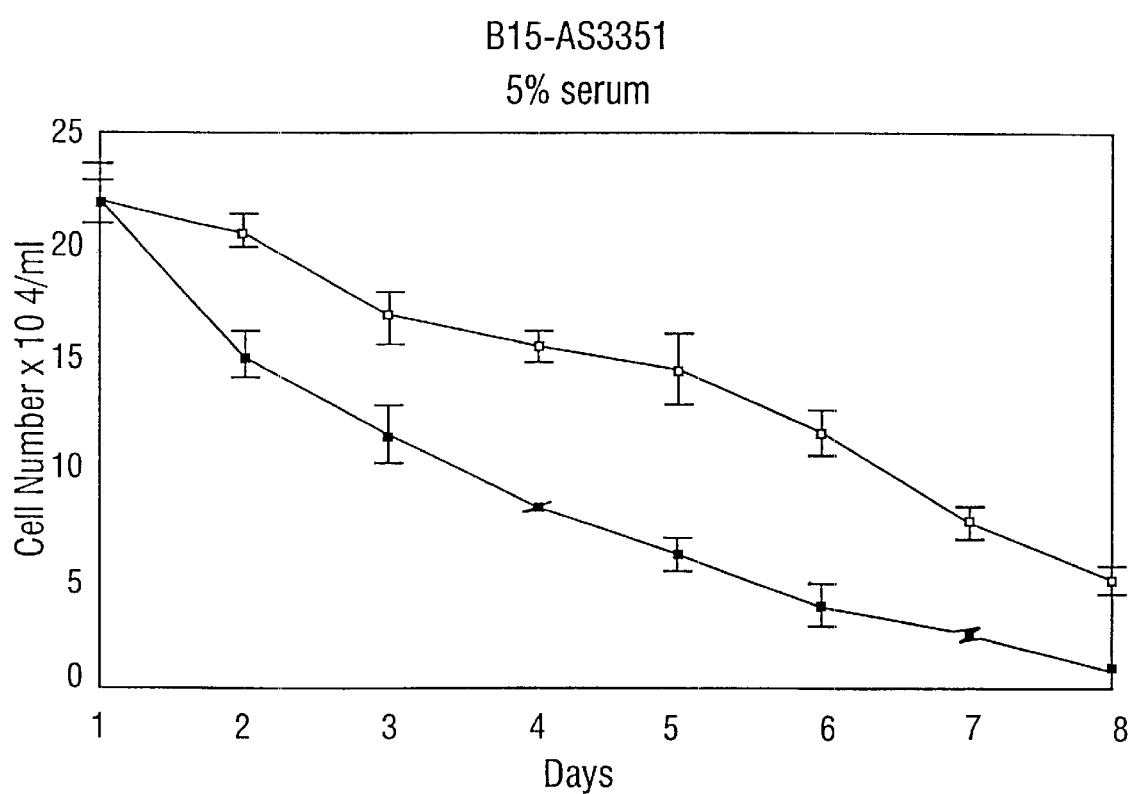
FIG. 14 shows treatment with 3' BCR anti-sense oligo enhances the survival of p185 BCR-ABL expressing SUP-B15 cells maintained in low serum. SUP-B15 cells ($2 \times 10^6$ cells) were maintained in RPMI medium containing 5% fetal calf serum. Cells will not grow under these conditions and will slowly die off since cell growth requires 20% serum. Cells were treated with the 3' BCR anti-sense (open squares) or sense oligo (closed squares) at a concentration of 10 $\mu$M. The number of viable cells was determined by trypan blue dye exclusion. The data are expressed as the mean (+/− SEM) of three replicates.

In summary, inspection of the growth rate patterns of sense and anti-sense treated Bcr-Abl expressing cultures showed that the growth stimulatory effects of anti-sense were not seen until a lag of several days. During that lag period, no differences in growth rate between sense and anti-sense treated cells were observed in two cell lines. This lag may be due to optimal growth stimulation provided by high serum concentration in the medium. Therefore, the effects of the anti-sense 3' oligo was tested at decreased levels of serum, under conditions where cells fail to increase in cell number. Anti-sense treated cultures showed enhanced survival when compared to sense (FIG. 14).

These results suggest that Bcr protein may stimulate cell death in the presence of Bcr-Abl, and that removal of Bcr will enhance survival of Bcr-Abl expressing cells.

EXAMPLE XII

Phosphorylation of Bcr Inhibits its Ser/Thr Kinase Activity and Blocks the Negative Regulatory Role of Bcr The present Example demonstrates inhibition of Ser-Thr Bcr autophosphorylation activity by Bcr-Abl. Normal Bcr protein, in addition to enhancing the growth stimulatory effects of Bcr-Abl, also has a negative regulatory role as shown herein. The present results indicate that normal Bcr counteracts the growth effects of Bcr-Abl and that this negative effect of Bcr is neutralized by tyrosine phosphorylation of Bcr by Bcr-Abl.

Bcr-Abl and Bcr appear to be in an intracellular battle. Bcr-Abl is stimulating malignant growth whereas non-tyrosine phosphorylated Bcr is inhibiting growth. Moreover, Bcr-Abl can inhibit the kinase activity of Bcr by tyrosine phosphorylation. The Ser/Thr kinase function of Bcr is presumed to be responsible for its negative growth effects. Therefore, since tyrosine phosphorylation of Bcr will inhibit its Ser/Thr kinase activity, blocking the Ser/Thr kinase function of Bcr will block its negative growth function.

Bcr-Abl catalyzed in vitro phosphorylation of Bcr (harvested from cells lacking Bcr-Abl) reduces the level of Bcr autophosphorylation. Therefore, the following study was carried out. The phosphoamino acid ratios of gel purified Bcr labeled in the immunokinase assay with [$^{32}$P] ATP with no added Bcr-Abl immune complexes was compared to that labeled with a relatively high level of Bcr-Abl immune complexes, and to that with addition of a low amount of Bcr-Abl (5% of the high level).

Figure 15:
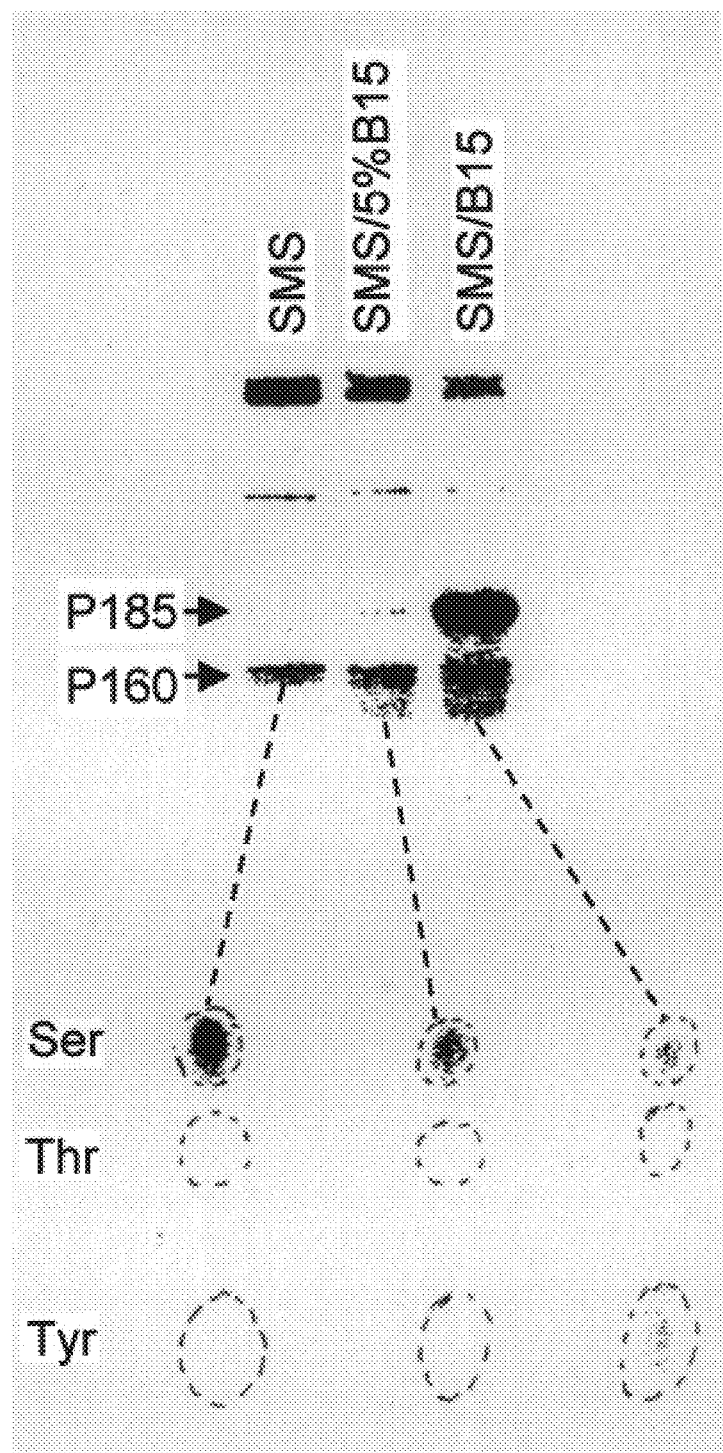
FIG. 15 shows depression of Bcr serine/threonine autokinase activity by the Bcr-Abl tyrosine kinase. (In vitro transphosphorylation of Bcr by Bcr-Abl). Equal amounts of cell extract from $3 \times 10^8$ SMS-SB cells (lacking Bcr-Abl) were divided into three portions and processed for immunoprecipitation with anti-Bcr (1256–1271). One portion (from $1 \times 10^8$ cells) was collected on protein A Sepharose beads for the immunokinase assay. The second portion ($1 \times 10^8$ cells) was added to anti-Abl(51–64) immune complexes bound to protein A Sepharose beads obtained from $1 \times 10^6$ SUP-B15 (p185 BCR-ABL expressing cells). These anti-Abl immune complexes have a high amount of p185 BCR-ABL but only a trace level of p160 BCR. The third batch of Bcr immune complexes ($1 \times 10^8$) were added to Bcr-Abl immune complexes obtained from $2 \times 10^7$ SUP-B15 cells. The whole procedure was performed as described (Liu et al., 1993). Phosphoamino acid analysis of gel purified p160 BCR following transphosphorylation by low and high levels of Bcr-Abl. The three p160 BCR bands from panel A were eluted from the gel by SDS buffer and treated with 6 N HCl for 90 min at 110° C. These conditions are a reasonable compromise to obtain both phospho serine/threonine and tyrosine values. The hydrolysate was fractionated on a thin layer plate under conditions for separating phospho serine/threonine and tyrosine (Liu et al., 1993). About 200 cpm (Cerenkov) of acid hydrolysate from the p160 SMS-SB band, 200 cpm of the SMS-SB/5% SUP-B15 p160 band, and 500 cpm of the SMS-SB/100% SUP-B15 p160 band were loaded on the plate. After normalization, the intensities of the serine/threonine spots were 4,421 for p160 Bcr alone; 1763 for p160 BCR incubated with a low level of Bcr-Abl (5%), and 142 for p160 BCR incubated with the high level of Bcr-Abl. Phospho serine/threonine was reduced more than 30-fold by Bcr-Abl kinase at relatively high levels and by 2.5-fold at the 5% Bcr-Abl level.

Addition of Bcr-Abl immune complexes to Bcr immune complexes in kinase assays showed phosphorylation of Bcr-Abl and Bcr (FIG. 15). The level of phosphorylated Bcr-Abl increased with increased levels of Bcr-Abl immune complexes, but the intensity of the phosphorylated Bcr band did not change appreciably. However, phosphoamino acid analyses of the Bcr band under these different conditions showed a dramatic decrease in the phosphoserine/threonine content of the Bcr band with a relatively low level of Bcr-Abl complexes (FIG. 15). Quantitative analyses indicated that serine/threonine autophosphorylation of Bcr was reduced more than 2.5-fold by a low level of Bcr-Abl (5%). With a high level of Bcr-Abl complexes, the level of Bcr autophosphorylation was reduced about 30-fold.

These results indicate that the level of tyrosine phosphorylation of Bcr may be directly correlated with the level of inhibition of Bcr autophosphorylation activity.

Figure 16:
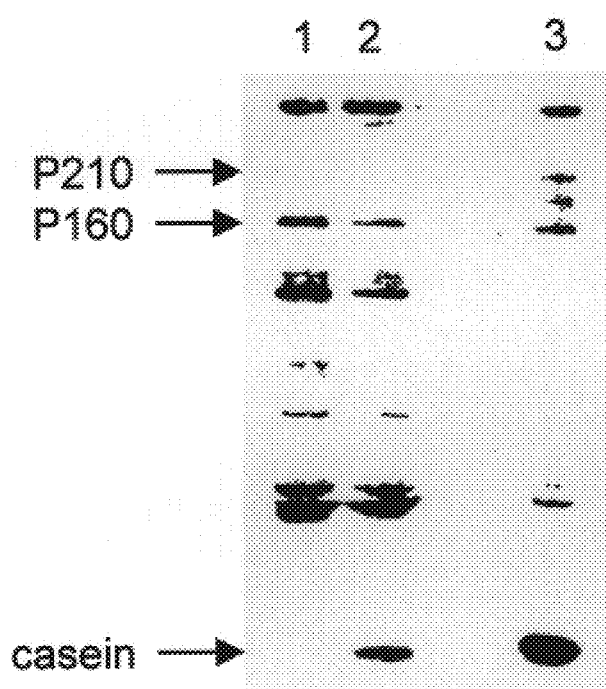
FIG. 16 shows transphosphorylation of casein by Bcr and Bcr/Abl. T-150 flasks of COS 1 cells were transfected with either pSG5 BCR or pSG5 BCR-ABL. Two days after transfection, cells were harvested and the kinase performed as in Liu et al., 1993. In lane 3, the same amount of protein A Sepharose beads with Bcr complexes as in lane 2 was added to protein Sepharose beads with Bcr-Abl complexes harvested with anti-Abl (51–64) p6D monoclonal antibody. Casein (10 $\mu$g) was added to each reaction mixture along with the labeled ATP. After 15 min on ice, the reaction was stopped and the sample treated with hot SDS sample buffer. After removal of the protein A Sepharose beads, the supernatant fluid was fractionated on a 8% SDS gel. Lane 1, p160 BCR autophosphorylation in the absence of casein; lane 2, transphosphorylation of added casein by Bcr, lane 3, transphosphorylation of casein by a mixture of p160 BCR and p210 BCR-ABL.
Figure 17:
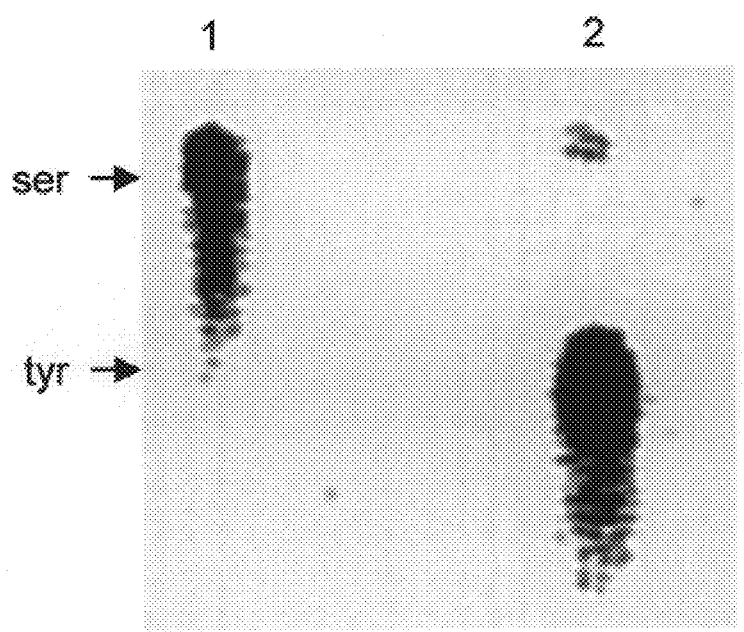
FIG. 17 shows phosphoamino acid analysis of casein phosphorylated by Bcr and Bcr/Bcr-Abl. Approximately equal cpm of casein from each of the reaction mixtures was treated with 6N HCl for 90 min to favor detection of both phosphoserine/threonine and phosphotyrosine. Casein phosphorylated by Bcr is shown in lane 1; lane 2 shows the analysis of casein phosphorylated by the Bcr/Bcr-ABl mixture. Despite the presence of equal amounts added Bcr kinase, serine phosphorylation of casein by Bcr was severely inhibited by added Bcr-Abl. That Bcr-Abl was present and active is shown by the strong signal of phosphotyrosine in the added casein molecules in the presence of Bcr-Abl.

Studies were performed to determine whether the transphosphorylation function of Bcr was similarly inhibited by Bcr-Abl catalyzed tyrosine phosphorylation (FIG. 16 and FIG. 17). In these studies, casein (10 μg) was added to the kinase reaction mixtures to allow transphosphorylation of the added substrate by Bcr or by Bcr mixed in vitro with Bcr-Abl (FIG. 16 and FIG. 17).

The results showed that transphosphorylation of casein by Bcr was quite effective (FIG. 16, compare lanes 1 and 2). Moreover, phosphoamino analysis established that casein was phosphorylated on serine and threonine residues (FIG. 17, lane 1).

Of interest, although the phosphorylation of added casein was stimulated when Bcr-Abl was added to Bcr (FIG. 16, lane 3), the level of casein serine/threonine phosphorylation was greatly inhibited while at the same time casein was strongly phosphorylated on tyrosine residues (FIG. 17, lane 2). These results show quite clearly that the Bcr-Abl oncoprotein inhibits the transphosphorylation function of normal Bcr.

These results support the hypothesis that Bcr-Abl may in fact be able to neutralize the negative effects of Bcr by tyrosine phosphorylation of first exon sequences within Bcr. It is the first exon of Bcr that functions as a Ser/Thr protein kinase. Several tyrosines within or near the kinase domain of Bcr are phosphorylated by Bcr-Abl. The kinase domain of Bcr would include residues 163–355 (Campbell and Arlinghaus, 1991); the present disclosure demonstrates that tyrosines at positions 177, 283 and 360 are phosphorylated within the normal Bcr protein as a result of Bcr-Abl catalyzed phosphorylation. Several other first exon tyrosines are likely to be phosphorylated also. One or more of these tyrosine phosphorylations might change the shape of the Bcr protein in a way that inhibits its serine/threonine kinase activity.

EXAMPLE XIII

Expression of Bcr Fragments

Materials and Methods: COS1 cells ATCC #CRL 1650 (Rockville, Md.) COS1 is a fibroblast-like cell line established from simian kidney cells (CV1) that were transformed by an origin-defective mutant of SV40, that codes for wild-type T antigen. COS1 cells were cultured at 37° C. with 5% $CO_2$ in DMEM (Grand Island Biological Co. (Gibco) Grand Island, N.Y.) supplemented with 10% fetal calf serum (Gibco Laboratories, Grand Island, N.Y.).

Transient transfections of COS1 cells were performed by the diethylaminoethyl (DEAE)-Dextran procedure. Transfection was initiated when COS1 cells were about 60%–80% confluent. After washing once with phosphate-buffered saline (PBS) and once with Tris-buffered Saline-0.02% Dextrose (TBS-D), cells were incubated with TBS-D containing 0.2 mg/ml DEAE-Dextran and 2 μg/ml of each added plasmid. The supernatant was then removed after 5–10 minutes when the cells started to round up and shrink.

After washing once with TBS-D and once with PBS, the cells were incubated in DMEM supplemented with 10% fetal calf serum and 100 μg/ml of chloroquine at 37° C. The chloroquine containing media was removed after 3–5 hours and the cells were washed three times with DMEM without fetal calf serum. The cells were then incubated in DMEM supplemented with 10% fetal calf serum at 37° C. for 2–3 days before harvesting.

Figure 6A:
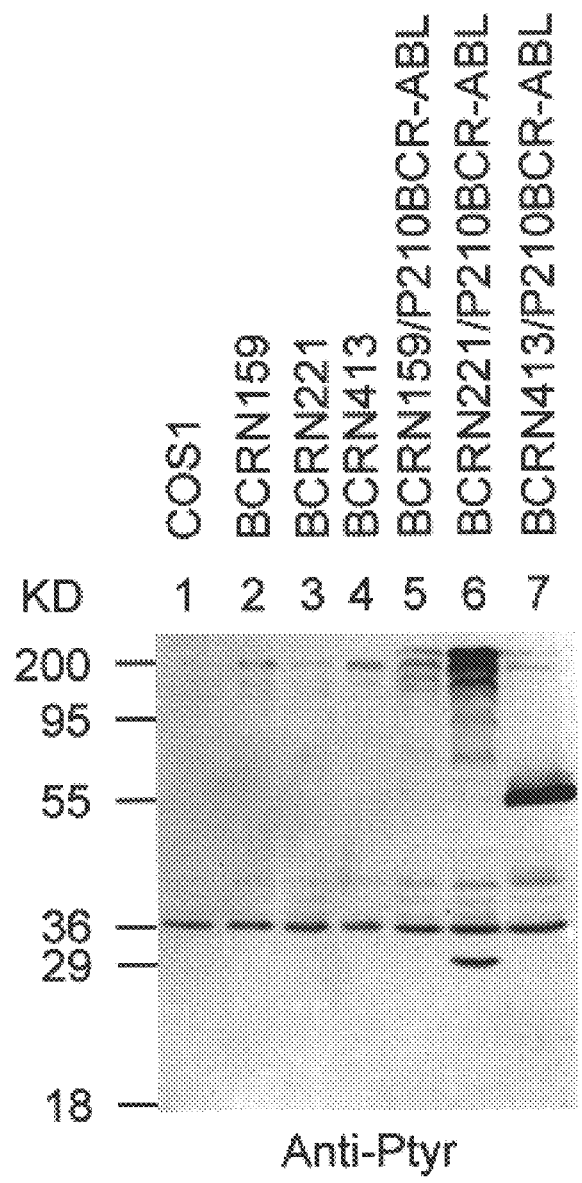
FIG. 6A and FIG. 6B. In vivo tyrosine phosphorylation of truncated Bcr first exon sequences by Bcr-Abl. COS-1 vectors expressing Bcr150, Bcr221, and Bcr413 proteins, respectively, were expressed in COS-1 cells in the presence and absence of p20 Bcr-Abl.

COS-1 vectors expressing Bcr159, Bcr221, and Bcr413 proteins, respectively, were expressed in COS-1 cells in the presence and absence of p210 Bcr-Abl. FIG. 6A shows a Western blot with Anti-pTyr antibody. Bcr-Abl induces tyrosine phosphorylation of Bcr221 and Bcr413 but not Bcr159, indicating that the first two tyrosines of Bcr are not targets for Bcr-Abl.

Figure 6B:
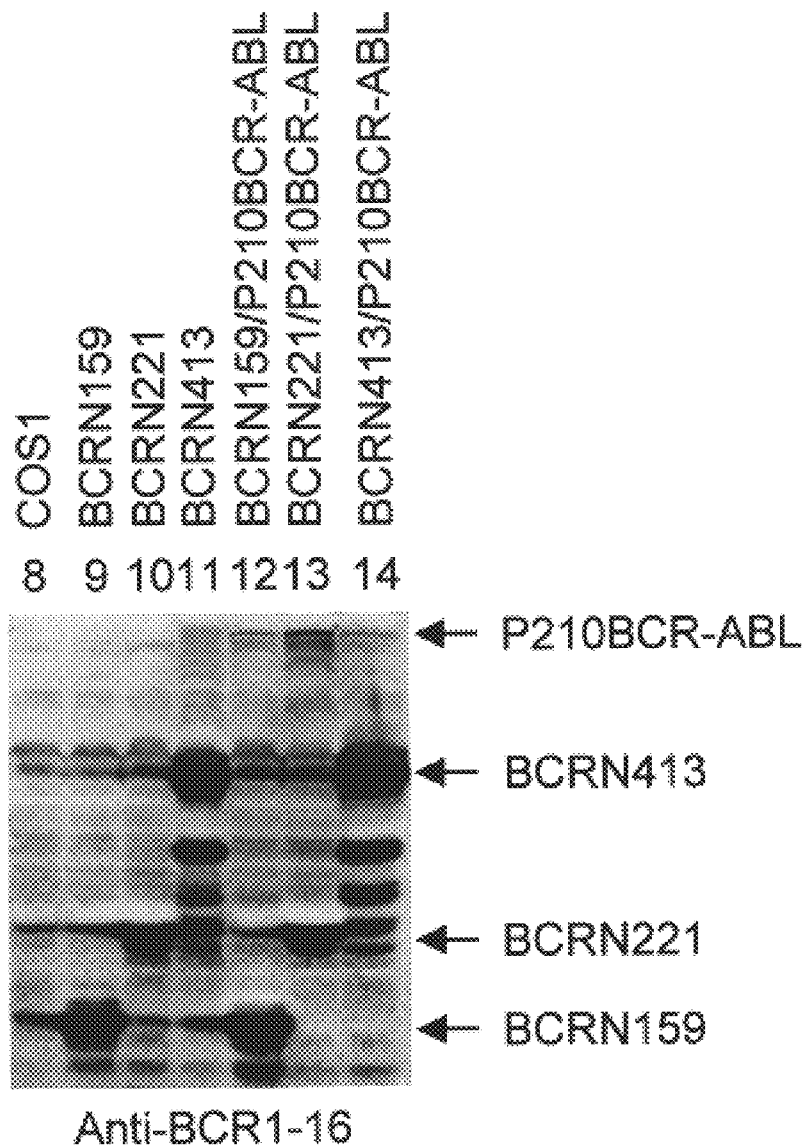

The next tyrosine is at residue 177, and it is expected to be phosphorylated by Bcr-Abl (Pendergast et al., 1993). Bcr221 is tyrosine phosphorylated, but as with Bcr413, only in the presence of Bcr-Abl. FIG. 6B shows a Western Blot of the same extracts probed with anti-Bcr 1–16. Note that all three Bcr proteins fragments are specifically expressed under both conditions.

In summary, Bcr159 is not phosphorylated in cells expressing Bcr-Abl despite the presence of two tyrosines (FIG. 6A and FIG. 6B). In contrast, a 221 residue N-terminal fragment and a 413 N-terminal fragment of Bcr are expressed and both are phosphorylated on tyrosine 177 in cells expressing Bcr-Abl.

EXAMPLE XIV

Delivery of BCR-ABL Peptides via Retrovirus

This example describes the use of the invention in the treatment of leukemia where Philadelphia positive cells are present.

Nucleic acid sequences encoding BCR peptides or fusion proteins are introduced into bone marrow to provide a copy of a BCR synthetic gene and therefore, also a protein product comprising BCR peptides or fusion peptides that would bind to adapter proteins and inhibit the ras oncogene pathway, and bind to the coiled coil area of BCR-ABL to inhibit autophosphorylation.

Figure 11:
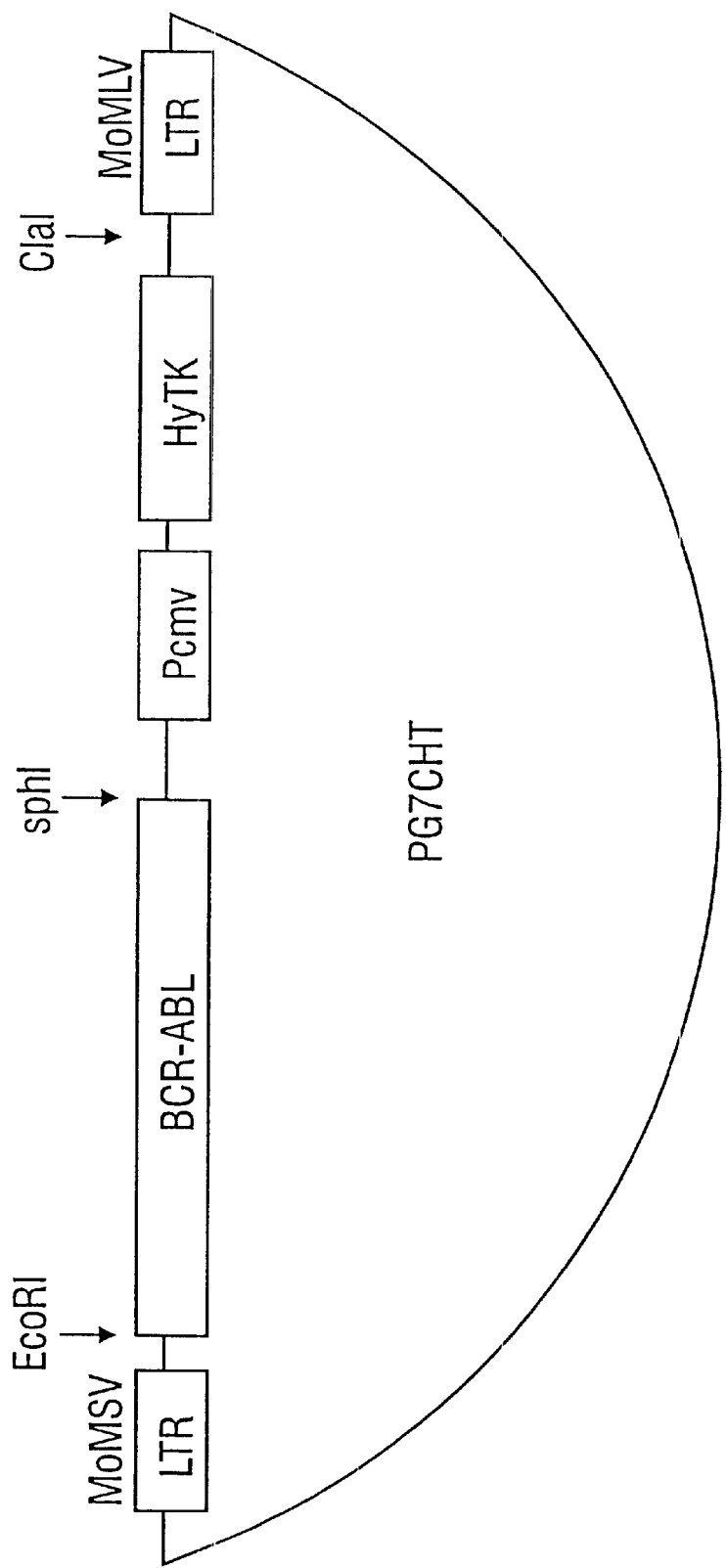
FIG. 11 depicts a retroviral vector pG7CHT useful for introducing peptides of the present invention into cells.

A retroviral vector pG7CHT (FIG. 11) containing the BCR-ABL gene was obtained from Dr. Albert Deisseroth. The pA317 amphotropic retrovirus packaging cell line (American Type Culture Collection, Rockville, Md., #CRL9078) is used for producing high titer virus. The BCR-ABL gene is released from the plasmid by digesting with EcoRI and SphI restriction endonucleases. A full length BCR gene released from pSG5BCR plasmid by digesting with EcoRI and SphI restriction enzymes is then inserted into the EcoRI and SphI sites of pG7CHT vector. The BCR gene is expressed under MoMSV/LTR. The vector also contains a hyromycin resistant gene (HyTK) which is expressed under a CMV promotor (Pcmv). The N-terminal fragments of BCR is expressed using the same strategies described above.

The Bcr 421 fragment interferes with Bcr-Abl oligomerization and contains all the phosphorylation sites of native Bcr-Abl. Therefore, overexpression of this fragment has all the inhibitory activities of the first exon of Bcr. However, it will not directly interfere with Shc and Crkl effects but because it will inhibit oligomerization of Bcr-Abl, the kinase activity of Bcr-Abl is greatly reduced. Therefore, Crkl and Shc should not be tyrosine phosphorylated to any great extent.

Note that full length BCR with stop codons in all three reading frames at codon 422 was inserted into the vector. Therefore, only the 421 fragment is made. Similarly, the Bcr159 fragment and the Bcr 221 fragment were made by inserting stop codons after codon 159 and 221, respectively.

EXAMPLE XV

Treating a Bone Marrow Sample with Bcr-Abl Peptides to Selectively Inhibit Philadelphia Chromosome-Positive Cells The present example outlines autologous bone marrow purging to remove leukemic (Philadelphia chromosome-positive) cells in vitro prior to in vivo injection. This method may also advantageously enrich the bone marrow population of diploid (normal) cells, thus enhancing the therapeutic capacity in the leukemic patient to whom it is administered.

As used in the present example, a "normal cell" is a cell in bone marrow which is Philadelphia chromosome-negative. A "normal cell" is also defined as a bone marrow cell which is dependent upon ABL within the cell for growth.

Accordingly, a bone marrow sample of at least 1000 ml. containing $2 \times 10^{10}$ or $2 \times 10^8$/kg of nucleated cells is collected under sterile conditions from a leukemic patient. The sample is then subjected to Ficoll hypaque or Percoll discontinuous gradient separation. The nucleated cells (immature) are collected from the interface. This reduces the number of nucleated cells 5-fold (to $4 \times 10^7$/kg). The cells are then subjected to antibody separation by removing DR (Class II HLA antigen family expressed in dividing hematopoietic cells) positive cells by immunoadherance separation. This reduces the number of cells to $2-5 \times 10^7$ cells. These remaining cells are then resuspended at $5 \times 10^5$ cells per cc of tissue culture medium (40–100 cc) of HL1 medium, supplemented with 1000 U of GMCSF and IL3, and incubated with BCR peptides for 3 days.

The Bcr-Abl peptides (or phosphopeptides), e.g., packaged in liposomes, are then added to a cell culture of bone marrow cells and cell supportive culture medium at a concentration of between 1 and 100 $\mu$M. The BCR peptides, most preferably, are to be added to the bone marrow cell culture system at a concentration of 10 $\mu$M. After approximately 3 days in culture, changing the medium daily, the culture is examined to determine the ratio of leukemic cells to normal cells.

A ratio of not more than 1 leukemic cell 100 normal cells is considered acceptable for use as a therapeutic bone marrow transplant for a leukemic patient. This ratio was chosen as clinical studies have shown that reduction of the ratio of normal cells to leukemia cells significantly below 100 to 1 respectively, leads to prolonged remissions post transplant.

"Purged", Philadelphia chromosome-positive cell-depleted, diploid cell-"enriched" (Philadelphia chromosome-negative cell) autologous bone marrow samples, as processed above, are then reintroduced into the transplant recipient patient.

EXAMPLE XVI

Method of Treating Leukemia In Humans with BCR Peptide-Treated Tissue Transplants The present example describes methods of using BCR peptide therapy for treating leukemia. Specifically, the use of BCR peptide therapy in methods for the processing and purging of bone marrow samples that contain Philadelphia chromosome-positive cells is described. According to one embodiment, the treated tissue is enriched for Philadelphia chromosome-negative cells, and may be reintroduced into the leukemic animal as an autologous transplant. As such, a therapeutic tool to treat a patient with leukemia is provided.

As part of a total clinical treatment protocol for a patient, the method provides at least a two-log (100-fold) reduction in the ratio of leukemic cells to normal cells, in addition to the 10,000/1 to 1/1 reduction (from chemotherapy) and the 2-log reduction (from fractionation of the marrow cells subsequent thereto) of leukemia cells to normal cells which may be achieved with conventional treatment regimens with non-pre-treated bone marrow tissue transplants.

The regimen thereby effectively reduces the number of leukemia cells in the patient to levels which enhance the therapeutic index of the bone-marrow transplant treatment. In some cases, an up to 3-log reduction (1000-fold) in the number of Philadelphia chromosome-positive cells in a patient's bone marrow cell population is achievable upon the reintroduction of a pretreated bone marrow sample.

The reintroduction of a patient's pre-treated autologous bone marrow sample also offers a method for curing CML disease and for preventing the transition of leukemia from its chronic phase to the more serious forms of acute leukemia. A processed autologous bone marrow sample according as described herein depletes the Philadelphia chromosome-positive population of marrow cells while enriching the population of normal hematopoietic progenitor cells (diploid cells) of the tissue sample.

Once a prepared bone marrow sample is processed according to the methods disclosed herein, standard protocols employed for the general technique of performing a bone marrow transplant in CML may be used to obtain an initial bone marrow sample and to reintroduce the processed bone marrow to the patient. Such general clinical techniques are described by Canaani et al. (1990), which reference is specifically incorporated herein by reference for this purpose. A volume of about 50–100 cc of purified marrow (containing about $2.5 \times 10^7$ cells) is the volume of processed bone marrow tissue which is given to the patient to effect the claimed treatment.

Preferred Patient Profile Eligibility

The following presents a generalized patient profile defining those characteristics most desirable in a prospective BCR-peptide-therapy patient.

1. Interferon refractory CML patients in initial chronic phase, or second chronic phase after accelerated phase or blast crisis are particularly well suited for therapy according to the presently described invention. Patients who have bone marrow collected and stored in the chronic phase, or who have been reinduced into chronic phase, are particularly preferred as treatment subjects.

2. Patients most preferably should be off interferon therapy for about four weeks prior to storage of an autologous bone marrow sample to be pre-treated with BCR-peptides. However, prior treatment with interferon does not disqualify a patient from eligibility for the BCR-peptide therapy where such a regimen had been discontinued at least four weeks prior to bone marrow sampling.

3. Patients must have a performance of <3 on the Zubrod scale (see Table 2—Zubrod Scale), a creatinine level less than 1.6 mg %, acceptable cardiac condition (class I or II), normal liver functions with bilirubin less than 2 mg %, and an acceptable pulmonary condition (FEV and DLCO >50% of predicted). Patients should be free of infections at the time of treatment.

TABLE 2

| Zubrod Scale | |
|---|---|
| Performance Status | Activity |
| 0 | No signs or symptoms |
| 1 | Minor signs or symptoms |
| 2 | Ambulatory > 50% of time |
| 3 | Ambulatory < 50% of time |
| 4 | Bedridden |

4. A serum creatinine less than 1.6 and SGOT within the normal range is requires.

Treatment Plan

1. Bone marrow aspiration and collection of peripheral blood stem cells and storage: Bone marrow is aspirated according to standard techniques and stored when the patient is in an initial chronic phase or after reinduction into chronic phase by chemotherapy. In vivo (chemotherapy) methods are used to reduce the level of Philadelphia chromosome-positive cells in the population of transplanted cells, following which the marrow is collected and treated with BCR-peptides.

2. The procedure for BCR-peptide treatment is as follows:

a. The nucleated cells of the bone marrow sample (approximately $1.4 \times 10^{10}$ nucleated cells for a 70 kg weight human patient) are concentrated on a ficoll hypaque gradient to remove cells of limited proliferative capability (this reduces the total number of cells by 5-fold).

The remaining (approximately $2.8 \times 10^9$) cells are then further treated with SEPHAROSE® beads conjugated with antibodies to DR antigens. Preparations of marrow thus treated have been observed to generate rapid hematopoietic recovery. This reduces the total number of cells by 10-fold ($2.8 \times 10^8$). The cells are then diluted in 50 cc of HL1 medium supplemented with 1,000 units of GMCSF and IL-3 (concentration of cells is $5.6 \times 10^6$/cc).

b. The cells are incubated for three days in sterile medium at 37° C. in the presence of 10 mM of each BCR-peptide as liposomes.

c. Following rinsing, the BCR-peptides are washed from the cells.

The cells are then cryopreserved by standard procedures.

If this or other in vitro techniques are not available for removing Philadelphia chromosome-positive cells, a combination of peripheral blood and marrow may be utilized which has been collected in chronic phase, or which has been collected following reinduction of chronic phase in the patient with chemotherapy. Multiple bone marrow aspirations from the patient's iliac crests are performed before the administration of such agents as cytoxan, VP-16 and TBI. A second bone marrow storage is considered if less than $4 \times 10^8$ total nucleated cells/kg are collected, $2 \times 10^8$ cells/kg of which are used for the BCR peptide incubation and $2 \times 10^8$ cells/kg of which are used as a back-up.

Another criterion for adequacy of the amount of nucleated cells of a marrow sample collected from a patient is $4 \times 10^4$ CFUGM/kg.

Alternatively, cells from the peripheral blood may be collected for reconstitution as a back-up. A dose of $6 \times 10^8$ mononuclear cells/kg from the peripheral blood or $2 \times 10^4$/kg CFUGM is required as a back-up.

Treatment Plan

The preparative marrow ablative regimen comprises the following systemic chemotherapy:

Cyclophosphamide: 60 mg/kg in 0.5 liter D5W intravenously over 3 hours daily for 2 days—days 1 to 2 (total 120 mg/kg).

VP-16: 125 mg/m2 in 1 liter of normal saline is administered intravenously over 3 hours every 12 hours daily ×3 (6 doses on days 1–3) (total 750 mg/m$^2$).

The hydration given along with the VP16 and cyclophosphamide is 4 liters every 24 hours, as tolerated. This is supplemented as necessary to maintain intravascular fluid volume and urine output of the patient.

Total Body Irradiation: Total body irradiation is about 1020 centrigrays. The patients are placed in the supine position and the TBI is directed from the right side with a calculated mid plane dose of 170 rads/fraction, each fraction even bid starting on day 6–8. Autologous bone marrow is then reinfused on day 9 after the last dose of TBI, after premedication with benadryl 25 mg and solucortef 100 mg 30 minutes before reinfusion to prevent anaphylactic reactions.

Treatment in a 12LP (Protected Environment) is most preferred. Patients will most preferably remain there until the attainment of 500 granulocytes/mm$^3$. Patients will receive bactrim DS po BID and ketoconazole 200 mg poq8h while hospitalized. All blood products are irradiated from the start of treatment and for three months following transplantation.

Maintenance Therapy: Interferon maintenance therapy begins 6 weeks after engraftment (a return of the platelet count to greater than 0000/deciliter and an absolute granulocyte count greater than 2,000/deciliter); at a dose of 3 to 9×10$^6$ units, the dose to be adjusted to keep to WBC counts between 2 and 4×10$^3$/μl with a platelet count >50×10$^3$/μl.

Pre-Treatment Evaluation Bone marrow aspirate and biopsy for morphology, pathology and cytogenetics are most preferably be obtained prior to treatment. An EKG and CXR is performed on all patients. A urinalysis ia also obtained before therapy. Pulmonary function studies with diffusion capacity, where permitted, are also conducted.

Evaluation During Study CBC, platelet, and differential measurements are obtained every 1–2 days during the initial induction.

Bone marrow aspirate and biopsy for morphologic pathology are performed at marrow recovery (when WBC count >1.5 K/μl).

Upon marrow recovery, a full work-up including CBC, platelet count and differential, SMA 12, and marrow studies including cytogenetics are performed. Studies at remission include CBC, platelet count, differential and SMA 12 every 1–4 weeks, marrow studies with cytogenetics every 1–3 months and as indicated by disease status.

Criteria for Response and Toxicity Criteria for response are similar for all phases of disease as follows:

Complete hematologic remission—normalization for at least 4 weeks of the bone marrow (less than 5% blasts) and peripheral blood with WBC <10×10$^3$/μl and no peripheral blasts, promyelocytes or myelocytes. This is in addition to disappearance of all signs and symptoms of the disease.

Complete hematologic remission is further classified according to suppression of the Philadelphia chromosome (Ph) as:

a) no cytogenetic response—Ph positive 100%
b) minimal cytogenetic response—Ph positive 35–95%
c) partial cytogenetic response—Ph positive 5–30%
d) complete cytogenetic response—Ph positive 0%

This is done after a total neutrophil count of 1000/mm$^3$ has been achieved after transplant and at 6-month intervals, thereafter.

Progressive disease is defined for purposes of the present invention as an increase in the WBC count to greater than 40×10$^3$/μl in chronic phase, or the appearance of features of accelerated disease or blastic crisis. All patients treated will be valuable for both toxicity and response.

TABLE 3

Evaluation Before and During Therapy

| | Pretreatment | Every 2–3 days | When WBC count > 1.5 K/μl every 1–3 months in remission |
|---|---|---|---|
| History, physical exam | X | — | — |
| CBC, differential and platelet counts | X | X | X |
| SMA12, PT. PTT, Fib, FSP, electrolytes* | X | X | X |
| Bone marrow aspirate and biopsy | X | — | X |
| Bone marrow cytogenetics* | X | — | X |
| EKG, CXR, urinalysis* | X | — | — |
| Pulmonary function test | X | — | — |

*In addition as indicated by clinical and hematologic situations

The patient may be given subsequent processed autologous bone marrow transplants to supplement and/or further reduce the ratio of leukemic cells:normal cells in the bone marrow and peripheral blood.

EXAMPLE XVII

In vivo Treatment of Philadelphia Chromosome-Positive Leukemia Patients

Either liposome/Bcr-Abl peptides (tyrosine phosphorylated or not where appropriate) or retrovirus vectors that express p160 BCR or BCR N-T fragments) are injected i.v. periodically (daily or twice weekly) to treat leukemia. The dose of liposome/peptides is 100 μMoles of each peptide per 10 kg of body weight. The dose of virus is 10$^9$ infectious units per 150 kg body weight. Patients are monitored as above for chemical response.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adelman et al., DNA, 2:183, 1983.
Arlinghaus et al., In: *UCLA Symposia on Molecular and Cellular Biology New Series, Acute Lymphoblastic Leukemia*, Eds. R. P. Gale, D. Hoelzer, New York, N.Y., Alan R. Liss, Inc., 108:81–90, 1990.
Bailey, *Methods in Molecular Biology* 1. *Proteins*, Ed. J. M. Walker, Humana Press, Clifton, N.J. p. 325–333, 1984.
Bolton, "Radioiodination Techniques" Amersham International, Amersham, Bucks, England, 1977.
Campbell and Arlinghaus, "Current Status of Bcr Gene Involvement with Human Leukemia", In: *Advances in Cancer Research*, Eds. Klein, VandeWoude, Orlando, Fla. Academic Press, Inc., 57:227–256, 1991.
Campbell et al., *Oncogene*, 5:773–776, 1990.
Canaani et al., In: *Chronic Myelogenous Leukemia: Molecular Approaches to Research and Therapy*, Deisseroth, A. and Arlinghaus, R. (Eds.), Marcel Dekker Inc., pp. 217–241, 1990.
Crea et al., *PNAS*, 75:5765, 1978.
Druker et al., *Blood*, 79:2215–2220, 1992.
Fioretos et al., *Oncogene*, 8:2853–2855, 1993.
Hunter and Greenwood, *Nature*, 194:495–496, 1962.
Kasahara, Dozy & Kan, *Science*, 266:1373–1376, 1994.
Kotin, *Human Gene Therapy*, 5:793:801, 1994.
Kyte and Doolittle, *J. Mol. Biol.*, 157:105, 1982.
Liu et al., *Oncogene*, 8:101–109, 1993.
Maldini et al., *Mol. Cell. Biol.*, 6:1803–1811, 1986.
Marchalonis, *Biochem. J.*, 113:299–305, 1969.
Maru and Witte, *Cell*, 67:459468, 1991.
McWhirter and Wang, *Mol. Cell. Biol.*, 11:1553–1565, 1991.
McWhirter et al., *Mol. Cell Biol.*, 13:7587–7595, 1993.
Merrifield, *J. Am. Chem. Soc.*, 85:2149, 1963.
Messing et al., Third Cleveland Symposium on Macromolecules and Recombinant DNA. Editor: 'A. Walton, Elsevier Amsterdam, 1981.
Miller, *Curr. Top. Microbiol Immunol.* 158:1, 1992.
Pawson et al., *Cell*, 71:359–362, 1992.
Pendergast et. al., *Cell*, 66:161–171, 1991.
Pendergast et al., *Cell*, 75:175–185, 1993.
Puil et al., *EMBO Journal*, 13(4):764–773, 1994.
Reichman et al., *Cell Growth amd Differ.*, 3:451–460, 1992.
Sambrook et al., *Molecular Cloning: A Laboratory Manual*, Ed. 2, Cold Spring Harbor, N.Y., Cold Spring Harbor Laboratory, 1989.
Stewart et al., *Hum. Gene Ther.*, 3:267, 1992.
Tauchi et al., *J. Exp. Med.*, 179:167–175, 1994.
Ten Hoeve et al., *Blood*, 84(6):1731–1736, 1994.
Ten Hoeve et al., *Oncogene*, 8:2469–2474, 1993.
Torchilin et al., *FASEBJ.* 6:2716, 1992.
Zhu, et al., *Science*, 261:209–211, 1993.
U.S. Pat. No. 4,554,101

---

What is claimed is:

1. An expression vector comprising a DNA sequence that expresses a peptide or polypeptide comprising 4 to 426 contiguous amino acids from SEQ ID NO: 1 that includes tyrosine 177, tyrosine 283 or tyrosine 360, and no contiguous amino acids from abl.

2. The vector of claim 1, further defined as a retroviral vector.

3. The vector of claim 1, further defined as an adenoviral vector.

4. The vector of claim 1, further defined as a plasmid associated with a liposome.

5. An expression vector comprising a nucleic acid sequence encoding a peptide or polypeptide comprising 4 to 426 contiguous amino acids from SEQ ID NO: 1, including serine 354, and no contiguous amino acids from abl.

6. The expression vector of claim 5, wherein the peptide or polypeptide further includes tyrosine 360.

7. The expression vector of claim 5, wherein the peptide or polypeptide is about 25 amino acids in length.

8. The expression vector of claim 7, wherein the peptide or polypeptide is about 30 amino acids in length.

9. The expression vector of claim 8, wherein the peptide or polypeptide is about 35 amino acids in length.

10. The expression vector of claim 9, wherein the peptide or polypeptide is about 40 amino acids in length.

11. The expression vector of claim 10, wherein the peptide or polypeptide is about 45 amino acids in length.

12. The expression vector of claim 11, wherein the peptide or polypeptide is about 50 amino acids in length.

13. The expression vector of claim 12, wherein the peptide or polypeptide is about 75 amino acids in length.

14. The expression vector of claim 13, wherein the peptide or polypeptide is about 100 amino acids in length.

15. The expression vector of claim 5, wherein the peptide or polypeptide comprises SEQ ID NO:10.

16. The expression vector of claim 5, wherein the peptide or polypeptide comprises SEQ ID NO:22.

17. The expression vector of claim 5, wherein the vector is a viral vector.

18. The expression vector of claim 17, wherein the vector is a retroviral vector.

19. The expression vector of claim 17, wherein the vector is an adenoviral vector.

20. The expression vector of claim 5, wherein the vector is associated with a liposome.

21. An expression vector comprising a nucleic acid sequence encoding a peptide or polypeptide comprising SEQ ID NO:10 or SEQ ID NO:22, and no contiguous amino acids from abl.

22. A viral vector comprising a nucleic acid sequence encoding a peptide or polypeptide comprising 4 to 426 contiguous amino acids from SEQ ID NO:1, including serine 354 and tyrosine 360, and no contiguous amino acids from abl.

* * * * *

SEQUENCE LISTING

```
<160> NUMBER OF SEQ ID NOS:  28

<210> SEQ ID NO 1
<211> LENGTH: 426
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 1

Met Val Asp Pro Val Gly Phe Ala Glu Ala Trp Lys Ala Gln Phe Pro
  1               5                  10                  15

Asp Ser Glu Pro Pro Arg Met Glu Leu Arg Ser Val Gly Asp Ile Glu
                 20                  25                  30

Gln Glu Leu Glu Arg Cys Lys Ala Ser Ile Arg Arg Leu Glu Gln Glu
             35                  40                  45

Val Asn Gln Glu Arg Phe Arg Met Ile Tyr Leu Gln Thr Leu Leu Ala
 50                  55                  60

Lys Glu Lys Lys Ser Tyr Asp Arg Gln Arg Trp Gly Phe Arg Arg Ala
 65                  70                  75                  80

Ala Gln Ala Pro Asp Gly Ala Ser Glu Pro Arg Ala Ser Ala Ser Arg
                 85                  90                  95

Pro Gln Pro Ala Pro Ala Asp Gly Ala Asp Pro Pro Pro Ala Glu Glu
                100                 105                 110

Pro Glu Ala Arg Pro Asp Gly Glu Gly Ser Pro Gly Lys Ala Arg Pro
            115                 120                 125

Gly Thr Ala Arg Arg Pro Gly Ala Ala Ala Ser Gly Glu Arg Asp Asp
        130                 135                 140

Arg Gly Pro Pro Ala Ser Val Ala Ala Leu Arg Ser Asn Phe Glu Arg
145                 150                 155                 160
```

-continued

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
                260                 265                 270

Pro Leu Glu Tyr Gln Pro Tyr Gln Ser Ile Tyr Val Gly Gly Met Met
            275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
            340                 345                 350

Val Ser Pro Ser Pro Thr Thr Tyr Arg Met Phe Arg Asp Lys Ser Arg
        355                 360                 365

Ser Pro Ser Gln Asn Ser Gln Gln Ser Phe Asp Ser Ser Ser Pro Pro
    370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile Trp Pro Asn
                405                 410                 415

Asp Gly Glu Gly Ala Phe His Gly Asp Ala
                420                 425

<210> SEQ ID NO 2
<211> LENGTH: 63
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Met Val Asp Pro Val Gly Phe Ala Glu Ala Trp Lys Ala Gln Phe Pro
1               5                   10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu
    50                  55                  60

<210> SEQ ID NO 3
<211> LENGTH: 71
<212> TYPE: PRT
<213> ORGANISM: Artificial Sequence

```
<220> FEATURE:
<223> OTHER INFORMATION: Description of Artificial Sequence: Synthetic
      Peptide

<400> SEQUENCE: 3

Met Val Asp Pro Val Gly Phe Ala Glu Ala Trp Lys Ala Gln Phe Pro
 1               5                  10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp
 65                  70

<210> SEQ ID NO 4
<211> LENGTH: 31
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Val Gly Asp Ile Glu Gln Glu Leu Glu Arg Cys Lys Ala Ser Ile Arg
 1               5                  10                  15

Arg Leu Glu Gln Glu Val Asn Gln Glu Arg Phe Arg Met Ile Tyr
            20                  25                  30

<210> SEQ ID NO 5
<211> LENGTH: 159
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Met Val Asp Pro Val Gly Phe Ala Glu Ala Trp Lys Ala Gln Phe Pro
 1               5                  10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
 65                  70                  75                  80

Ala Gln Ala Pro Asp Gly Ala Ser Glu Pro Arg Ala Ser Ala Ser Arg
            85                  90                  95

Pro Gln Pro Ala Pro Ala Asp Gly Ala Asp Pro Pro Ala Glu Glu
        100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ser Gly Glu Arg Asp Asp
    130                 135                 140

Arg Gly Pro Pro Ala Ser Val Ala Leu Arg Ser Asn Phe Glu
145                 150                 155
```

```
<210> SEQ ID NO 6
<211> LENGTH: 221
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 6

Met Val Asp Pro Val Gly Phe Ala Glu Ala Trp Lys Ala Gln Phe Pro
 1               5                  10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80

Ala Gln Ala Pro Asp Gly Ala Ser Glu Pro Arg Ala Ser Ala Ser Arg
                85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
        115                 120                 125

Gly Thr Ala Arg Arg Pro Gly Ala Ala Ser Gly Glu Arg Asp Asp
    130                 135                 140

Arg Gly Pro Pro Ala Ser Val Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
            180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser
    210                 215                 220

<210> SEQ ID NO 7
<211> LENGTH: 413
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 7

Met Val Asp Pro Val Gly Phe Ala Glu Ala Trp Lys Ala Gln Phe Pro
 1               5                  10                  15

Asp Ser Glu Pro Pro Arg Met Glu Leu Arg Ser Val Gly Asp Ile Glu
            20                  25                  30

Gln Glu Leu Glu Arg Cys Lys Ala Ser Ile Arg Arg Leu Glu Gln Glu
        35                  40                  45

Val Asn Gln Glu Arg Phe Arg Met Ile Tyr Leu Gln Thr Leu Leu Ala
    50                  55                  60

Lys Glu Lys Lys Ser Tyr Asp Arg Gln Arg Trp Gly Phe Arg Arg Ala
65                  70                  75                  80
```

-continued

```
Ala Gln Ala Pro Asp Gly Ala Ser Glu Pro Arg Ala Ser Ala Ser Arg
                 85                  90                  95

Pro Gln Pro Ala Pro Ala Asp Gly Ala Asp Pro Pro Ala Glu Glu
            100                 105                 110

Pro Glu Ala Arg Pro Asp Gly Glu Gly Ser Pro Gly Lys Ala Arg Pro
            115                 120                 125

Gly Thr Ala Arg Arg Pro Gly Ala Ala Ser Gly Glu Arg Asp Asp
130                 135                 140

Arg Gly Pro Pro Ala Ser Val Ala Ala Leu Arg Ser Asn Phe Glu Arg
145                 150                 155                 160

Ile Arg Lys Gly His Gly Gln Pro Gly Ala Asp Ala Glu Lys Pro Phe
                165                 170                 175

Tyr Val Asn Val Glu Phe His His Glu Arg Gly Leu Val Lys Val Asn
                180                 185                 190

Asp Lys Glu Val Ser Asp Arg Ile Ser Ser Leu Gly Ser Gln Ala Met
        195                 200                 205

Gln Met Glu Arg Lys Lys Ser Gln His Gly Ala Gly Ser Ser Val Gly
    210                 215                 220

Asp Ala Ser Arg Pro Pro Tyr Arg Gly Arg Ser Ser Glu Ser Ser Cys
225                 230                 235                 240

Gly Val Asp Gly Asp Tyr Glu Asp Ala Glu Leu Asn Pro Arg Phe Leu
                245                 250                 255

Lys Asp Asn Leu Ile Asp Ala Asn Gly Gly Ser Arg Pro Pro Trp Pro
                260                 265                 270

Pro Leu Glu Tyr Gln Pro Tyr Gln Ser Ile Tyr Val Gly Gly Met Met
            275                 280                 285

Glu Gly Glu Gly Lys Gly Pro Leu Leu Arg Ser Gln Ser Thr Ser Glu
    290                 295                 300

Gln Glu Lys Arg Leu Thr Trp Pro Arg Arg Ser Tyr Ser Pro Arg Ser
305                 310                 315                 320

Phe Glu Asp Cys Gly Gly Gly Tyr Thr Pro Asp Cys Ser Ser Asn Glu
                325                 330                 335

Asn Leu Thr Ser Ser Glu Glu Asp Phe Ser Ser Gly Gln Ser Ser Arg
            340                 345                 350

Val Ser Pro Ser Pro Thr Thr Tyr Arg Met Phe Arg Asp Lys Ser Arg
        355                 360                 365

Ser Pro Ser Gln Asn Ser Gln Gln Ser Phe Asp Ser Ser Pro Pro
    370                 375                 380

Thr Pro Gln Cys His Lys Arg His Arg His Cys Pro Val Val Val Ser
385                 390                 395                 400

Glu Ala Thr Ile Val Gly Val Arg Lys Thr Gly Gln Ile
                405                 410
```

<210> SEQ ID NO 8
<211> LENGTH: 18
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

```
Gly His Gly Gln Pro Gly Ala Asp Ala Glu Lys Pro Phe Tyr Val Asn
  1               5                  10                  15

Val Glu
```

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Arg Ser Tyr Ser Pro Arg Ser
 1               5

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Val Ser Pro Ser Pro Thr Thr Tyr Arg Met Phe Arg
 1               5                  10

<210> SEQ ID NO 11
<211> LENGTH: 39
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Phe Leu Lys Asp Asn Leu Ile Asp Ala Asn Gly Gly Ser Arg Pro Pro
 1               5                  10                  15

Trp Pro Pro Leu Glu Tyr Gln Pro Tyr Gln Ser Ile Tyr Val Gly Gly
            20                  25                  30

Met Met Glu Gly Glu Gly Lys
        35

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Asn Ser Leu Glu Thr Leu Leu Tyr Lys
 1               5

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Tyr Val Asn Val
 1

<210> SEQ ID NO 14
<211> LENGTH: 14

```
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
ctagtctaga ctag                                                           14

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
cccctggagt tccagcccta c                                                   21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
cagagcatct tcgtcggggg c                                                   21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
cgcaggtcct tctcccccg g                                                    21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
ggaggcggct ttaccccgga c                                                   21

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
tggtcgactc gcgactcttc c                                                   21

<210> SEQ ID NO 20
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      Primer

<400> SEQUENCE: 20
atcatcaccg acacatcc                                                    18

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
ggatgtgtcg gtgatgat                                                    18

<210> SEQ ID NO 22
<211> LENGTH: 17
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 22

Ser Ser Arg Val Ser Pro Ser Pro Thr Thr Tyr Arg Met Phe Arg Asp
  1               5                  10                  15

Lys

<210> SEQ ID NO 23
<211> LENGTH: 53
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 23

Ser Gln Ser Thr Ser Glu Gln Glu Lys Arg Leu Thr Trp Pro Arg Arg
  1               5                  10                  15

Ser Tyr Ser Pro Arg Ser Phe Glu Asp Cys Gly Gly Tyr Thr Pro
             20                  25                  30

Asp Cys Ser Ser Asn Glu Asn Leu Thr Ser Ser Glu Glu Asp Phe Ser
         35                  40                  45

Ser Gly Gln Ser Ser
     50

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 24

Phe Tyr Val Asn Val
  1               5

<210> SEQ ID NO 25
<211> LENGTH: 5
<212> TYPE: PRT
```

```
<213> ORGANISM: Artificial Sequence
<220> FEATURE:
<223> OTHER INFORMATION: Description of Artificial Sequence:  Synthetic
      Peptide

<400> SEQUENCE: 25

Thr Tyr Arg Met Phe
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 26

Tyr Gln Ser Ile Tyr Val Gly
  1               5

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 27

Pro Gly Ala Asp Ala Glu Lys Pro Phe Tyr Val Asn Val
  1               5                  10

<210> SEQ ID NO 28
<211> LENGTH: 350
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 28

Ala Lys Glu Lys Lys Ser Tyr Asp Arg Gln Arg Trp Gly Phe Arg Arg
  1               5                  10                  15

Ala Ala Gln Ala Pro Asp Gly Ala Ser Glu Pro Arg Ala Ser Ala Ser
             20                  25                  30

Arg Pro Gln Pro Ala Pro Ala Asp Gly Ala Asp Pro Pro Ala Glu
         35                  40                  45

Glu Pro Glu Ala Arg Pro Asp Gly Glu Gly Ser Pro Gly Lys Ala Arg
     50                  55                  60

Pro Gly Thr Ala Arg Arg Pro Gly Ala Ala Ser Gly Glu Arg Asp
 65                  70                  75                  80

Asp Arg Gly Pro Pro Ala Ser Val Ala Ala Leu Arg Ser Asn Phe Glu
                 85                  90                  95

Arg Ile Arg Lys Gly His Gly Gln Pro Gly Ala Asp Ala Glu Lys Pro
            100                 105                 110

Phe Tyr Val Asn Val Glu Phe His His Glu Arg Gly Leu Val Lys Val
            115                 120                 125

Asn Asp Lys Glu Val Ser Asp Arg Ile Ser Ser Leu Gly Ser Gln Ala
        130                 135                 140

Met Gln Met Glu Arg Lys Lys Ser Gln His Gly Ala Gly Ser Ser Val
145                 150                 155                 160
```

```
Gly Asp Ala Ser Arg Pro Pro Tyr Arg Gly Arg Ser Ser Glu Ser Ser
                165             170             175

Cys Gly Val Asp Gly Asp Tyr Glu Asp Ala Glu Leu Asn Pro Arg Phe
            180             185             190

Leu Lys Asp Asn Leu Ile Asp Ala Asn Gly Gly Ser Arg Pro Pro Trp
        195             200             205

Pro Pro Leu Glu Tyr Gln Pro Tyr Gln Ser Ile Tyr Val Gly Gly Met
    210             215             220

Met Glu Gly Glu Gly Lys Gly Pro Leu Leu Arg Ser Gln Ser Thr Ser
225             230             235             240

Glu Gln Glu Lys Arg Leu Thr Trp Pro Arg Arg Ser Tyr Ser Pro Arg
            245             250             255

Ser Phe Glu Asp Cys Gly Gly Gly Tyr Thr Pro Asp Cys Ser Ser Asn
            260             265             270

Glu Asn Leu Thr Ser Ser Glu Glu Asp Phe Ser Ser Gly Gln Ser Ser
        275             280             285

Arg Val Ser Pro Ser Pro Thr Thr Tyr Arg Met Phe Arg Asp Lys Ser
        290             295             300

Arg Ser Pro Ser Gln Asn Ser Gln Gln Ser Phe Asp Ser Ser Ser Pro
305             310             315             320

Pro Thr Pro Gln Cys His Lys Arg His Arg His Cys Pro Val Val Val
            325             330             335

Ser Glu Ala Thr Ile Val Gly Val Arg Lys Thr Gly Gln Ile
            340             345             350
```